(12) United States Patent
Taniyama et al.

(10) Patent No.: US 8,017,119 B2
(45) Date of Patent: Sep. 13, 2011

(54) ANTIBODY AGAINST PERIOSTIN, AND A PHARMACEUTICAL COMPOSITION COMPRISING IT FOR PREVENTING OR TREATING A DISEASE IN WHICH PERIOSTIN IS INVOLVED

(75) Inventors: Yoshiaki Taniyama, Osaka (JP); Ryuichi Morishita, Osaka (JP); Naruto Katsuragi, Osaka (JP)

(73) Assignees: Daiichi Sankyo Company, Ltd., Tokyo (JP); Osaka University, Osaka (JP)

( * ) Notice: Subject to any disclaimer, the term of this patent is extended or adjusted under 35 U.S.C. 154(b) by 0 days.

(21) Appl. No.: 12/147,331

(22) Filed: Jun. 26, 2008

(65) Prior Publication Data
US 2009/0074788 A1    Mar. 19, 2009

Related U.S. Application Data

(63) Continuation-in-part of application No. PCT/JP2006/326280, filed on Dec. 28, 2006.

(30) Foreign Application Priority Data

Dec. 28, 2005 (JP) .................. 2005-380009
Jun. 27, 2007 (JP) .................. 2007-169494
Feb. 14, 2008 (JP) .................. 2008-033827

(51) Int. Cl.
*A61K 39/395* (2006.01)
(52) U.S. Cl. .................. 424/138.1; 424/139.1
(58) Field of Classification Search .................. None
See application file for complete search history.

(56) References Cited

U.S. PATENT DOCUMENTS

2004/0029827 A1* 2/2004 Kawashima et al. ............ 514/47
2005/0042642 A1* 2/2005 Monahan et al. .................. 435/6

FOREIGN PATENT DOCUMENTS

| EP | 0562508 A2 | 6/1998 |
|---|---|---|
| WO | WO 02/20055 | 3/2002 |
| WO | WO 03/016471 | 2/2003 |
| WO | WO 2004/106495 | 12/2004 |
| WO | WO 2005/019471 | 3/2005 |
| WO | WO 2007/077934 | 7/2007 |

OTHER PUBLICATIONS

Johnson et al CAncer Treatment Reviews (1975) vol. 2 p. 1-31.*
Essell (J. NIH Res. 1995 7:46).*
Spitler (Cancer Biotherapy, 1995, 10:1-3).*
Greenbaum et al. (Genome Biology, 2003, vol. 4, Issue 9, pp. 117.1-117.8.*
Gillan, (Sep. 2002) "Periostin Secreted by Epithelial Ovarian Carcinoma Is a Ligand for αvβ3 and αvβ5 Integrins and Promotes Cell Motility." Cancer Research 62: 5358-5364.
Gonzalez, et al. (2003) Arch Otolaryngol Head Neck Surg. 129: 754-759.
Horiuchi, et al. (1999) "Identification and characterization of a novel protein, periostin, with restricted expression to periosteum and peirodontal ligament and increased expression by transforming growth factor beta." Journal of Bone and Mineral Research 14(7): 1239-1249.
Katsuragi, et al. (2004) "Periostin as a novel factor responsible for ventricular dilation." Circulation 110(13): 1806-1813.
Lindner, et al. (Jan. 2005) "Vascular Injury Induces Expression or Periostin—Implications for Vascular Cell Differentiation and Migration." Arterioscler Thromb Vasc. Biol. 25:77-83.
Litvin, et al. (2004) "Expression and Function of Periostin-Isoforms in Bone." Journal of Cellular Biochemistry 92: 1044-1061.
Peters, et al. (2001) "Molecular Anatomy of an Intracranial Aneurysm: Coordinated Expression of Genes Involved in Wound Healing and Tissue Remodeling." Stoke 32: 1036-1042.
Sasaki, et al. (2002) Am. J Obstet Gynecol. 186: 103-108.
Sasaki, et al. (2003) Breast Cancer Res Treat. 77: 245-252.
Shao, et al. (May 2004) "Acquired Expression of Periostin by Human Brest Cancers Promotes Tumor Angiogenesis through Up-Regulation of Vascular Endothelial Growth Factor Receptor 2 Expression." Molecular and Cellular Biology: 3992-4003.
Tai, et al. (2005) "Periostin Induction in Tumor Cell Line Explants and Inhibition of In Vitro Cell Growth by Anti-Periostin Antibodies." Carcinogenesis 26(5): 908-915.
Takeshita, (1993) "Osteoblast-Specific Factor 2: Cloning of Putative Bone Adhesion Protein with Homology with the Insect Protein Fasciclin I." Biochem. J. 294: 271-278.
Taniyama, et al. (Sep. 20, 2004) "Periostin as a Novel Factor Responsible for Ventricular Dilation." Folia endorcinoligca Japonica 80(2): 496.
Wang, et al. (2003) "Effects of Pressure Overload on Extracellular Matrix Expression in the Heart of the Atrial Natriuretic Peptide-Null Mouse." Hypertension 42: 88-95.
Litvin et al., Cardiovascular Pathology, vol. 15, pp. 24-32 (2006).
Extended European Search Report for European Application No. 06843658.3 mailed on Jul. 29, 2010.
International Search Report in PCT/JP2008/061768 mailed Jul. 29, 2008.
Kim et al., "Analysis of Correlation Between Alternative Splicing Variants of Periostatin Gene and Malignant Phenotypes," Annual Meeting of the Japan Cancer Association Kiji, 2006, Vol. 65th, p. 302, Abstract No. P-572.
Kim et al., "Periostatin is Down-Regulated in High Grade Human Bladder Cancers and Suppresses in vitro Cell Invasiveness and in vivo metastasis of Cancer Cells," Int. J. Cancer, 117:51-58 (2005).

(Continued)

*Primary Examiner* — Sheela J Huff
(74) *Attorney, Agent, or Firm* — Hunton & Williams LLP

(57) ABSTRACT

The present invention provides an antibody against a periostin isoform having anti-cell adhesive activity, especially an anti-periostin antibody having the ability to neutralize anti-cell adhesive properties, as well as a prophylactic or therapeutic agent for periostin-related diseases comprising the antibody. The present invention also provides methods for detecting and quantifying the periostin isoform in a sample by using the antibody, as well as a method for diagnosing periostin-related diseases comprising measuring the amount of the periostin isoform by the detection or quantification method.

24 Claims, 38 Drawing Sheets

OTHER PUBLICATIONS

Kim et al., "Role of Alternative Splicing of Periostin in Human Bladder Carcinogenesis," Intl. J. Oncology, 32:161-169 (2008).

Lichtinghagen et al., "Different mRNA and Protein Expression of Matrix Metalloproteinases 2 and 9 and Tissue Inhibitor of Metalloproteinases 1 in Benign Malignant Prostate Tissue," European Urology, vol. 42, pp. 398-406 (2002).

Orntoft et al., Genome-wide Study of Gene Copy Numbers, Transcripts, and Protein Levels in Pairs of Non-invasive and Invasive Human Transitional Cell Carcinomas, molecular & Cellular Preteomics, 1.1 (2002).

Chen et al., "Discordant Protein and mRNA Expression in Lung Adenocarcinomas," Molecular & Cellular Proteomics, 1.4 (2002).

* cited by examiner

FN: Group treated with fibronectin (positive control)
PN-1: Group treated with human periostin (hPN-1)
BSA: Group treated with bovine serum albumin (negative control)

** $p < 0.01$

ANTIBODY AGAINST PERIOSTIN, AND A PHARMACEUTICAL COMPOSITION COMPRISING IT FOR PREVENTING OR TREATING A DISEASE IN WHICH PERIOSTIN IS INVOLVED

CROSS-REFERENCE TO RELATED APPLICATIONS

This application is a continuation-in-part of International Patent Application No. PCT/JP2006/326280, filed Dec. 28, 2006, which claims priority to Japan 380009/2005, filed Dec. 28, 2005, Japan 169494/2007, filed Jun. 27, 2007, JP 33827/2008, Feb. 14, 2008, the disclosures of each of which are hereby incorporated by reference.

BACKGROUND OF THE INVENTION (i) Field of the Invention:

The present invention relates to antibodies against periostin isoforms having anti-cell adhesive properties, especially anti-periostin antibodies having the ability to neutralize anti-cell adhesive properties. More specifically, it relates to anti-periostin antibodies specifically recognizing a site responsible for anti-cell adhesion of periostin having anti-cell adhesive properties specifically expressed in interstitial tissue during tissue restructuring such as cardiac hypertrophy, which are useful for prevention or treatment of periostin-related diseases, such as heart failure, or are useful for diagnosis of these diseases.

The present invention also relates to a pharmaceutical composition for cancer treatment, which comprises an antibody against a peptide encoded by the Exon-17 region of periostin. More specifically, the present invention relates to a pharmaceutical composition for cancer treatment, which comprises an anti-periostin antibody recognizing a splice variant of periostin having anti-cell adhesive properties specifically expressed in interstitial tissue during tissue restructuring such as cancer tissues, or a method and reagent for cancer diagnosis using the above anti-periostin antibody.

(ii) Description of the Related Art:

Chronic heart failure is a condition in which the heart cannot pump enough blood to various organs due to decreased myocardial contractility. Conventionally, it has been treated with cardiotonic drugs that increase myocardial contractility such as digitalis drugs. However, these drugs have been shown to impair vital prognosis during long-term administration, due to excessive consumption of myocardial energy. Thus, recently prevailing therapies are those using diuretics, β-blockers or angiotensin inhibitors that reduce excessive workload on the heart by the sympathetic nervous system or renin-angiotensin-aldosterone system activated in heart failure condition. However, patients with heart failure have limited activities in their daily life and cannot maintain their quality of life because they are prohibited from hard exercise or the like. Moreover, the vital prognosis of patients with heart failure cannot be fully ensured. It is therefore desirable to develop a new drug effective for treating heart failure, which enables an improvement in the quality of life and an improvement in long-term vital prognosis.

In recent years, the healing rate of cancer has been rising steadily with advances in cancer therapy. In particular, the improved success rate of primary carcinoma removal by surgical operation, radiation therapy or chemotherapy contributes to the advance of cancer therapy. However, on a worldwide basis, the cancer mortality rate continues to increase for reasons such as aging population, and cancer remains the primary cause of death. This is because not a few patients will die of cancer metastasis even when primary carcinoma removal is completely achieved, and there is a limit to surgical operation, radiation therapy or chemotherapy for completely blocking cancer metastasis, so that the distant metastasis of cancer is still directly or indirectly related to the cause of cancer death. Cancer metastasis is mediated by processes such as invasion of cancer cells released from their primary tumor into blood vessels or lymph vessels, selective migration of cancer cells to metastatic organs, invasion of cancer cells from blood vessels into metastatic organs, growth of cancer cells supported by the microenvironment where metastasis occurred, and angiogenesis-associated growth of tumors whose diameter exceeds several millimeters (Folkman J. Semin. Cancer Biol, 3, 65-71, (1992), Hanahan D. et al. Cell, 86, 353-364 (1996)). Among these complex processes for metastasis establishment, invasion and metastasis induced by the enhanced motility of cancer cells are very important stages (Liotta L A. et al. Cell, 64, 327-336 (1991)). Until now, it has been reported that highly metastatic cancer cells produce an autocrine motility factor by themselves to enhance their own motion (Liotta L A. et al. Proc. Natl. Acad. Sci., 83, 3302-3306 (1986)). Inhibitory substances against this malignant factor are expected as metastasis inhibitors, but no specific inhibitor has been found at present.

On the other hand, periostin is an extracellular matrix protein and consists of a polypeptide having a molecular weight of about 90000. Each polypeptide chain has a signal sequence, a cysteine-rich domain, a fourfold repeated domain, and a C-terminal domain.

Periostin was first called osteoblast-specific factor-2 (OSF-2) and was isolated and identified as a gene specifically expressed in the mouse osteoblast cell line MC3T3-E1 (JPA No. HEI-5-268982, Takeshita S. et al., Biochem J (1993) 294, 271-8), and later came to be known as periostin and was reported to have adhesion-promoting activity in osteoblast cells (Horiuchi K. et al., J. Bone Miner. Res. (1999) 14, 1239-49).

In early studies, periostin was thought to be an extracellular matrix specifically expressed in bone tissue. However, it is currently known to be expressed not only in bone tissue but also very highly at the onset of heart failure (Katsuragi N. et al., Circulation (2004) 110, 1806-13, Wang D. et al., Hypertension (2003) 42, 88-95), aneurysms (Peters D G. et al., Stroke (2001) 32, 1036-42), highly metastatic cancers (Shao R. et al., Mol Cell Biol. (2004) 24, 3992-4003, Gonzalez H E. et al., Arch Otolaryngol Head Neck Surg. (2003) 129, 754-9, Sasaki H. et al., Breast Cancer Res Treat. (2003) 77, 245-52), preeclampsia (Sasaki H. et al., Am J Obstet. Gynecol. (2002) 186, 103-8) as well as very slightly in normal tissue. Moreover, some periostin splice variants were shown to be expressed in osteoblasts (Takeshita S. et al., Biochem J (1993) 294, 271-8, Horiuchi K. et al., J. Bone Miner. Res. (1999) 14, 1239-49, Litvin J. et al., J Cell Biochem. (2004) 92, 1044-61, Katsuragi N. et al., Circulation (2004) 110, 1806-13).

As to functions of periostin, a periostin splice variant consisting of 811 amino acids (corresponding to PN-2 in FIG. 1) (Horiuchi K. et al., J. Bone Miner. Res. (1999) 14, 1239-49) and a periostin splice variant consisting of 782 amino acids (Gillan L, et al., Cancer Res. (2002) 62, 5358-64) were reported to have cell adhesive properties. In contrast, it has been reported that a periostin splice variant consisting of 838 amino acids (corresponding to PN-1 in FIG. 1) prevents heart fibroblasts from adhering to a plate coated with the periostin splicing variant, i.e., has no cell adhesive activity; the gene expression of the periostin splice variant consisting of 838 amino acids (corresponding to PN-1 in FIG. 1) is significantly increased in heart failure model rats as compared with normal rats; this variant is an aggravating factor inducing heart dilation; and that the survival rate was significantly increased by inhibition of the expression of this protein (Katsuragi N. et al., Circulation (2004) 110, 1806-13). Further, there is a report of a prophylactic or therapeutic agent for heart failure, in which an antisense nucleotide against the periostin splice variant consisting of 838 amino acids is used to suppress expression of the periostin splicing variant (Republication WO02/020055).

In addition, the inventors of the present invention have reported a prophylactic or therapeutic agent for heart failure, which is based on the following findings: the periostin splice variant consisting of 811 amino acids (corresponding to PN-2 in FIG. 1) is involved in cell adhesion whereas the periostin splice variant consisting of 838 amino acids (corresponding to PN-1 in FIG. 1) has cell detachment activity; an antibody against an antigen composed of the Exon-17 sequence inhibits the cell detachment activity; and improved heart function was observed in acute myocardial infarction model animals (Japanese Patent Application No. 2005-380009).

As to cancers, various reports have been issued on high level expression of periostin in highly metastatic cancers [Erkan M. et al. Gastroenterology, 132(4), 1447-64 (2007) (pancreatic cancer), Siriwardena B S. et al. Br J Cancer, 95(10), 1396-403 (2006) (oral cancer), Baril P. et al. Oncogene, 26(14), 2082-94 (2007) (pancreatic cancer), Grigoriadis A. et al. Breast Cancer Res, 8(5), R56 (2006) (breast cancer), Kudo Y. et al. Cancer Res, 66(14), 6928-35 (2006) (head and neck cancer), Bao S. et al. Cancer Cell. 5(4), 329-39 (2004) (colon cancer), Shao R. et al., Mol Cell Biol. (2004) 24, 3992-4003 (breast cancer), Sasaki H. et al., Breast Cancer Res Treat. (2003) 77, 245-52 (breast cancer), Sasaki H. et al. Cancer Lett., 72(1), 37-42 (2001) (thymic cancer), Sasaki H. et al. Cancer, 92(4), 843-8 (2001) (non-small cell lung cancer), Gonzalez H E. et al., Arch Otolaryngol Head Neck Surg. (2003) 129, 754-9 (head and neck squamous cell carcinoma)]. Also, highly metastatic cancers are reported to express the transcription factor Twist at high level (Thiery J P. et al. Nat. Med. 10(8), 777-8 (2004), Yang J, et al. Cell. 117(7), 927-39 (2004)) and receive attention, but there is a report showing that Twist is also located in the promoter region of periostin (Oshima A, et al. J Cell Biochem, 86(4), 792-804 (2002)). In addition, it has been reported that the human fetal kidney epithelial cell line 293T, which is carcinogenic and non-metastatic, enhances its invasion ability when introduced with the periostin gene (Yan W. et al. *J Biol. Chem.*, 281(28), 19700-8 (2006))). It has also been reported that a rat homolog of mouse periostin was less expressed in various cancer cells, introduction of the periostin gene into bladder cancer cells inhibited invasion of the bladder cancer cells, and introduction of the periostin gene into mouse melanoma B16-F10 cells inhibited their metastasis to lung (Kim C J, et al. Int J Cancer, 117(1), 51-8 (2005)).

As shown above, it has been suggested that expression of the periostin gene is related to the pathology of heart failure, but the relationship between the structure of periostin splicing variants and heart failure has been unknown.

Also, it has been suggested that expression of the periostin gene is related not only to the pathology of heart failure, but also to the pathology of cancer. However, it is unknown what function each splice variant has on the progress of cancer condition.

Thus, we made an attempt to clarify the structure of periostin related to the pathology of heart failure by using antibodies.

As to periostin antibodies, there are reports of an antibody related to the inhibition of chemotaxis of periostin (Lindner V. et al., Arterioscler Thromb Vasc Biol. (2005) 25, 77-83) and an antibody having inhibitory activity against periostin-induced cell growth (Tai I T, et al., Carcinogenesis (2005) 26, 908-15). However, there has been neither a report of antibodies showing the structure of a region responsible for cell adhesive activity of periostin nor a report showing the relation between the cell adhesive activity of periostin and diseases such as heart failure.

As to antibodies against periostin, there are reports of an anti-periostin antibody which inhibits periostin overexpression-enhanced migration of mesenchymal cells (Lindner V. et al., Arterioscler Thromb Vasc Biol. (2005) 25, 77-83) and an anti-periostin antibody which inhibits periostin-induced growth and cell differentiation in colorectal cancer (Tai I T. et al., Carcinogenesis (2005) 26, 908-15).

SUMMARY OF THE INVENTION

The present invention aims to provide, e.g., a novel and effective prophylactic or therapeutic agent for heart failure, which enables an improvement in the quality of life and an improvement in long-term vital prognosis. More specifically, the present invention aims to provide an antibody against a periostin isoform having anti-cell adhesive activity, specifically recognizing a site responsible for anti-cell adhesion. The present invention also aims to provide a hybridoma producing the antibody, a method for producing the hybridoma, and a method for producing the antibody by culturing the hybridoma. The present invention further aims to provide a pharmaceutical composition comprising the antibody for preventing or treating a disease in which a periostin isoform having anti-cell adhesive activity is involved. The present invention further aims to provide a method for preventing or treating a disease in which a periostin isoform having anti-cell adhesive activity is involved, comprising administering the pharmaceutical composition to a patient, as well as a method for diagnosing the disease.

The present invention also aims to provide a novel cancer therapeutic agent which enables an improvement in the quality of life and an improvement in long-term vital prognosis and whose mechanism is different from that of existing agents. The present invention further aims to provide a method and reagent for cancer diagnosis.

DETAILED DESCRIPTION OF THE INVENTION

We clarified that a periostin splicing variant having no cell adhesive activity (PN-1) has anti-cell adhesive activity, i.e., the activity of detachment of adhered cells. On the other hand, we also confirmed that periostin having cell adhesive activity (PN-2) has no anti-cell adhesive activity, i.e., does not detach adhered cells. Moreover, we noted a difference in structure and cell adhesive activity between periostin splice variants having anti-cell adhesive activity (PN-1) and periostin showing no anti-cell adhesive activity (PN-2), and considered that diseases related to periostin isoforms having anti-cell adhesive activity could be prevented or treated by inhibiting a region specifically present in the periostin splice variants having anti-cell adhesive activity. In other words, we considered that inhibitors against said region might be useful as prophylactic or therapeutic agents for diseases related to periostin isoforms having anti-cell adhesive activity.

Analysis of periostin splice variants highly expressed during heart failure revealed that the C-terminal domains in which the splice variants are formed consist of exons 15 to 23; specifically rats have the following variants (1) to (4):
(1) a variant retaining all the exons (called PN-1; consisting of 838 amino acids shown as SEQ ID NO: 1; the cDNA sequence shown as SEQ ID NO: 6),
(2) a variant lacking Exon-17 (called PN-2; consisting of 811 amino acids shown as SEQ ID NO: 5; 27 amino acids (Exon-17) shown in SEQ ID NO: 3 are deleted from PN-1; the cDNA sequence shown as SEQ ID NO: 7),
(3) a variant lacking Exon-21 (called PN-3; consisting of 810 amino acids),
(4) a variant lacking Exon-17 and Exon-21 (called PN-4; consisting of 783 amino acids).

In addition to rats, mouse and human PN-1 and PN-2 were also found (mouse PN-1: SEQ ID NO: 8 (amino acid sequence), SEQ ID NO: 9 (cDNA sequence); mouse PN-2: SEQ ID NO: 10 (amino acid sequence), SEQ ID NO: 11 (cDNA sequence); human PN-1: SEQ ID NO: 12 (cDNA sequence); human PN-2: SEQ ID NO: 13 (amino acid sequence), SEQ ID NO: 14 (cDNA sequence)). Among them, PN-1 was highly expressed while PN-2 and PN-3 were expressed to a lesser extent in rat cardiac hypertrophy tissue. Thus, we contemplated preparing an antibody specifically recognizing the amino acid residue part encoded by Exon-17 as an inhibitor against that site, which site is structurally different in PN-1 and PN-2 and exclusively found in PN-1.

In order to prepare an antibody, the material used as an immunogen must be hydrophilic, and if an antibody is to be prepared using a part of a large polypeptide such as protein, the part used as an immunogen must be exposed on the surface of the protein to form an epitope site. Thus, in order to examine the possibility of using the Exon-17 peptide chain as an antigen, an epitope search was initially performed using Accelrys software that is widely used in the field of bioinformatics Mac Vector 7.2. It was judged from "Hydrophilicity", "Surface Probability" and "Antigenicity" that TTKIITKLVE-PKIKVIQGSLQPIIKTE (SEQ ID NO: 3) of the Exon-17 region is mostly hydrophobic, suggesting that this region is very unlikely to be exposed on the surface of the protein molecule and has no immunogenicity, so it cannot be used to prepare an antibody, and therefore, it was presumed that it would be difficult to use to practically prepare an antibody.

However, we ventured to prepare an antibody against the amino acid sequence encoded by Exon-17 on the assumption that the use of an antibody against a polypeptide region encoded by Exon-17 specifically found in PN-1 would be most suitable for specifically inhibiting functions of PN-1. A peptide consisting of 27 amino acids constituting a peptide encoded by the Exon-17 region was synthesized and used to immunize rabbits, and the resulting serum was purified to give an IgG fraction, whereby an anti-Exon-17 peptide polyclonal antibody was prepared. When periostin protein PN-1 was then added to an 80% confluent culture of heart fibroblasts, nearly 100% cell detachment (i.e., anti-cell adhesive activity) was observed. Administration of the anti-Exon-17 peptide antibody to this experimental system inhibited the cell detachment mediated by periostin protein PN-1, showing that the anti-Exon-17 peptide antibody is an antibody having a neutralizing activity against periostin protein PN-1. Then, acute myocardial infarction model rats were prepared and weekly administration of the anti-Exon-17 peptide antibody was continued to show that heart dilation was significantly inhibited 4 weeks after the preparation of the models, and that heart function was improved. It was also shown that these properties were sustained and cardiac fibrosis was inhibited even 8 weeks after the preparation of the models. This indicates that the anti-Exon-17 peptide antibody is an antibody having the activity of inhibiting heart dilation and cardiac fibrosis associated with the progress of heart failure condition, and the activity of improving heart function, leading to accomplishment of the present invention.

As a solution to the problems described above, the present invention provides an antibody against a periostin isoform having anti-cell adhesive activity specifically expressed in the heart during heart failure or the like, particularly an antibody specifically recognizing a site responsible for anti-cell adhesion.

Based on these findings, the inventors of the present invention deduced that the cell detachment effect (i.e., cell-releasing effect) of PN-1 protein is related to the release of cancer cells from their primary tumor during the cancer metastasis processes mentioned above, and thereby facilitates cancer metastasis. Thus, they attempted to clarify the relationship between PN-1 protein and the pathology of cancer.

The C-terminal domains in which periostin splice variants are formed consist of exons 15 to 23; specifically rats have the following variants (1) to (4):
(1) a variant retaining all the exons (called PN-1; consisting of 838 amino acids shown as SEQ ID NO: 1; the cDNA sequence shown as SEQ ID NO: 6),
(2) a variant lacking Exon-17 (called PN-2; consisting of 811 amino acids shown as SEQ ID NO: 5; 27 amino acids (Exon-17) shown in SEQ ID NO: 3 are deleted from PN-1; the cDNA sequence shown as SEQ ID NO: 7),
(3) a variant lacking Exon-21 (called PN-3; consisting of 810 amino acids),
(4) a variant lacking Exon-17 and Exon-21 (called PN-4; consisting of 783 amino acids).

In addition to rats, mouse and human PN-1 and PN-2 were also found (mouse PN-1: SEQ ID NO: 8 (amino acid sequence), SEQ ID NO: 9 (cDNA sequence); mouse PN-2: SEQ ID NO: 10 (amino acid sequence), SEQ ID NO: 11 (cDNA sequence); human PN-1: SEQ ID NO: 12 (cDNA sequence); human PN-2: SEQ ID NO: 13 (amino acid sequence), SEQ ID NO: 14 (cDNA sequence)).

Further, analysis of periostin splice variants highly expressed during the pathology of cancer revealed that PN-1 having the functions of inhibiting cell adhesion and separating adhered cells is expressed at very high level in tumor tissues of model mice for lung metastasis of mouse melanoma B16-F10 cells or mouse 4T1 breast cancer cells when compared to normal tissues, thus showing that PN-1 is expressed at a very high level during the pathology of cancer.

Then, the inventors of the present invention considered that a site structurally different between PN-1 having the function of inhibiting cell adhesion and PN-2 having the function of allowing cell adhesion, i.e., the Exon-17 region that is found only in PN-1 is a region related to the inhibition of cell adhesion, and further considered that when inhibiting this Exon-17 region, it is possible to suppress the PN-1's inhibitory function on cell adhesion and further inhibit cancer metastasis. Thus, the inventors contemplated preparing an antibody specifically recognizing a peptide part consisting of an amino acid sequence encoded by Exon-17 as an inhibitor against that site, which site is found in PN-1.

In order to prepare an antibody, the material used as an immunogen must be hydrophilic, and if an antibody is to be prepared using a part of a large polypeptide such as protein, the part used as an immunogen must be exposed on the surface of the protein to form an epitope site. Thus, in order to examine the possibility of using the Exon-17 peptide chain as an antigen, an epitope search was initially performed using Accelrys software Mac Vector 7.2 that is widely used in the field of bioinformatics. It was judged from "Hydrophilicity", "Surface Probability" and "Antigenicity" that TTKIITKLVE-PKIKVIQGSLQPIIKTE (SEQ ID NO: 3) of the Exon-17 region is mostly hydrophobic, suggesting that this region is very unlikely to be exposed on the surface of the protein molecule and has no immunogenicity, so it cannot be used to prepare an antibody, and therefore, it was presumed that it would be difficult to use to practically prepare an antibody.

However, when a peptide consisting of 27 amino acids constituting a peptide encoded by the Exon-17 region was synthesized and used to immunize rabbits, and the resulting serum was purified to give an IgG fraction, whereby an anti-Exon-17 peptide polyclonal antibody was prepared, it was surprisingly possible to prepare an antibody against a peptide region encoded by Exon-17 specifically found in PN-1 (hereinafter referred to as "anti-Exon-17 polyclonal antibody") although the peptide was presumed to be hydrophobic and non-immunogenic.

When PN-1 protein was then added to an 80% confluent culture of mouse melanoma B16-F10 cells or mouse 4T1 breast cancer cells, nearly 100% cell elimination (i.e., anti-cell adhesive activity) was observed. Administration of the anti-Exon-17 polyclonal antibody to this experimental system inhibited the cell elimination mediated by PN-1 protein, showing that the anti-Exon-17 polyclonal antibody is an antibody having a neutralizing activity against PN-1 protein. Moreover, addition of the anti-Exon-17 polyclonal antibody to mouse melanoma B16-F10 cells or mouse 4T1 breast cancer cells inhibited cell proliferation, showing that the anti-Exon-17 polyclonal antibody also has an inhibitory effect on proliferation of mouse melanoma B16-F10 cells or mouse 4T1 breast cancer cells.

When the anti-Exon-17 polyclonal antibody was then continued to be administered once a week to model mice which will develop lung metastasis when injected with mouse melanoma B16-F10 cells or mouse 4T1 breast cancer cells into their soles, this antibody significantly inhibited not only primary tumor growth, but also the metastasis rate and the number of metastasized colonies from primary tumor to lung, within 3 to 5 weeks after model preparation. Further, in mouse 4T1 breast cancer cells, bone invasion of the breast cancer cells from primary tumor and bone destruction caused by bone invasion of cancer were significantly inhibited. This suggested that a neutralizing antibody against PN-1 suppresses the PN-1's inhibitory effect on adhesion and has the potential to act as a novel therapeutic agent for inhibiting the growth of malignant melanoma or breast cancer cells, bone invasion, bone destruction and lung metastasis. Moreover, when the same study was also performed on breast cancer 4T1 cells, not only primary tumor growth, but also the number of colonies metastasized from primary tumor to lung was significantly inhibited within 3 weeks after preparation of the model for lung metastasis of mouse 4T1 breast cancer cells. This indicated that the anti-Exon-17 polyclonal antibody is an antibody having the activity of inhibiting primary tumor growth associated with the progress of cancer condition, the activity of inhibiting bone invasion, the activity of bone destruction caused by bone invasion of cancer, and having the activity of inhibiting metastasis from primary tumor to lung. This showed that PN-1 protein has the function of causing the growth of primary tumor and metastasis from primary tumor during the pathology of cancer, leading to a finding that the progress of these cancer conditions can be inhibited by such an antibody against a peptide region encoded by Exon-17 specifically found in PN-1.

Furthermore, the inventors of the present invention prepared a monoclonal antibody against the human periostin Exon-17 peptide chain (hereinafter referred to as "anti-Exon-17 monoclonal antibody"). In experiments using model mice for lung metastasis of mouse melanoma B16-F10 cells, administration of the anti-Exon-17 monoclonal antibody showed cancer growth inhibition and inhibitory effects on the metastasis rate and the number of metastasized colonies from primary tumor to lung.

These findings indicated that administration of the antibody against a peptide region encoded by Exon-17 specifically found in PN-1 (i.e., anti-Exon-17 polyclonal antibody or anti-Exon-17 monoclonal antibody) allows inhibition of the progress of cancer condition, leading to accomplishment of the present invention.

Namely, the present invention provides a pharmaceutical composition for cancer treatment, which comprises an antibody against periostin, particularly an antibody against a peptide region encoded by Exon-17.

Namely, the present invention includes the following aspects.

(1) An antibody against a periostin isoform having anti-cell adhesive activity, specifically recognizing a site responsible for anti-cell adhesion of periostin, and having ability to neutralize anti-cell adhesive activity of periostin.

(2) The antibody as defined in (1), wherein the site for responsible for anti-cell adhesion of periostin is the amino acid sequence encoded by Exon-17 or by a part thereof.

(3) The antibody as defined in (2), wherein the amino acid sequence encoded by Exon-17 or by a part thereof is one of the amino acid sequences selected from the group of SEQ IDs NO: 3, 4, 21, 22, 23, 24, 26 and 34.

(4) The antibody as defined in (3), wherein the amino acid sequence is the amino acid sequence of SEQ IDs NO: 3, 4, or 21.

(5) The antibody as defined in any one of (1) to (4), which is a monoclonal antibody.

(6) An antibody as defined in (5) produced by a hybridoma cell line FERM BP-10718.

(7) A hybridoma obtainable by a process comprising steps of:
immunizing a mammal with a peptide having one of the amino acid sequences selected from the group of SEQ IDs NO: 3, 4, and 21 or a peptide introduced cysteine residues into the N-terminus thereof; and
fusing an antibody-producing cell of the mammal with a myeloma cell.

(8) A hybridoma cell line FERM BP-10718.

(9) A method for producing an antibody as defined in (5), comprising steps of:
immunizing a mammal with a peptide having one of the amino acid sequences selected from the group of SEQ IDs NO: 3, 4, and 21 or a peptide introduced cysteine residues into the N-terminus thereof;
fusing an antibody-producing cell of the mammal with a myeloma cell; and
culturing the obtained hybridoma.

(10) The method as defined in (9), wherein the hybridoma is a hybridoma cell line FERM BP-10718.

(11) A pharmaceutical composition comprising the antibody as defined in any one of (1) to (6).

(12) A method for preventing or treating a disease in which a periostin isoform having anti-cell adhesive activity is involved, comprising administering the antibody as defined in any one of (1) to (6) to a patient.

(13) The method as defined in (12), wherein the disease is heart failure, myocardial infarction, heart dilation, cardiac hypertrophy, cardiac fibrosis, cardiomyopathy, myocarditis, valvular disease, cancer, aneurysm, arteriosclerosis, central neurodegenerative disease, renal disease, rheumatoid arthritis, osteoporosis, pulmonary emphysema, pulmonary hypertension, chronic obstructive pulmonary disease (COPD), nephritis, pancreatitis, hepatitis, hepatic fibrosis or pulmonary fibrosis.

(14) The method as defined in (13), wherein the disease is cancer.

(15) The method as defined in (14), wherein cancer is prevented or treated by inhibiting cancer metastasis.

(16) The method as defined in (14), wherein cancer is prevented or treated by inhibiting the growth of primary tumor.

(17) The method as defined in (14), wherein cancer is prevented or treated by inhibiting the bone invasion of cancer or bone destruction caused by bone invasion of cancer.

(18) The method as defined in any one of (14) to (17), wherein the cancer is malignant melanoma or breast cancer.

(19) A method for diagnosing a disease in which a periostin isoform having anti-cell adhesive activity is involved, comprising measuring the amount of the periostin isoform in a biological sample by using the antibody as defined in any one of (1) to (6).

(20) The method as defined in (19) wherein the antibody is a labeled antibody.

(21) The method as defined in (19) or (20), wherein the disease is heart failure, myocardial infarction, heart dilation, cardiac hypertrophy, cardiac fibrosis, cardiomyopathy, myocarditis, valvular disease, cancer, aneurysm, arteriosclerosis, central neurodegenerative disease, renal disease, rheumatoid arthritis, osteoporosis, pulmonary emphysema, pulmonary hypertension, chronic obstructive pulmonary disease (COPD), nephritis, pancreatitis, hepatitis, hepatic fibrosis or pulmonary fibrosis.

(22) The method as defined in (21), wherein the disease is cancer.

(23) The method of as defined in (22), wherein cancer is prevented or treated by inhibiting cancer metastasis.

(24) The method as defined in (22), wherein cancer is prevented or treated by inhibiting the growth of primary tumor.

(25) The method as defined in (22), wherein cancer is prevented or treated by inhibiting the bone invasion of cancer or bone destruction caused by bone invasion of cancer.

(26) The method as defined in any one of (22) to (25), wherein the cancer is malignant melanoma or breast cancer.

(27) A method for detecting or quantifying a periostin isoform having anti-cell adhesive activity in a sample by using the antibody as defined in any one of (1) to (6).

(28) A diagnostic reagent for a disease in which a periostin isoform having anti-cell adhesive activity is involved, comprising the antibody as defined in any one of (1) to (6).

(29) The diagnostic reagent as defined in (28), wherein the disease is heart failure, myocardial infarction, heart dilation, cardiac hypertrophy, cardiac fibrosis, cardiomyopathy, myocarditis, valvular disease, cancer, aneurysm, arteriosclerosis, central neurodegenerative disease, renal disease, rheumatoid arthritis, osteoporosis, pulmonary emphysema, pulmonary hypertension, chronic obstructive pulmonary disease (COPD), nephritis, pancreatitis, hepatitis, hepatic fibrosis or pulmonary fibrosis.

BRIEF EXPLANATION OF THE DRAWINGS

FIG. 4-1 is a diagram showing assay results of the inhibition of heart dilation by anti-rat Exon-17 peptide antibody 4 weeks after the preparation of acute myocardial infarction models (Example 4: anterior wall thickness, posterior wall thickness).

FIG. 4-2 is a diagram showing assay results of the inhibition of heart dilation by anti-rat Exon-17 peptide antibody 4 weeks after the preparation of acute myocardial infarction models (Example 4: end-diastolic inner diameter, end-systolic inner diameter, heart function).

FIG. 4-3 is a diagram showing assay results of the inhibition of heart dilation by anti-rat Exon-17 peptide antibody 4 weeks after the preparation of acute myocardial infarction models (Example 4: heart rate, infarction area).

FIG. 5-1 is a diagram showing assay results of the inhibition of heart dilation by anti-rat Exon-17 peptide antibody 8 weeks after the preparation of acute myocardial infarction models (Example 4: anterior wall thickness, posterior wall thickness).

FIG. 5-2 is a diagram showing assay results of the inhibition of heart dilation by anti-rat Exon-17 peptide antibody 8 weeks after the preparation of acute myocardial infarction models (Example 4: end-diastolic inner diameter, end-systolic inner diameter, heart function).

FIG. 5-3 is a diagram showing assay results of the inhibition of heart dilation by anti-rat Exon-17 peptide antibody 8 weeks after the preparation of acute myocardial infarction models (Example 4: heart rate, infarction area).

FIG. 6-1 is a diagram showing hemodynamics of model rats treated with anti-rat Exon-17 peptide antibody (Example 4: LVP, heart rate).

FIG. 6-2 is a diagram showing hemodynamics of model rats treated with anti-rat Exon-17 peptide antibody (Example 4: (+) dP/dt, (−) dP/dt).

FIG. 6-3 is a diagram showing hemodynamics of model rats treated with anti-rat Exon-17 peptide antibody (Example 4: SBP, DBP, LVEDP).

FIG. 9-1 is a diagram showing the results of gene expression analysis of model rats treated with anti-rat Exon-17 peptide antibody (Example 4: G3PDH).

FIG. 9-2 is a diagram showing the results of gene expression analysis of model rats treated with anti-rat Exon-17 peptide antibody (Example 4: ET-1/G3, Angiotensinogen/G3).

FIG. 9-3 is a diagram showing the results of gene expression analysis of model rats treated with anti-rat Exon-17 peptide antibody (Example 4: α-MHC/G3, β-MHC/G3).

FIG. 9-4 is a diagram showing the results of gene expression analysis of model rats treated with anti-rat Exon-17 peptide antibody (Example 4: Col-I/G3, Col-III/G3).

FIG. 9-5 is a diagram showing the results of gene expression analysis of model rats treated with anti-rat Exon-17 peptide antibody (Example 4: TGF-β/G3, TNF-α/G3).

FIG. 12-1 is a diagram showing assay results of the inhibition of heart dilation by anti-human Exon-17 monoclonal antibody 4 weeks after the preparation of acute myocardial infarction models (Example 17: anterior wall thickness, posterior wall thickness).

FIG. 12-2 is a diagram showing assay results of the inhibition of heart dilation by anti-human Exon-17 monoclonal antibody 4 weeks after the preparation of acute myocardial infarction models (Example 17: end-diastolic inner diameter, end-systolic inner diameter, heart function).

FIG. 12-3 is a diagram showing assay results of the inhibition of heart dilation by anti-human Exon-17 monoclonal antibody 4 weeks after the preparation of acute myocardial infarction models (Example 17: heart rate, infarction area).

THE MOST PREFERRED EMBODIMENTS OF THE INVENTION

Figure 1:
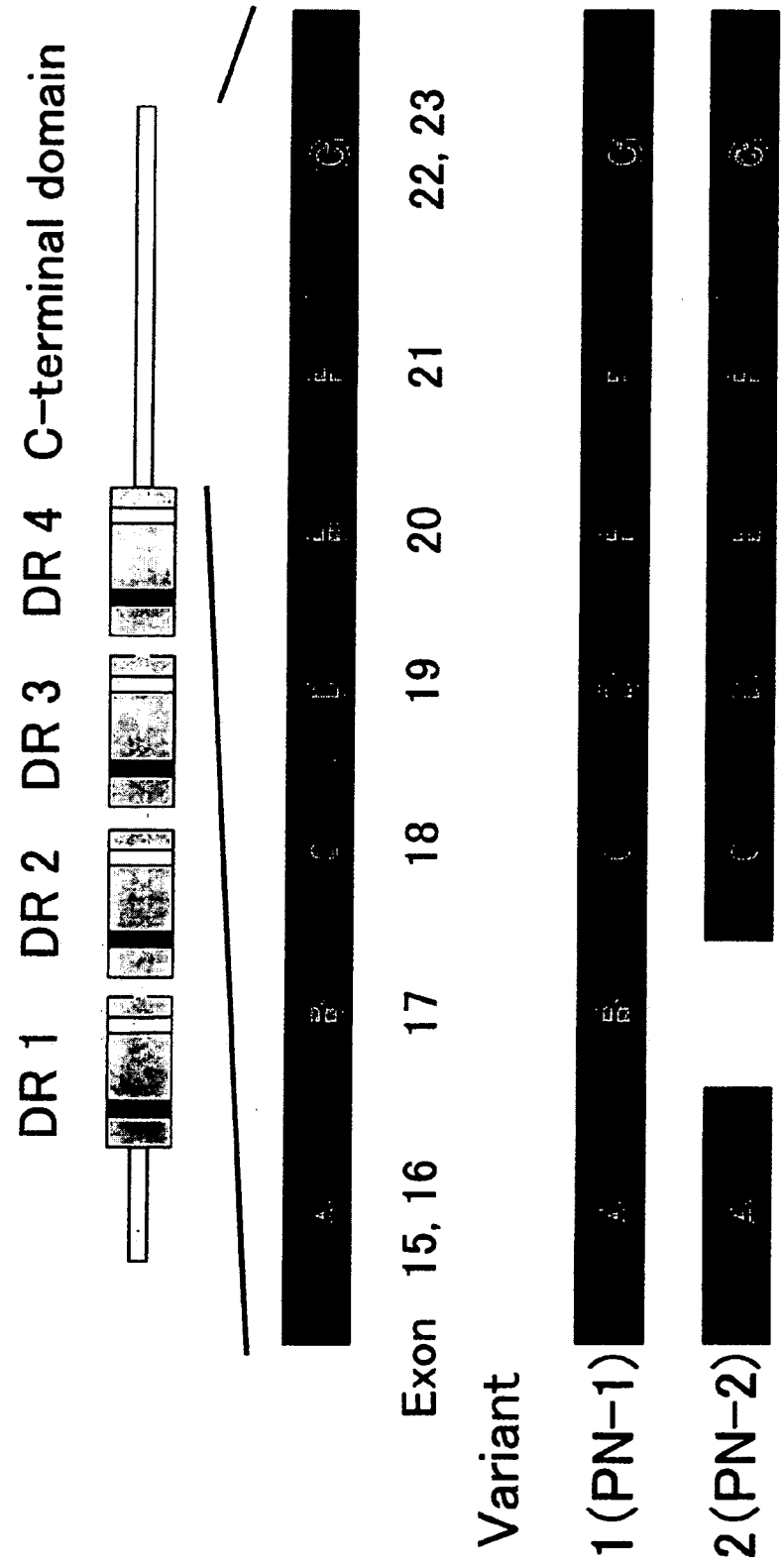
FIG. 1 is a schematic diagram showing a rat periostin splicing variant.

In an embodiment, the present invention provides an antibody against a periostin isoform having anti-cell adhesive activity. Periostin here is one of extracellular matrix proteins and is known to include some splice variants, some of which are specifically expressed in the heart during heart failure or the like. In the present invention, antibodies can be used as substances (i.e., as inhibitors) for inhibiting functions of a periostin splicing variant specifically expressed in the heart during heart failure or the like because of their high specificity, safety for humans and for other reasons. In the present invention, an antibody can be prepared against an antigen composed of a chemically synthesized peptide consisting of an amino acid sequence encoded by the Exon-17 region of the C-terminal domain at which a splice variant is formed, though such a peptide can also be obtained from any source by enzymatic digestion of periostin protein or by genetic engineering techniques.

In the present invention, the expression "having anti-cell adhesive activity" means having the action of separating or eliminating adhered cells. Likewise, the expression "having no anti-cell adhesive activity" means that adhered cells are neither detached nor peeled off. In this case, the cells maintain their adhered state. The presence or absence of anti-cell adhesive activity may be determined by culturing cells (e.g., heart fibroblasts) in a culture plate to allow the cells to adhere to the culture plate, adding an assay sample and further culturing the cells, washing the plate to remove separated cells, staining the remaining cells, and confirming the state of the adhered cells.

In the present invention, periostin isoforms having anti-cell adhesive activity preferably include periostin isoforms consisting of an amino acid sequence of SEQ ID NO: 1 (rat periostin PN-1, 838 amino acids), SEQ ID NO: 2 (human periostin PN-1, 836 amino acids having an N-terminal signal sequence shorter by 2 amino acids than that of rat periostin), or SEQ ID NO: 8 (mouse periostin PN-1).

Regions responsible for the anti-cell adhesive activity of periostin include, e.g., the site of Exon-17. Specific examples include an amino acid residue part shown in SEQ ID NO: 3 of a periostin isoform having an amino acid sequence shown in SEQ ID NO: 1 (672-698 amino acids of SEQ ID NO: 1), an amino acid residue part shown in SEQ ID NO: 4 of a periostin isoform having an amino acid sequence shown in SEQ ID NO: 2 (670-696 amino acids of SEQ ID NO: 2), and an amino acid residue part shown in SEQ ID NO: 21 of a periostin isoform having an amino acid sequence shown in SEQ ID NO: 8 (672-698 amino acids of SEQ ID NO: 8). Further examples include an amino acid sequence shown in SEQ ID NO: 22, SEQ ID NO: 23, SEQ ID NO: 24 or SEQ ID NO: 26, as well as SEQ ID NO: 34 (an amino acid sequence shown in SEQ ID NO: 22 or SEQ ID NO: 23, as well as an amino acid sequence consisting of the N-terminal 1st to 6th amino acid residues of SEQ ID NO: 22 or SEQ ID NO: 23).

The expression "neutralizing the anti-cell adhesive activity of periostin" means that the action or activity of the above "region responsible for the anti-cell adhesive activity of periostin" is inhibited, and more specifically means that the action or activity of periostin is inhibited using, for example, an antibody capable of specifically recognizing the above site responsible for anti-cell adhesive activity.

In an embodiment, antibodies of the present invention are monoclonal antibodies and polyclonal antibodies obtained by using the antigens as described above. The "monoclonal antibodies" here refer to any monoclonal antibody showing reactivity against the antigens described above, and the "monoclonal antibodies" include natural antibodies obtained by immunizing mammals such as mice, rats, hamsters, guinea pigs or rabbits with the antigens, chimeric monoclonal antibodies (chimeric antibodies) and humanized monoclonal antibodies (humanized antibodies; CDR-grafted antibodies) that can be prepared by using genetic recombination techniques, as well as human monoclonal antibodies (human antibodies) that can be prepared by using human antibody-producing transgenic animals or the like. Antibodies of the present invention include monoclonal antibodies having any isotype such as IgG (IgG1, IgG2, IgG3, IgG4), IgM, IgA, IgD or IgE, preferably IgG (IgG1, IgG2, IgG3, IgG4) or IgM.

When the peptides described above are to be used as antigens, they can be used alone as antigens but also can be used for immunization by adsorption to a macromolecular material such as polyvinyl pyrrolidone, latex or polymethyl methacrylate, or coupling to a carrier protein such as KLH (Keyhole Limpet Hemocyanin) or BSA (bovine serum albumin), and any method can be used. Generally, the peptides may preferably be coupled to a carrier protein by known methods (e.g., "New series of Development of Drugs, Vol. 14, Hirokawa Publishing Co., 1991"). The peptides are coupled to a carrier protein via cysteine residues introduced into the C- or N-terminus of the peptides so that the peptides have directionality. Crosslinkers commonly used in the field of the art can be used so long as they are suitable for this purpose. Suitable crosslinkers include succinimidyl-4-(N-maleimidomethyl) cyclohexane-1-carboxylate (hereinafter abbreviated as "SMCC") or 3-maleimidobenzoic acid-N-hydroxysuccinimide ester (MBS). Monoclonal antibodies are prepared by culturing hybridomas prepared by the cell fusion method of Kohler and Milstein (G. Kohler et al Nature (1975) 256, 495-7) to secrete the antibodies and isolating them from the cultures. That is, a mammal is immunized with a peptide having an amino acid sequence encoded by Exon-17 or the like and then antibody-producing cells of this animal are fused to myeloma cells to give hybridomas. Search for hybridomas producing antibodies binding to Exon-17 is performed by e.g., an enzyme immunoassay (hereinafter abbreviated as "ELISA") for hybridoma supernatants using a microplate on which the antigen has been immobilized. Animals to be immunized are not specifically limited, but include various mammals such as mice, rats, guinea pigs, rabbits, sheep, goats, cats, dogs, etc. Among the animals listed above, Balb/c mice are generally used for preparation of monoclonal antibodies because of ease of handling or for other reasons, but other strains of mice can also be used. The concentration of the antigen used for immunization here is selected to form sufficient amounts of antigenically stimulated lymphocytes. Preferably, 1-100 µg of an antigen is diluted to an appropriate concentration with physiological saline or the like and suspended in Freund's complete adjuvant or Freund's incomplete adjuvant or the like, and the suspension is administered to an animal by intraperitoneal or subcutaneous injection or other means. Administration is performed once to several times every 2-4 weeks. The final immunization is normally performed by administering a solution of 1-100 µg of the antigen in physiological saline by intravenous or subcutaneous injection or other means. Several days after the final immunization, antibody-producing cells such as lymphocytes, preferably spleen cells or lymph node cells, are removed from the immunized animal for cell fusion. Cell fusion using spleen cells as antibody-producing cells is explained below, though antibody-producing cells other than spleen cells can also be used for cell fusion. Spleen cells prepared from the spleen aseptically removed 3-4 days after the final immunization are fused to appropriate myeloma cells in the presence of a fusion promoter. The myeloma cells used for fusion may be derived from mammals, but generally those derived from the same species as the animal used for immunization. Various cell lines are already known, for example, SP2/0-Ag14(SP2) [Nature, 276, 269 (1978)], NS-1-Ag4/1(NS-1), P3-X63Ag8U.1(P3U1) [Curr. Top. Microbiol. Immunol. 81, 1-7 (1978): available from ATCC under ATCC No. CRL-1597], P3-NS1-1-Ag4-1, P3-X63Ag8(P3), F0, X63Ag8.653(X63.653), 210.RCY3.Ag1.2.3, S194/5XXO.BU1, SKO-007, GM15006TG-A12 and the like are preferably used for mice, and Y3.Ag1.2.3 and the like are preferably used for rats. Preferred fusion promoters include polyethylene glycol (PEG) having a molecular weight of 1000-6000 and Sendai virus (HVJ). Generally, the ratio of spleen cells and myeloma cells during fusion is preferably 10:1-2:1.

Hybridomas can be separated from fused cells by culturing of a mixture of unfused spleen cells, unfused myeloma cells and fused cells in a selective medium inhibiting the survival of unfused myeloma cells for an appropriate period until unfused cells die (about 1 week). The selective medium may be e.g., HAT medium (medium containing hypoxanthine, aminopterin and thymidine). In this selective medium, unfused myeloma cells die, and unfused spleen cells die after a certain period of time (after about 1 week) because they are non-tumorous cells, so that hybridomas can be obtained by selecting viable cells. Hybridomas producing desired antibodies can be obtained by searching of strains producing the desired antibodies and cloning of the strains to prepare monoclonal antibodies by standard limiting dilution. Thus obtained hybridomas producing monoclonal antibodies of the present invention can grow in media suitable for their growth and can be readily stored in deep freezers or liquid nitrogen. Thus obtained hybridomas can produce antibodies by growing them in nutrient media or in the abdominal cavity of a mammal, and the produced antibodies can be purified from culture supernatants or the ascites fluid or serum of the mammal. As an example of the hybridomas of the present invention, a hybridoma can be used that was deposited, pursuant to the Budapest Treaty, under FERM BP-10718 on Nov. 1, 2006 with the International Patent Organism Depositary, the National Institute of Advanced Industrial Science and Technology, AIST Tsukuba Central 6, 1-1, Higashi 1-chome, Tsukuba-shi, Ibaraki-Ken 305-8566, Japan. Purification of the antibodies can be performed by standard isolation/purification methods such as centrifugation, dialysis, salting out with ammonium sulfate or the like, ion exchange chromatography using a DEAE column or the like, gel filtration, affinity chromatography, etc. The isotypes and subclasses of thus obtained monoclonal antibodies can be determined using an identification method such as Ouchterlony assay, ELISA, or RIA. Ouchterlony assay is convenient but requires a concentration operation if the monoclonal antibody concentration is low. When ELISA or RIA is used, however, the isotypes and subclasses of the monoclonal antibodies can be identified by direct reaction of the culture supernatant with an antigen-adsorbed solid phase and by use of antibodies corresponding to various immunoglobulin isotypes and subclasses as secondary antibodies. More convenient methods employ commercially available identification kits (e.g., Mouse Typer kit; Bio-Rad) or the like. The quantification of protein can be performed by the Folin-Lowry method and calculation from the absorbance at 280 nm [1.4 (OD280)=1 mg/ml immunoglobulin]. Thus obtained monoclonal antibodies of the present invention specifically recognize an amino acid sequence shown in SEQ ID NO: 1 or SEQ ID NO: 2, an amino acid sequence shown in SEQ ID NO: 3 or SEQ ID NO: 4, a periostin isoform (PN-1) having an amino acid sequence shown in SEQ ID NO: 34, a peptide consisting of an amino acid sequence shown in SEQ ID NO: 3 or SEQ ID NO: 4, or a peptide having an amino acid sequence shown in SEQ ID NO: 34. Preferably, the monoclonal antibodies of the present invention can specifically recognize and bind to a peptide consisting of the amino acid sequence YTTKIITKVV (SEQ ID NO: 26), i.e., a peptide consisting of an amino acid sequence covering from the −1st tyrosine to the 9th valine from the N-terminus of the amino acid sequence of the human periostin Exon-17 peptide chain (SEQ ID NO: 4), and a peptide consisting of an amino acid sequence covering from the 669th tyrosine to the 679th valine from the N-terminus of the amino acid sequence of human periostin PN-1 (SEQ ID NO: 2). Namely, the monoclonal antibodies of the present invention can specifically recognize an amino acid sequence site (TTKIITKVV; SEQ ID NO: 22), or a part thereof, which covers from the N-terminal threonine to the 9th valine of the amino acid sequence of the human periostin Exon-17 peptide chain (SEQ ID NO: 4). More preferably, the monoclonal antibodies of the present invention can recognize and bind to a peptide comprising alanine substitutions at the 1st and the 8-10th amino acids from the N-terminus of a peptide consisting of an amino acid sequence (YTTKIITKVV; SEQ ID NO: 26) covering from the −1st tyrosine to the 9th valine from the N-terminus of the human periostin Exon-17 peptide chain (SEQ ID NO: 4). Namely, the monoclonal antibodies of the present invention can specifically recognize at least an amino acid sequence site (SEQ ID NO: 34), or a part thereof, which covers from the 1st threonine to the 6th threonine from the N-terminus of the amino acid sequence of the human periostin Exon-17 peptide chain (SEQ ID NO: 4) or the amino acid sequence of the rat periostin Exon-17 peptide chain (SEQ ID NO: 3). Moreover, the monoclonal antibodies of the present invention have the activity of suppressing or inhibiting the anti-cell adhesive properties of human periostin-1 protein, i.e., neutralizing the anti-cell adhesive properties of human periostin-1 protein. Furthermore, the monoclonal antibodies of the present invention can suppress the heart dilation, cardiac hypertrophy and cardiac fibrosis induced during heart failure or the like to improve heart function. Moreover, the monoclonal antibodies for use in the present invention have the activity of suppressing or inhibiting the PN-1 protein's effects of inhibiting cancer cell adhesion and separating adhered cells, i.e., the activity of neutralizing the PN-1 protein's effects of inhibiting cancer cell adhesion and separating adhered cells. The monoclonal antibodies for use in the present invention further have inhibitory activities on the growth of primary tumor, the bone invasion of cancer cells, the bone destruction caused by bone invasion of cancer cells, and metastasis.

When polyclonal antibodies are used as antibodies of the present invention, the polyclonal antibodies can be obtained by standard methods such as the method described in "New Lecture on Biochemical Experiments, 12, edited by the Japanese Biochemical Society, Tokyo Kagaku Dozin, 1992". Animals to be immunized are not specifically limited, but include horses, goats, sheep, rabbits, guinea pigs, mice, chickens, etc. When a rabbit is to be immunized, an antigen is diluted to an appropriate concentration with physiological saline or the like and suspended in Freund's complete adjuvant, Freund's incomplete adjuvant or aluminum hydroxide adjuvant or the like, and the suspension is injected at a dose of 10-1000 μg per animal followed by 1-3 booster injections after 2-4 weeks to give antisera. Multi-site subcutaneous injection is preferred. Preparation of polyclonal antibodies from antisera can be performed by the method as described for the purification of monoclonal antibodies. Thus obtained polyclonal antibodies of the present invention specifically recognize an amino acid sequence shown in SEQ ID NO: 1 or SEQ ID NO: 2, an amino acid sequence shown in SEQ ID NO: 3 or SEQ ID NO: 4, a periostin isoform (PN-1) having an amino acid sequence shown in SEQ ID NO: 34, a peptide consisting of an amino acid sequence shown in SEQ ID NO: 3 or SEQ ID NO: 4, or a peptide having an amino acid sequence shown in SEQ ID NO: 34.

Preferably, the polyclonal antibodies of the present invention can specifically recognize and bind to a peptide consisting of the amino acid sequence YTTKIITKVV (SEQ ID NO: 26), i.e., a peptide consisting of an amino acid sequence covering from the −1st tyrosine to the 9th valine from the N-terminus of the amino acid sequence of the human periostin Exon-17 peptide chain (SEQ ID NO: 4), and a peptide consisting of an amino acid sequence covering from the 669th tyrosine to the 679th valine from the N-terminus of the amino acid sequence of human periostin PN-1 (SEQ ID NO: 2). Namely, the polyclonal antibodies of the present invention can specifically recognize an amino acid sequence site (TTKIITKVV; SEQ ID NO: 22), or a part thereof, which covers from the N-terminal threonine to the 9th valine of the amino acid sequence of the human periostin Exon-17 peptide chain (SEQ ID NO: 4). More preferably, the polyclonal antibodies of the present invention can recognize and bind to a peptide comprising alanine substitutions at the 1st and the 8-10th amino acids from the N-terminus of a peptide consisting of an amino acid sequence (YTTKIITKVV; SEQ ID NO: 26) covering from the −1st tyrosine to the 9th valine from the N-terminus of the human periostin Exon-17 peptide chain (SEQ ID NO: 4) Namely, the polyclonal antibodies of the present invention can specifically recognize at least an amino acid sequence site (SEQ ID NO: 34), or a part thereof, which covers from the 1st threonine to the 6th threonine from the N-terminus of the amino acid sequence of the human periostin Exon-17 peptide chain (SEQ ID NO: 4) or the amino acid sequence of the rat periostin Exon-17 peptide chain (SEQ ID NO: 3). Moreover, the polyclonal antibodies of the present invention have the activity of suppressing or inhibiting the anti-cell adhesive properties of human periostin PN-1 protein, i.e., neutralizing the anti-cell adhesive properties of human periostin PN-1 protein. Furthermore, the polyclonal antibodies of the present invention can suppress the heart dilation, cardiac hypertrophy and cardiac fibrosis induced during heart failure or the like to improve heart function. Moreover, the polyclonal antibodies for use in the present invention have the activity of suppressing or inhibiting the PN-1 protein's activity of inhibiting cancer cell adhesion and separating adhered cells, i.e., the activity of neutralizing the PN-1 protein's activity of inhibiting cancer cell adhesion and separating adhered cells. The polyclonal antibodies for use in the present invention further have inhibitory activities on the growth of primary tumor, the bone invasion of cancer cells, the bone destruction caused by bone invasion of cancer cells, and metastasis of cancer cells.

Preparation of Humanized Antibodies

Immunoglobulin G (hereinafter simply referred to as "IgG") consists of two light polypeptide chains having a molecular weight of about 23000 (hereinafter referred to as "light chain") and two heavy polypeptide chains having a molecular weight of about 50000 (hereinafter referred to as "heavy chain"). The heavy and light chains both have a repeating structure of conserved amino acid sequence regions consisting of about 110 residues, which constitute a basic unit of three-dimensional structure of IgG (hereinafter referred to as "domain"). The heavy and light chains consist of 4 and 2 successive domains, respectively. In both of the heavy and light chains, the amino acid sequence of the amino terminal domain is more variable between antibody molecules than that of the other domains, and this domain is called variable domain (hereinafter referred to as "V domain"). At the amino terminus of IgG, the V domains of the heavy and light chains are complementarily associated to form a variable region. In contrast, the remaining domains collectively form a constant region. The constant region has a sequence characteristic of each animal species, e.g., the constant region of mouse IgG differs from the constant region of human IgG so that mouse IgG is recognized as foreign matter by the human immune system, resulting in a Human Anti Mouse Antibody (hereinafter referred to as "HAMA") response (Schroff R W. et al. Cancer Res. (1985) 45, 879-85). Thus, mouse antibodies cannot be repeatedly administered to humans. In order to administer such antibodies to humans, the antibody molecules must be modified to prevent HAMA response while maintaining the specificity of the antibodies. According to the results of X-ray crystallography, such a domain is generally in the form of an elliptic cylindrical structure formed of two antiparallel beta sheets consisting of 3 to 5 beta-chains. In the variable region, three loops for each of the V domains of the heavy and light chains are assembled to form an antigen-binding site. These loops are called complementarity determining regions (hereinafter referred to as "CDRs"), which are most variable in amino acid sequence. The remaining parts of the variable region other than the CDRs serve to maintain the structures of the CDRs and are called "framework". Kabatt et al. collected a number of primary sequences of heavy and light chain variable regions and prepared a table classifying the primary sequences into CDRs and frameworks on the basis of sequence conservation (Kabatt et al. SEQUENCES OF IMMUNOLOGICAL INTEREST, 5th edition, NIH publication, No. 91-3242, E.A.). The frameworks were further classified into a plurality of subgroups having common amino acid sequence patterns. The presence of a consensus framework between human and mouse sequences was also found. Such studies on structural features of IgG led to the development of the processes for preparing humanized antibodies described below. At an early stage of the studies, chimeric antibodies having a variable region from a mouse antibody fused to a constant region from a human antibody were proposed (Morrison S L. et al Proc Natl Acad Sci USA. (1984) 81, 6851-5). However, such chimeric antibodies may induce a HAMA response, especially when they are administered for a long term, because they still contain many non-human amino acid residues (Begent et al., Br. J. Cancer, (1990) 62, 487).

A method for further reducing amino acid residues derived from a non-human mammal that may induce a HAMA response to humans by transferring only the CDRs into a human antibody was proposed (Peter T et al. Nature, (1986) 321, 522-5), but grafting of only the CDRs was normally insufficient to maintain immunoglobulin activity against the antigen. On the other hand, Chothia et al. used X-ray crystallographic data in 1987 to find that (a) the amino acid sequences of the CDRs contain a site directly binding to the antigen and a site maintaining the structures of the CDRs, and possible three-dimensional structures of the CDRs are classified into multiple typical patterns (canonical structures), and that (b) the classes of the canonical structures are determined by not only the CDRs but also the types of amino acids at specific locations on the framework (Chothia C. et al. J. Mol. Biol, (1987) 196, 901-17). Based on this finding, a document suggested that when CDR grafting is used, amino acid residues on a part of the framework should also be grafted into a human antibody in addition to the CDR sequences (JPA No. HEI-4-502408). Generally, an antibody derived from a non-human mammal having CDRs to be grafted is defined as "donor", and a human antibody into which the CDRs are grafted is defined as "acceptor", and considerations in CDR grafting are to conserve the structures of the CDRs to the extent possible to maintain the activity of the immunoglobulin molecule. To achieve this object, two points should be kept in mind, i.e. (a) which subgroup of acceptor should be selected, and (b) which amino acid residue should be selected from the framework of the donor.

Queen et al. proposed methods for designing immunoglobulins wherein an amino acid residue in the framework of a donor is grafted into an acceptor in addition to the CDR sequences when at least one of the following criteria is satisfied (JPA No. HEI-4-502408):
  (a) the amino acid in the framework region of the acceptor is rare for that position and the corresponding amino acid in the donor is common for that position;
  (b) the amino acid is immediately adjacent to one of the CDRS; or
  (c) the amino acid is predicted to have a side chain atom within about 3 angstroms of the CDRs in a three-dimensional immunoglobulin model and to be capable of interacting with the antigen or with the CDRs of the humanized antibody.

The DNA encoding the heavy or light chain of an anti-Exon-17 monoclonal antibody of the present invention can be obtained by preparation of mRNA from hybridoma cells producing the anti-Exon-17 monoclonal antibody, conversion of the mRNA into cDNA by reverse transcriptase and then isolation of the DNA encoding the heavy or light chain of the antibody.

Preparation of Human Antibodies

As used herein, the "human antibody" or "human immunoglobulin" means an immunoglobulin in which all the regions constituting the immunoglobulin including heavy chain variable regions (VH) and heavy chain constant regions (CH) as well as light chain variable regions (VL) and light chain constant regions (CL) are derived from genes encoding a human immunoglobulin. In other words, it means an antibody in which the heavy chain is derived from a human immunoglobulin heavy chain gene and the light chain is derived from a human immunoglobulin light chain gene, Human antibodies can be prepared by standard methods, e.g., by immunization of a transgenic animal prepared by integration of at least a human immunoglobulin gene into the locus of a non-human mammal such as a mouse with an antigen, in the same manner as described above for the preparation of monoclonal antibodies. For example, transgenic mice producing human antibodies can be prepared by the methods described in prior documents (Mendez M J et al. Nature Genetics (1997) 15, 146-56, Green L L et al. Nature Genetics (1994) 7, 13-21, JPA HEI-4-504365; International Publication No. WO94/25585; Nikkei Science, June, pp. 40-50, 1995; Nils Lonberg et al. Nature (1994) 368, 856-9, and JPA No. HEI-6-500233).

Antibodies used in the present invention are not limited to whole antibody molecules and may be antibody fragments or derivatives as long as they can neutralize the activity of a periostin isoform having anti-cell adhesive activity.

Antibody fragments include, for example, Fab, F(ab')$_2$, Fv, single chain antibody (scFv), disulfide-stabilized antibody (dsFv), a CDR-containing peptide, etc.

Among the antibody fragments of the present invention, Fab, F(ab')$_2$ and the like can be obtained by treating an antibody inhibiting the anti-cell adhesive activity of periostin with a proteolytic enzyme such as papain or pepsin, or alternatively, can be prepared by constructing a gene encoding the resulting antibody fragment and introducing this construct into an expression vector, followed by expression in an appropriate host cell.

Among the antibody fragments of the present invention, scFv can be prepared by linking together an H chain V region and an L chain V region from an antibody inhibiting the anti-cell adhesive activity of periostin by using an appropriate peptide linker or the like. Alternatively, scFv can be prepared by constructing a DNA segment encoding the entire sequences or desired amino acid sequences of a gene encoding an H chain or H chain V region from the above antibody and a gene encoding an L chain or L chain V region from the antibody, and introducing this construct into an expression vector, followed by expression in an appropriate host cell.

Among the antibody fragments of the present invention, dsFv is an antibody fragment in which polypeptides modified to replace one amino acid residue by a cysteine residue in both H and L chain V regions from an antibody inhibiting the anti-cell adhesive activity of periostin are linked together between these cysteine residues via a disulfide linkage. An amino acid residue to be replaced by a cysteine residue can be selected by stereostructural estimation of the antibody. dsFv can be prepared by constructing a DNA segment encoding the entire sequence or a desired amino acid sequence of a gene encoding the antibody fragment, and introducing this construct into an expression vector, followed by expression in an appropriate host cell.

Among the antibody fragments of the present invention, a CDR-containing peptide comprises at least one or more CDR regions selected from CDR regions in H or L chains of an antibody inhibiting the anti-cell adhesive activity of periostin. Also, multiple CDR regions may be linked together by techniques using an appropriate peptide linker or the like. The CDR-containing peptide may also be prepared by constructing a DNA segment encoding the entire sequence or a desired amino acid sequence of a gene encoding the peptide, and introducing this construct into an expression vector, followed by expression in an appropriate host cell. Alternatively, the CDR-containing peptide can also be prepared by chemical synthesis such as Fmoc or tBoc method.

In the present invention, it is also possible to use derivatives of the above antibodies or antibody fragments, which are modified to have a protein or low-molecular compound bound thereto. These modifications may be accomplished by known techniques.

In an embodiment, the antibodies, antibody fragments or derivatives of the present invention can be used to prevent or treat diseases in which a periostin isoform having anti-cell adhesive activity is involved. "Diseases in which a periostin isoform having anti-cell adhesive activity is involved" refer to diseases during which a gene of a periostin isoform having anti-cell adhesive activity is highly expressed and the production of a protein encoded by the gene is increased. They also refer to diseases whose pathology is exacerbated by an increase in the gene or protein. Such diseases in which a periostin isoform having anti-cell adhesive activity is involved are not specifically limited, but include heart failure, myocardial infarction, heart enlargement (dilation), cardiac hypertrophy, cardiac fibrosis, cardiomyopathy, myocarditis, valvular disease, cancers, aneurysms, arteriosclerosis, central neurodegenerative disease, renal diseases, rheumatoid arthritis, osteoporosis, pulmonary emphysema, pulmonary hypertension, chronic obstructive pulmonary disease (COPD), (acute and chronic) nephritis, (acute and chronic) pancreatitis, (acute and chronic) hepatitis, hepatic fibrosis or pulmonary fibrosis. Cancers to which the antibodies of the present invention can be applied include, but not limited to, cancers of breast, large intestine, lung, malignant melanoma, bone, pancreas, stomach, skin, uterus, ovary, rectum, colon, uterus, fallopian tube, esophagus, small intestine, thyroid, parathyroid, adrenal gland, prostate, bladder and kidney, especially cancers of breast, large intestine, lung and malignant melanoma.

The present invention also provides a diagnostic reagent for a disease (e.g., heart failure) in which a periostin isoform having anti-cell adhesive activity is involved, prepared by labeling of an antibody as described above with a marker. Markers that can be used here include enzymes, radioisotopes, fluorescent dyes, etc. The enzymes used here are not specifically limited so long as they satisfy criteria such as high turnover number, stability even after conjugation, and the ability to specifically react with their substrates to develop color, etc., and enzymes used in standard enzyme immunoassays (EIA) can be used. Examples of preferred enzymes include peroxidases, β-galactosidases, alkaline phosphatases, glucose oxidase, acetylcholine esterase, glucose-6-phosphate dehydrogenase, malate dehydrogenase, etc. Enzyme inhibitors and coenzymes and the like can also be used.

Conjugation of these enzymes and antibodies can be performed by known methods using crosslinkers such as maleimide compounds. Substrates that can be used are known materials, selected depending on the enzymes used. For example, when the enzyme used is a peroxidase, 3,3',5,5'-tetramethylbenzidine can be used, or when the enzyme used is an alkaline phosphatase, paranitrophenol or the like can be used. Radioisotopes that can be used as markers include those used in the standard radioimmunoassay (RIA) such as 125I and 3H. Fluorescent dyes that can be used are those used in the standard fluoroimmunoassay such as fluorescence isothiocyanate (FITC) and tetramethyl rhodamine isothiocyanate (TRITC). The present diagnostic reagent can also be used as immunohistological staining capable of specifically staining affected interstitial tissue of the heart. When it is labeled with a radioisotope, it can also be used to image the lesion during heart failure by internal administration.

The present invention also provides a method for detecting or quantifying a periostin isoform having anti-cell adhesive activity in a biological sample obtained by preparing serum from human or animal blood, i.e., in serum, comprising the use of the antibody, antibody fragment or derivative of the present invention. The present invention further provides a method for diagnosing a disease (e.g., heart failure) in which a periostin isoform having anti-cell adhesive activity is involved, comprising detection or quantification of the periostin isoform. In the present method, a periostin isoform having anti-cell adhesive activity can be detected by a so-called sandwich ELISA (Enzyme-linked immunosorbent assay). When the diagnostic kit of the present invention is used, a sample is initially contacted with a plate on which a primary anti-periostin antibody has been immobilized to form a complex, and a secondary anti-periostin antibody labeled with a marker is bound to this complex, and then the signal intensity of the marker in this ternary complex is measured, whereby a periostin isoform having anti-cell adhesive activity can be detected or quantified. In particular, since a periostin isoform having anti-cell adhesive activity is a splicing variant which is specifically expressed during the pathology of heart failure or the like, the pathology in heart failure or the like can be diagnosed by monitoring its production.

In this way, an antibody of the present invention can be used here as the secondary antibody by labeling of the antibody.

Pharmaceutical compositions comprising the antibodies, antibody fragments or derivatives of the present invention as active ingredients may be prepared using carriers and/or excipients or other additives, which are used in standard formulation techniques.

The active ingredients of the pharmaceutical compositions according to the present invention are preferably administered in admixture with known pharmacologically acceptable carriers, excipients, diluents or the like by any administration mode commonly used for pharmaceutical preparations, for example, by the oral or parenteral (e.g., intravenous, intramuscular or subcutaneous) route. For example, the pharmaceutical compositions of the present invention can be prepared by appropriately mixing the active ingredients with physiologically acceptable carriers, flavors, excipients, stabilizers, diluents, emulsifiers, solutions, suspensions, syrups or the like, and can be used in the form of tablets, powders, granules, solutions or the like. Additives which can be incorporated into tablets or the like include, for example, binders such as gelatin and lubricants such as corn starch. Tablets may also be coated with a sugar coating or a gastric or enteric film. In the dosage form of capsules, the above compositions can further comprise liquid carriers. Injectable sterile compositions can also be prepared by applying standard formulae. Injectable aqueous vehicles include isotonic solutions containing glucose and the like, which may be used in combination with appropriate solubilizers such as polyethylene glycol, etc. The compositions may also be incorporated with buffers, stabilizers, preservatives, antioxidants, soothing agents and the like. For oral administration, when the active ingredients are likely to be decomposed in the digestive tract, the compositions may be administered orally as formulations that are resistant to decomposition in the digestive tract, for example, as microcapsules encapsulating the active ingredients within liposomes. It is also possible to use other administration modes intended for absorption through mucous membranes other than the digestive tract, including rectal, intranasal, sublingual and transpulmonary routes. In this case, the compositions can be administered in the form of suppositories, nose drops, sublingual tablets, transpulmonary agents or the like.

When the pharmaceutical compositions of the present invention are used for therapeutic purposes, their dosage is set at a therapeutically effective dosage, which varies depending on, e.g., an age and a body weight of a subject to which the composition is to be administered, a severity of symptoms and a route of administration, and thus administration is determined on an individual basis. In general, the daily adult dosage for oral administration is about 0.1 to 1000 mg, given as a single dose or in divided doses. For continuous intravenous administration, the compositions can be administered in the range of 0.01 µg/kg/min to 1.0 µg/kg/min, desirably 0.025 µg/kg/min to 0.1 µg/kg/min.

Pharmaceutical Composition for Cancer Treatment

The present invention is also directed to a pharmaceutical composition for cancer treatment, which comprises an anti-periostin antibody recognizing a periostin splice variant having anti-cell adhesive properties (PN-1 protein).

The pharmaceutical composition of the present invention can be used for cancer treatment or diagnosis. Cancers to be treated or diagnosed by the present invention include, but not limited to, malignant melanoma, as well as cancers of breast, large intestine, lung, bone, pancreas, stomach, skin, uterus, ovary, rectum, colon, uterus, fallopian tube, esophagus, small intestine, thyroid, parathyroid, adrenal gland, prostate, bladder and kidney. The pharmaceutical composition of the present invention can be particularly applied to highly metastatic cancers such as malignant melanoma, breast cancer, large intestine cancer or lung cancer.

The pharmaceutical composition of the present invention has inhibitory effects on the growth of primary tumor, on the bone invasion of cancer cells, on the bone destruction caused by bone invasion of cancer cells, and on cancer metastasis. Thus, cancer treatment can be achieved by inhibiting the growth of primary tumor, the bone invasion of cancer cells, the bone destruction caused by bone invasion of cancer cells, or by inhibiting cancer metastasis.

The pharmaceutical composition of the present invention may be prepared using carriers and/or excipients or other additives, which are used in standard formulation techniques.

The antibody serving as an active ingredient in the pharmaceutical composition of the present invention is preferably administered in admixture with known pharmacologically acceptable carriers, excipients, diluents or the like by any administration mode commonly used for pharmaceutical preparations, especially antibody drugs, for example, via the intravenous, subcutaneous, intracutaneous, intramuscular, intraperitoneal or oral route.

The pharmaceutical composition of the present invention can be prepared by appropriately mixing the active ingredient with physiologically acceptable carriers, flavors, excipients, stabilizers, diluents, emulsifiers, solutions, suspensions, syrups or the like, and can be used in the form of tablets, powders, granules, solutions or the like. Additives which can be incorporated into tablets or the like include, for example, binders such as gelatin and lubricants such as corn starch. Tablets may also be coated with a sugar coating or a gastric or enteric film. In the dosage form of capsules, the above composition can further comprise liquid carriers. Injectable sterile compositions can also be prepared by applying standard formulae. Injectable aqueous vehicles include isotonic solutions containing glucose and the like, which may be used in combination with appropriate solubilizers such as polyethylene glycol, etc. The compositions may also be incorporated with buffers, stabilizers, preservatives, antioxidants, soothing agents and the like. For oral administration, when the active ingredient is likely to be decomposed in the digestive tract, the composition may be administered orally as a formulation that is resistant to decomposition in the digestive tract, for example, as microcapsules encapsulating the active ingredient within liposomes. It is also possible to use other administration modes intended for absorption through mucous membranes other than the digestive tract, including rectal, intranasal, sublingual and transpulmonary routes. In this case, the composition can be administered in the form of suppositories, nose drops, sublingual tablets, transpulmonary agents or the like.

When the pharmaceutical composition of the present invention is used for therapeutic purposes, its dosage is set at a therapeutically effective dosage, which varies depending on, e.g., an age and a body weight of a subject to which the composition is to be administered, a severity of symptoms and a route of administration, and thus administration is determined on an individual basis. In general, the daily adult dosage for oral administration is about 0.1 to 1000 mg, given as a single dose or in divided doses. For continuous intravenous administration, the composition can be administered in the range of 0.01 µg/kg/min to 1.0 µg/kg/min, desirably 0.025 µg/kg/min to 0.1 µg/kg/min.

Diagnostic Method

The present invention is also directed to a method for cancer diagnosis, which comprises measuring the amount of a periostin isoform having a peptide region encoded by Exon-17 in a biological sample, for example, a serum sample prepared from human or animal blood by using an antibody for use in the present invention. In the present method, a periostin isoform having a peptide region encoded by Exon-17 can be detected by a so-called sandwich ELISA (Enzyme-linked immunosorbent assay) When a diagnostic kit is used, a sample is initially contacted with a plate on which a primary antibody has been immobilized to form a complex, and a secondary antibody labeled with a marker is bound to this complex, and then the signal intensity of the marker in this ternary complex is measured, whereby a periostin isoform having a peptide region encoded by Exon-17 can be detected or quantified. In particular, since a periostin isoform having a peptide region encoded by Exon-17 is a splice variant which is highly expressed during the pathology of cancer or the like and is involved in primary tumor growth and cancer metastasis, the pathology in cancer or the like can be diagnosed by monitoring its production.

In this way, an antibody for use in the present invention can be used here as the secondary antibody by labeling of the antibody.

The following examples further illustrate the present invention in detail and specifically, without, however, thus limiting the invention.

EXAMPLES

Preparation Example 1

Search for Periostin by Subtraction 1-1 Preparation of Pathologic Model Rats of Heart Failure and Collection of Left Ventricular Samples Male Dahl salt-sensitive rats (Dahl-S) (Shimizu Laboratory Supplies) were raised on an 8% high salt diet from 6 weeks of age, and the left ventricle was collected from three animals each at cardiac hypertrophy stage (11 weeks of age) and heart failure stage (14 weeks of age).

1-2 Preparation of mRNA

Total RNA was prepared from about 500 mg of the left ventricle using ISOGEN (Nippon Gene) as instructed by the manufacturer. Then, mRNA was purified from about 40 µg of the combined total RNA from three animals each at cardiac hypertrophy stage and heart failure stage using Fast Track 2.0 Kit (Invitrogen) as instructed by the manufacturer to recover about 3 µg of mRNA at each stage.

1-3 cDNA Subtraction cDNA subtraction was performed using PCR-Select cDNA subtraction kit (Clontech) as instructed by the manufacturer. That is, cDNA was synthesized from 2 µg of each mRNA obtained in 1-2 above and digested with restriction enzyme RsaI. Then, subtraction hybridization was performed using the cDNA synthesized from the animals at 14 weeks of age as tester cDNA and the cDNA synthesized from the animals at 11 weeks of age as driver cDNA after 2 adapters included in the kit had been separately linked to the tester cDNA. Then, a cDNA fragment with altered expression level was specifically amplified by PCR using primers complementary to the adapters to give amplification product 1.

A similar subtraction operation was performed using the cDNA synthesized from the animals at 11 weeks of age as tester cDNA and the cDNA synthesized from the animals at 14 weeks of age as driver cDNA to give amplification product 2.

1-4 Dot Blot Screening

A. Preparation of Dot Blots

Amplification product 1 was TA cloned into a PCR II vector (Invitrogen) and clones having the insert fragment were selected. The insert fragment of each clone was amplified by PCR reaction, and then 1 µl each of the reaction solution was heat-treated and then dot-blotted on 2 nylon membrane filters (Boehringer) and fixed with a UV crosslinker (Stratagene).

B. Preparation of cDNA Probes

Amplification product 1 was digested with restriction enzymes RsaI and EaeI, SmaI to remove the adapters and subjected to random prime labeling with DIG-dUTP using DIG High Prime DNA labeling/detection kit II (Boehringer) as instructed by the manufacturer to prepare cDNA probe 1. Similarly, cDNA probe 2 was prepared from amplification product 2.

C. Screening

One of the dot blot membranes prepared in A above was hybridized with cDNA probe 1 and the other with cDNA probe 2. Specifically, hybridization was performed in DIG Easy Hyb solution at 42° C. overnight using DIG High Prime DNA labeling/detection kit II (Boehringer) as instructed by the manufacturer. The membranes were washed twice with 2×SSC, 0.1% SDS at room temperature for 5 minutes and twice with 0.1×SSC, 0.1% SDS at 68° C. for 15 minutes, and then reacted with alkaline phosphatase-labeled DIG antibodies in the blocking buffer included in the kit, and then CSPD ready-to use was added to advance chemiluminescence and X-ray film was exposed. Clones showing a stronger signal in cDNA probe 1 than cDNA probe 2 were selected as positive clones and sequenced.

1-5 Sequencing

The nucleotide sequences were determined by analysis on an automatic DNA sequencer model 373A (PE Applied Biosystems) using THERMO Sequenase™ II dye terminator cycle sequencing kit (Amersham Pharmacia). Thus obtained gene sequences were compared with sequences in the GenBank databank to reveal that one of the clones (SF014) was a gene having an 86% homology to mouse periostin (GenBank Accession No. D13664).

Preparation Example 2

Cloning of Rat Periostin cDNA

Rat periostin cDNA was isolated by screening 10 phage subpools of about 4000 clones (a total of about 40,000 clones) prepared from a rat aorta cDNA library (Clontech) inserted into λgt11 vector by PCR using primers (1) 5'-GTTCAT-TGAAGGTGGCGATGGTC-3' (SEQ ID NO: 15), and (2) 5'-GAGATAAAATCCCTGCATGGTCCT-3' (SEQ ID NO: 16) designed on the basis of the nucleotide sequence of SF014 to give 3 positive subpools. One of the subpools was screened by hybridization using the fragment amplified by PCR as a probe labeled with alkaline phosphatase using AlkPhos Direct™ (Amersham Pharmacia) to give one positive clone rat periostin #1. Its insert fragment was subcloned into the EcoRI site of pBluescript II (Stratagene) and the total nucleotide sequence was determined according to the method of Preparation example 1-5.

The resulting clone had a length of about 3 kb corresponding to nucleotide 292 to the 3' end of mouse periostin (GenBank Accession No. D13664), suggesting that it was a 5'-truncated clone.

Thus, SMART™ RACE cDNA Amplification Kit (Clontech) was used as instructed by the manufacturer to perform 5'-RACE reaction using rat aorta cDNA as a template and the primer (2) 5'-GAGATAAAATCCCTGCATGGTCCT-3' (SEQ ID NO: 16) and a primer (3) 5'-CACGGTCGATGACATGGACAACACC-31 (SEQ ID NO: 17) designed on the basis of the nucleotide sequence of rat periostin #1. The resulting PCR product was TA cloned into PCR II vector of Invitrogen to give a clone designated as rat periostin 5'RACE #1. The nucleotide sequence was determined according to the method of Preparation example 1-5.

The results showed that rat periostin 5'RACE #1 was a clone longer by about 300 bp than the initially obtained rat periostin #1 in the 5' direction with the 5' end being longer by 15 bp than the 5' end of mouse periostin (GenBank Accession No. D13664). Ten phage subpools of about 40,000 clones (a total of about 400,000 clones) prepared from the rat aorta cDNA library were screened by PCR using a primer (4) 5'-ACGGAGCTCAGGGCTGAAGATG-3' (SEQ ID NO: 18) designed on the basis of the nucleotide sequence of rat periostin 5'RACE #1 and the primer (3) 5'-CACGGTCGATGACATGGACAACACC-3' (SEQ ID NO: 17) to give 2 positive subpools. One of the subpools was screened by hybridization using the fragment amplified by PCR as a probe to give one positive clone designated as rat periostin #2. The insert fragment was subcloned into the EcoRI site of pBluescript II (Stratagene) and the nucleotide sequence was determined according to the method of Preparation example 1-5.

The resulting clone had a length of about 2.6 kb with the 5' end being the same as that of the clone obtained with 5'-RACE and the 3' end corresponding to up to nucleotide 2410 of mouse periostin (GenBank Accession No. D13664). The nucleotide sequence of rat periostin 5'RACE #1 previously obtained was exactly the same as the nucleotide sequence of the relevant region of rat periostin #2. The full length of rat periostin cDNA was completed by rat periostin #1 and rat periostin #2. The nucleotide sequence of this full-length cDNA and the amino acid sequence translated from this nucleotide sequence are shown as SEQ ID NOs: 6 and 1.

Preparation Example 3

Construction of a Myc-His-rat Periostin Fusion Protein Expression Vector

An expression vector having a Myc epitope and 6 histidine tags at the carboxyl terminus of the protein translated from the coding region of the rat periostin gene obtained in Preparation example 2, and having a CMV promoter, was prepared.

Initially, a fragment of about 500 bp obtained by digestion of rat periostin 5'RACE #1 obtained in Preparation example 2 with restriction enzymes EcoRI and HindIII and a fragment of about 2780 bp obtained by digestion of rat periostin #1 obtained in Preparation example 2 with restriction enzymes HindIII and HpaI were ligated to a vector fragment obtained by digesting pTracer-CMV2 vector (Invitrogen) with restriction enzymes EcoRI and EcoRV using a ligation kit (Takara Bio Inc.) to give a plasmid designated as pTracer-CMV2/rat periostin. Thus prepared pTracer-CMV2/rat periostin was digested with restriction enzymes EcoRI and SmaI to give a fragment of about 2330 bp containing the coding region of the rat periostin gene, and PCR was performed using rat periostin #1 obtained in Preparation example 2 as a template and primer (5) 5'-GACCCGGGAAGAACGCATCATC-3' (SEQ ID NO: 19) designed on the basis of the sequence of the template and primer (6) 5'-TGGGTGACCCTGAGAACGGCCTTCTCTTGATC-3' (SEQ ID NO: 20) designed to insert a BstEII site immediately before the stop codon of rat periostin and the amplification product was purified and then digested with restriction enzymes SmaI and BstEII to give a fragment of about 270 bp. These two fragments were ligated to a vector fragment obtained by digestion of an expression vector constructing plasmid pcDNA4/Myc-His/type C (Invitrogen) with restriction enzymes EcoRI and BstEII using a ligation kit (Takara Bio Inc.) to give a plasmid designated as pcDNA4/Myc-His/rat periostin. The total nucleotide sequence of the insert was confirmed by the method described in Preparation example 1-5.

Preparation Example 4

Construction of a Baculovirus Expression Vector

The plasmid pcDNA4/Myc-His/rat periostin obtained in Preparation example 3 was digested with restriction enzymes SacI and PmeI to excise a peptide fragment rat PN-1/Myc-His. This fragment was ligated to a vector fragment obtained by digesting pFastBacHTc (Invitrogen) with restriction enzymes SacI and KpnI (blunting) using a ligation kit (Takara Bio Inc.) to give an expression vector designated as pFastBac/rat periostin-1/Myc-His. The nucleotide sequence of the insert was confirmed by the method described in Preparation example 1-5.

Preparation Example 5

Preparation and Cultivation of a Recombinant Baculovirus

DH10BAC cells of *Escherichia coli* were transformed with pFastBac/rat periostin-1/Myc-His obtained in Preparation example 5 to prepare a recombinant baculovirus. Electrophoresis and PCR confirmed that the resulting baculovirus contains the desired insert.

Insect Sf9 cells ($2\times10^6$ cells/mL) infected with this recombinant baculovirus at MOI=0.1 were cultured in a serum-free medium (containing 50 µg/mL gentamicin in 200 mL of Sf-900IISFM (Invitrogen)) at 28° C. for 4-5 days and then the culture supernatant was harvested.

Preparation Example 6

Purification of Rat Periostin Protein

To an SP Sepharose Fast Flow column (10 mL bed volume) equilibrated with an equilibration buffer (50 mM sodium acetate buffer, pH 6.0, 0.1M sodium chloride) was applied 200 mL of the culture supernatant obtained in Preparation example 5, and the resulting flow-through fraction was pooled as an SP Sepharose flow-through fraction.

The column was washed with the equilibration buffer until the absorbance at 280 nm approached 0 (about 100 mL) to give an SP Sepharose wash fraction.

The column was eluted with 100 mL of an elution buffer (50 mM sodium dihydrogen phosphate (pH8.0), 0.5M sodium chloride, 5 mM imidazole) to give an SP Sepharose eluate fraction.

Then, 100 mL of the SP Sepharose eluate fraction was applied to an Ni-NTA agarose column (5 mL bed volume) equilibrated with 50 mM sodium phosphate buffer, pH8.0, 0.5M sodium chloride and 5 mM imidazole, and the resulting flow-through fraction was pooled as an Ni-NTA agarose flow-through fraction.

The column was washed with about 50 mL of a washing buffer (50 mL sodium dihydrogen phosphate, pH8.0, 0.5M sodium chloride, 5 mM imidazole) to give an Ni-NTA agarose wash fraction.

The column was eluted with about 25 mL each of elution buffers (1) 50 mM sodium dihydrogen phosphate, 0.5M sodium chloride, 20 mM imidazole, followed by similar compositions except that the imidazole concentrations were (2) 30 mM, (3) 40 mM, (4) 50 mM and (5) 60 mM to give Ni-NTA agarose eluate fractions (1)-(6).

Fractions shown to contain the desired protein by Western blotting were concentrated to 1 mL or less.

Then, the concentrated samples were applied to a gel filtration column (Sephacryl S-200HR φ11 mm×95 cm; 90 bed volume) equilibrated with degassed PBS (−) (137 mM NaCl, 8.1 mM $Na_2HPO_4$, 2.68 mM KCl, 1.47 mM $KH_2PO_4$) and eluted with PBS (−) and the eluate was lyophilized to give a purified rat periostin protein.

Example 1

Synthesis of Rat Exon-17 Peptide Chain and Preparation of Polyclonal Antibody against It A structure specific to rat PN-1 was identified as Exon-17 sequence by sequence comparison since heart dilation was induced by increased expression of the PN-1 gene in the heart of normal SD rats and the survival rate was improved by administration of an antisense oligonucleotide against rat periostin to the heart of Dahl heart failure model rats and rat PN-1 was shown to have no cell adhesive properties in contrast to previously reported PN-2. A peptide having a Cys residue added to the N-terminus of the amino acid sequence constituting this Exon-17 was chemically synthesized in 10 mg yield at a purity of 80% or more. Rabbits (Kbl:JW) were immunized with the polypeptide coupled to 6 mg of a carrier protein KLH. FCA (Freund's complete adjuvant) was used in the primary immunization, and FIA (Freund's incomplete adjuvant) was used in the secondary and subsequent immunizations. Administration was performed at 20 dorsal subcutaneous sites at weeks 0, 2, 4 and 6 using a peptide dose of 800 μg/animal in the primary immunization, and 400 μg/animal in the secondary and subsequent immunizations. The antibody titer was determined by ELISA and total sera were collected at week 7. Then, an affinity column was prepared by use of a synthetic peptide, and only the antibody specifically reacting to the Exon-17 peptide was collected. The polyclonal antibody against the peptide encoded by Exon-17 of rat periostin is hereinafter referred to as anti-rat Exon-17 peptide antibody.

Example 2

In vitro Study of the Presence or Absence of Anti-cell Adhesive Activity of Rat Periostin Protein (Rat PN-1)

Figure 2:
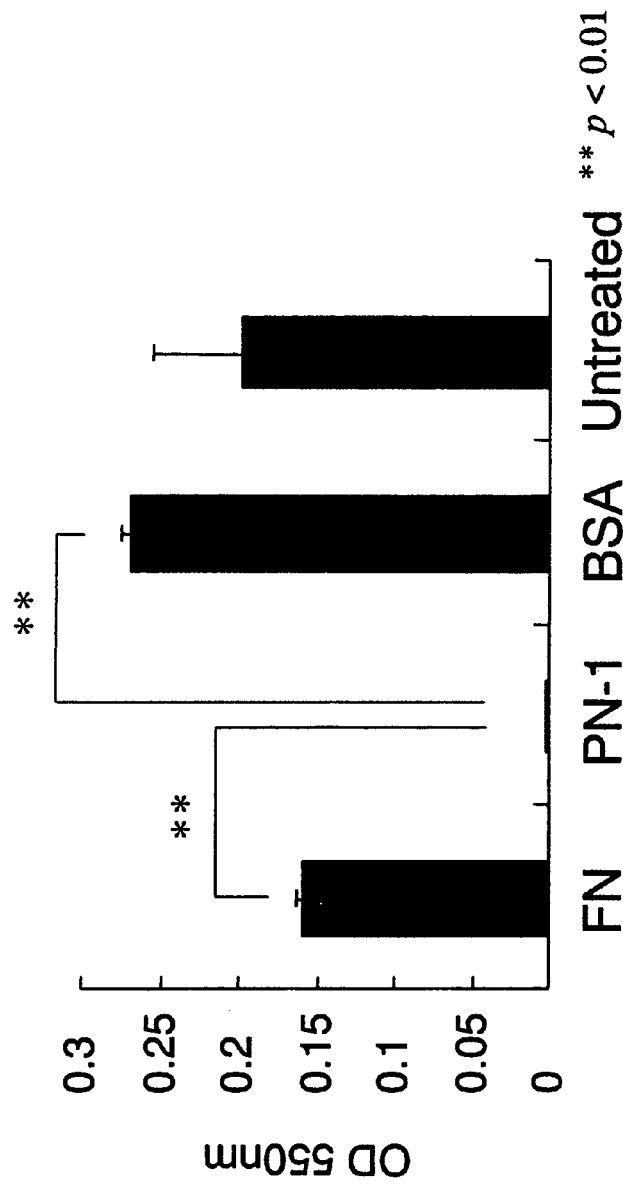
FIG. 2 is a diagram showing assay results of the anti-cell adhesive properties of rat PN-1 (Example 2).

Rat heart fibroblasts were obtained by a method similar to those described in literature (Ruwhof C, van Wamel A E, Egas J M, van der Laarse A. Mol Cell Biochem. 2000 May; 208 (1-2):89-98, Ashizawa N. Graf K, Do Y S, Nunohiro T, Giachelli C M, Meehan W P, Tuan T L, Hsueh W A. J Clin Invest. 1996 Nov. 15; 98 (10):2218-27). Specifically, 20 SD rats at 1-2 days of age were anesthetized with ether and the chest was disinfected with ethanol. The heart was isolated and placed in a dish containing PBS (−), where the heart was transversely incised to bleed it and further washed with PBS (−) three times, and then PBS (−) was discarded to the minimum possible level and the heart was minced with scissors. Then, the minced tissue was agitated in a 1:1 mixture of PBS (−): collagenase/trypsin at 37° C. for 15 minutes, and then cells were lysed by pipetting as thoroughly as possible. Then, the cell lysate was filtered through a platinum mesh in a centrifugal tube, and the platinum mesh was washed with 10 ml of M199 medium containing 10% serum and 10 ml of PBS (−). Then, the centrifugal tube was spun at 1500 rpm for 10 minutes, and the cells obtained as a pellet fraction were stirred in 20 ml of M199 medium containing 10% serum and plated on a dish. The dish was allowed to stand at 37° C. for 1 hour, and then cells adhered to the dish were collected as rat heart fibroblasts. The rat heart fibroblasts were plated on a 96-well plate at a density of $6.4 \times 10^4$ cells/100 μl and cultured overnight, and then the culture was incubated in fresh DMEM medium with 10% FBS containing 10 μg/ml cycloheximide at 37° C. for 1 hour. Then, the cells were washed twice with DMEM medium (serum free) prewarmed at 37° C., and rat periostin protein (rat PN-1) prepared according to the Preparation examples was added to DMEM medium (serum free) at a final concentration of 10 μg/ml. Fibronectin having cell adhesion-promoting properties was used as a positive control and BSA (bovine serum albumin) was used as a negative control. After incubation at 37° C. for 1 hour, microscopy showed that all the cells were separated in the group treated with rat periostin protein (rat PN-1), and the cells were washed twice with PBS (−) and then fixed in 10% neutral buffered formalin for 30 minutes. Then, the cells were washed with PBS (−) three times and then stained with crystal violet for 30 minutes. Then, the degree of staining was measured using a plate reader at 550 nm (BIO-RAD, Model 680 MICRO PLATE READER) (FIG. 2). As a result, the control groups treated with fibronectin and BSA and the untreated group did not show anti-cell adhesive properties because the adhered cells were not separated, in contrast to the group treated with rat periostin protein (rat PN-1) in which the cells were separated, showing that rat periostin protein (rat PN-1) has a separating effect on adhered cells, i.e., anti-cell adhesive properties.

Example 3

Figure 3:
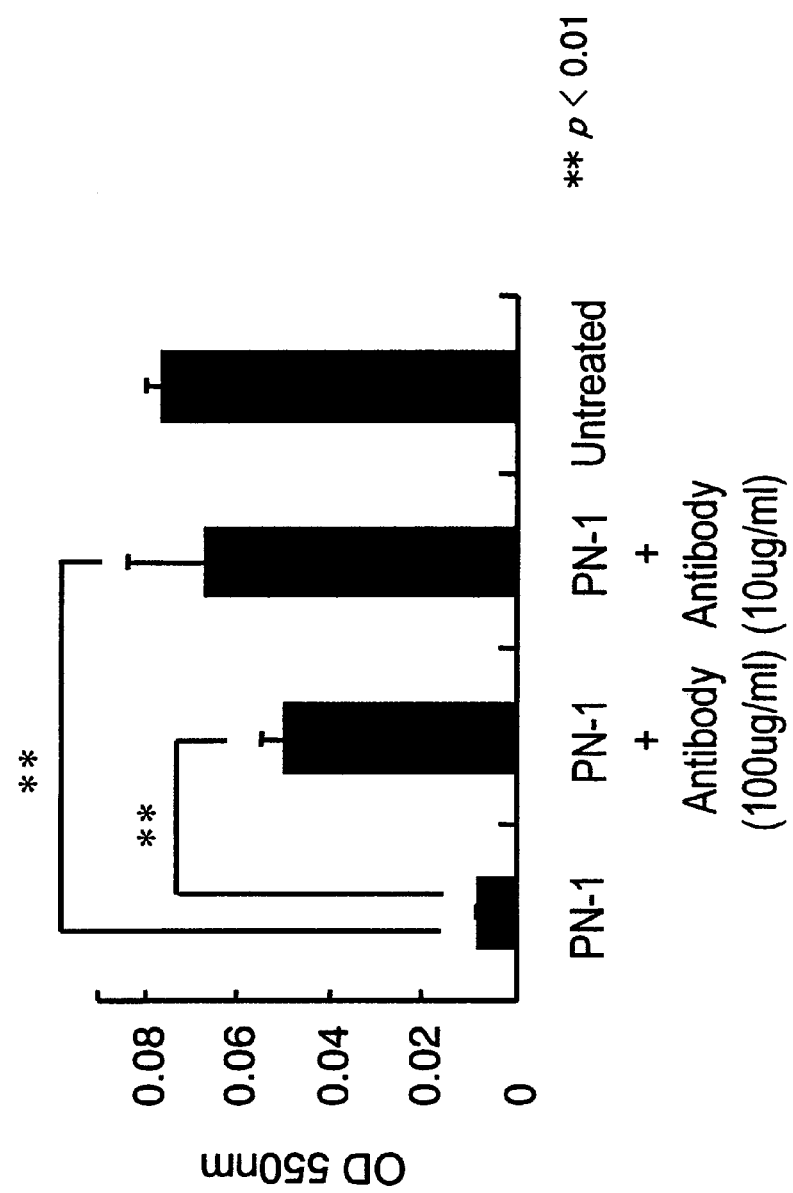
FIG. 3 is a diagram showing assay results of the inhibition of rat PN-1 activity by anti-rat Exon-17 peptide antibody (Example 3).

In vitro Study of the Neutralizing Activity of Anti-rat Exon-17 Peptide Antibody SD rat heart fibroblasts obtained by a method similar to that of Example 2 were plated on a 96-well plate at a density of $6.4 \times 10^4$ cells/100 μl and cultured overnight, and then the culture was incubated in fresh DMEM medium with 10% FBS containing 10 μg/ml cycloheximide at 37° C. for 1 hour. Then, the cells were washed twice with DMEM medium (serum free) prewarmed at 37° C., and rat periostin protein (rat PN-1) and anti-rat Exon-17 peptide antibody were added to DMEM medium (serum free) at final concentrations of 10 μg/ml and 100 μg/ml, respectively. Rat periostin protein alone was used as a positive control and BSA was used as a negative control. After incubation at 37° C. for 1 hour, microscopy showed that all the cells were separated in the group treated with rat periostin protein alone, and the cells were washed twice with PBS (−) and then fixed in 10% neutral buffered formalin for 30 minutes. Then, the cells were washed with PBS (−) three times and then stained with crystal violet for 30 minutes. Then, the degree of staining was measured using a plate reader at 550 nm (BIO-RAD, Model 680 MICRO PLATE READER) (FIG. 3). The results showed that anti-rat Exon-17 peptide antibody is an antibody having the activity of inhibiting rat periostin protein (PN-1)-induced separation of adhered cells, i.e., inhibiting the anti-cell adhesive properties of PN-1, i.e., neutralizing the anti-cell adhesive properties of rat periostin protein (rat PN-1).

Example 4

Effect of Anti-rat Exon-17 Peptide Antibody on Acute Myocardial Infarction Model Rats A male Lewis rat weighing 250-300 g was fixed on a rat surgical table after the animal was thoroughly anesthetized by peritoneal administration of pentobarbital (0.1 ml/100 g). A tube was orally inserted into the trachea and connected to a rat ventilator (tidal volume 3 ml, 80 breaths/min), and the skin was laterally incised from the left third intercostal space of the sternum and the underlying greater pectoral muscle was also laterally incised, and the intercostal space was opened using a rat rib spreader to expose the heart.

Then, the left coronary artery nearly beneath the left atrium was ligated with 1.0 silk using a curved needle having a diameter of 5 mm. After visual confirmation that the anterior and lateral walls along which the left coronary artery runs had been changed from red to white to show sufficient blockage of the coronary bloodstream and the disappearance of wall motion at these sites (in the sham operation group, the needle was passed through the coronary artery and then removed without ligation), the third and fourth ribs were fixed by ligation with 3.0 silk (after the lung was expanded to remove the air existing outside the lung in the rib cage so that the lung can be easily expanded). The incision site in the skin was sutured with 3.0 silk in the same manner and then observed for a while, and the tube was removed after confirmation of recovery of consciousness and resumption of spontaneous breathing.

Acute myocardial infarction models were sequentially prepared by the foregoing procedure.

On the following day, percutaneous echocardiography was performed under intranasal anesthesia with isoflurane, and small infarction models having an infarction size less than 20% of the entire periphery of the left ventricle were excluded. The remaining infarction models were ranked in order of increasing heart function, and alternately classified into a group treated with anti-rat Exon-17 peptide antibody and a group treated with a control antibody (rabbit IgG) each 200 µg via tail vein.

The antibodies were administered to each group on the day following the preparation of the models and at intervals of 6 days after the initial administration, a total of 4 times.

The heart was evaluated by echocardiography through the chest wall at intervals of one week until the end of 8 weeks. At the end of 8 weeks, a tube was inserted into the trachea and connected to a ventilator under anesthesia with pentobarbital, and the skin was incised from the left neck and the neck muscles were retracted with forceps to expose the left common carotid artery, and after bleeding was stopped by ligation at the origin of the left carotid artery, the artery was pierced at a distal site by small scissors and a rat mirror catheter was inserted from that site in such a manner that the catheter tip with a pressure sensor reached the inside of the left ventricle while the catheter was connected to a computer to measure heart function and blood pressure and the like.

Figures 1, 4:
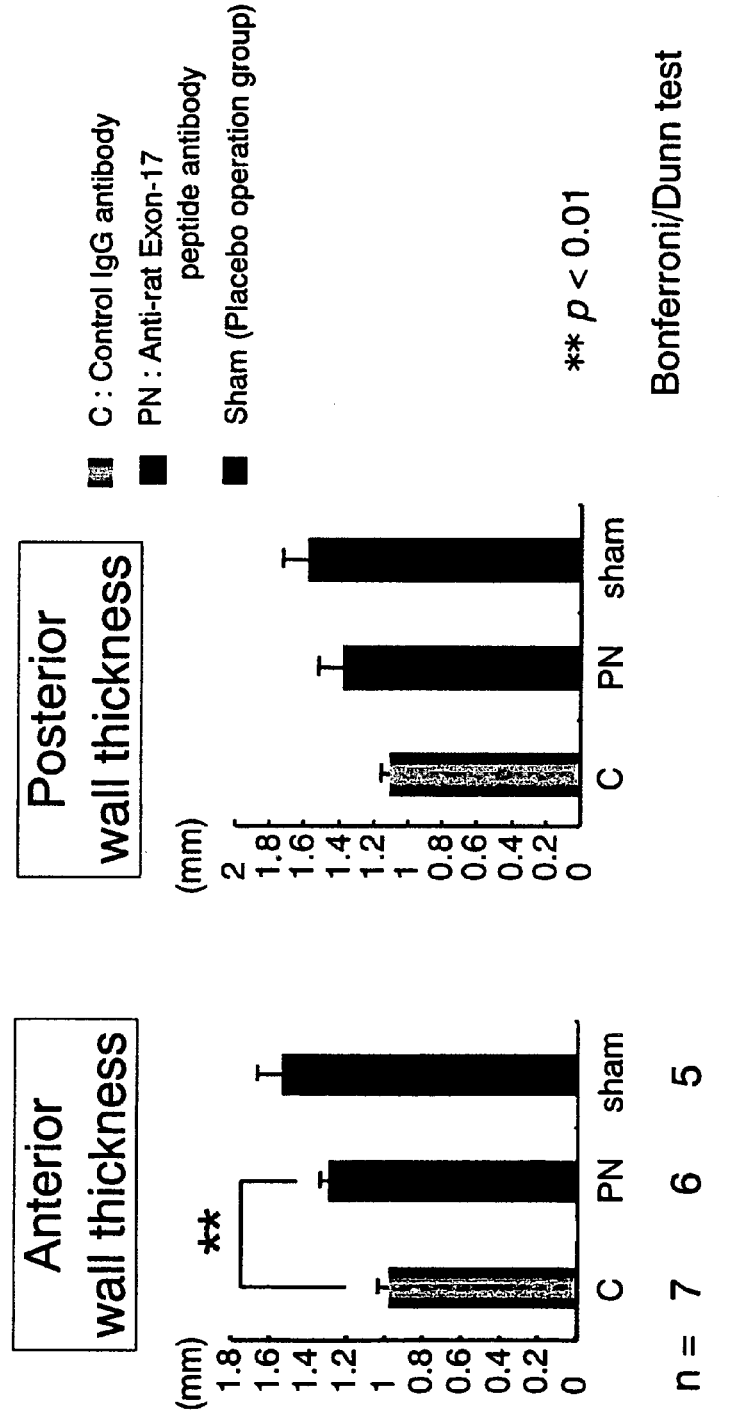
Figures 2, 4:
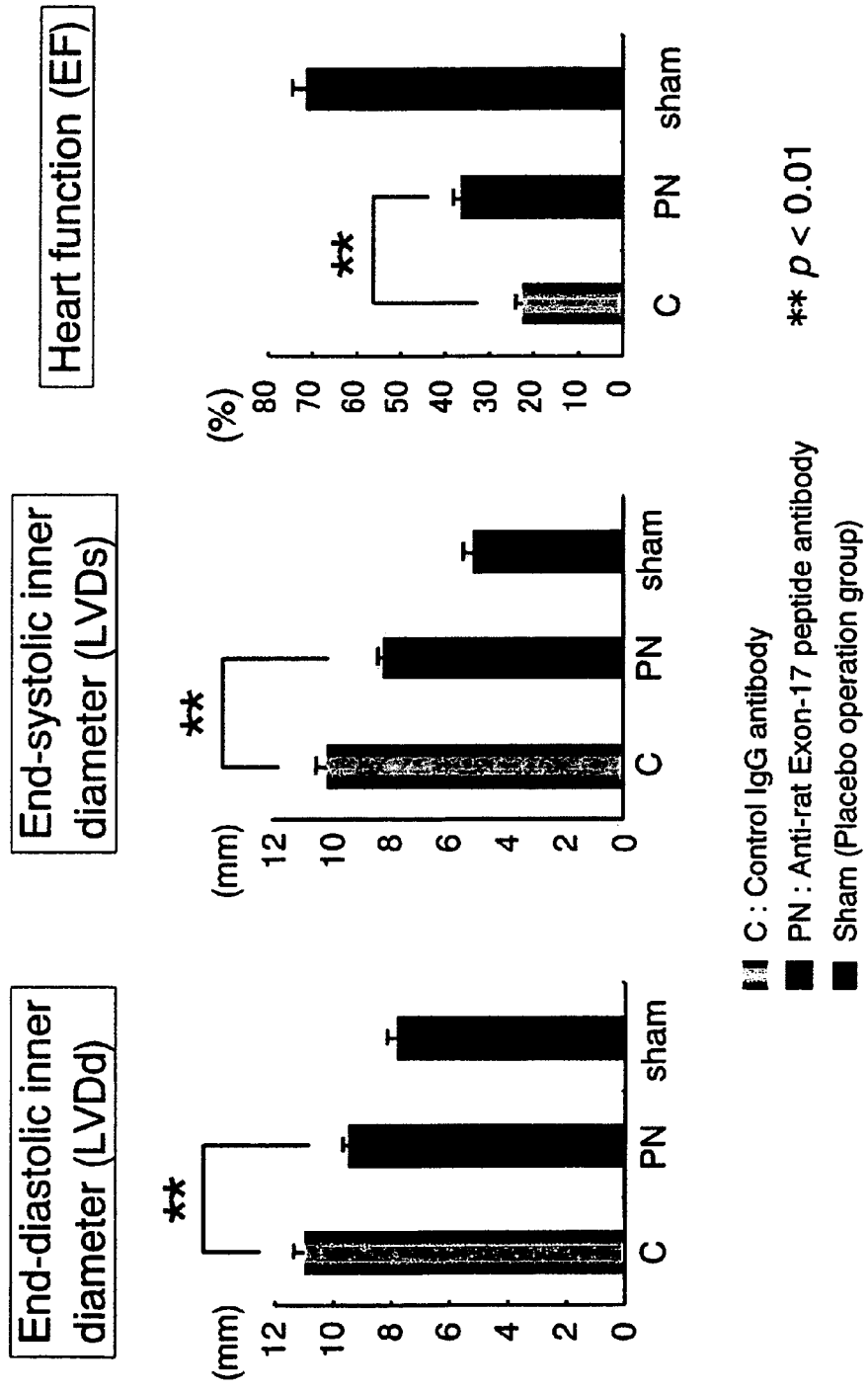
Figures 3, 4:
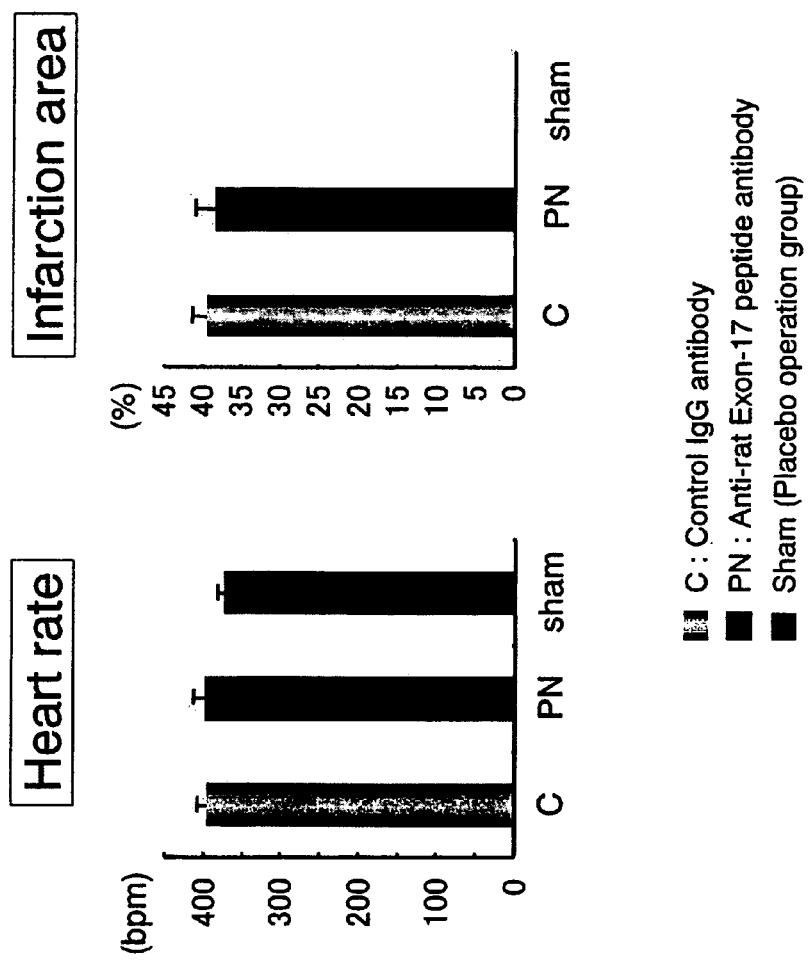
Figures 1, 5:
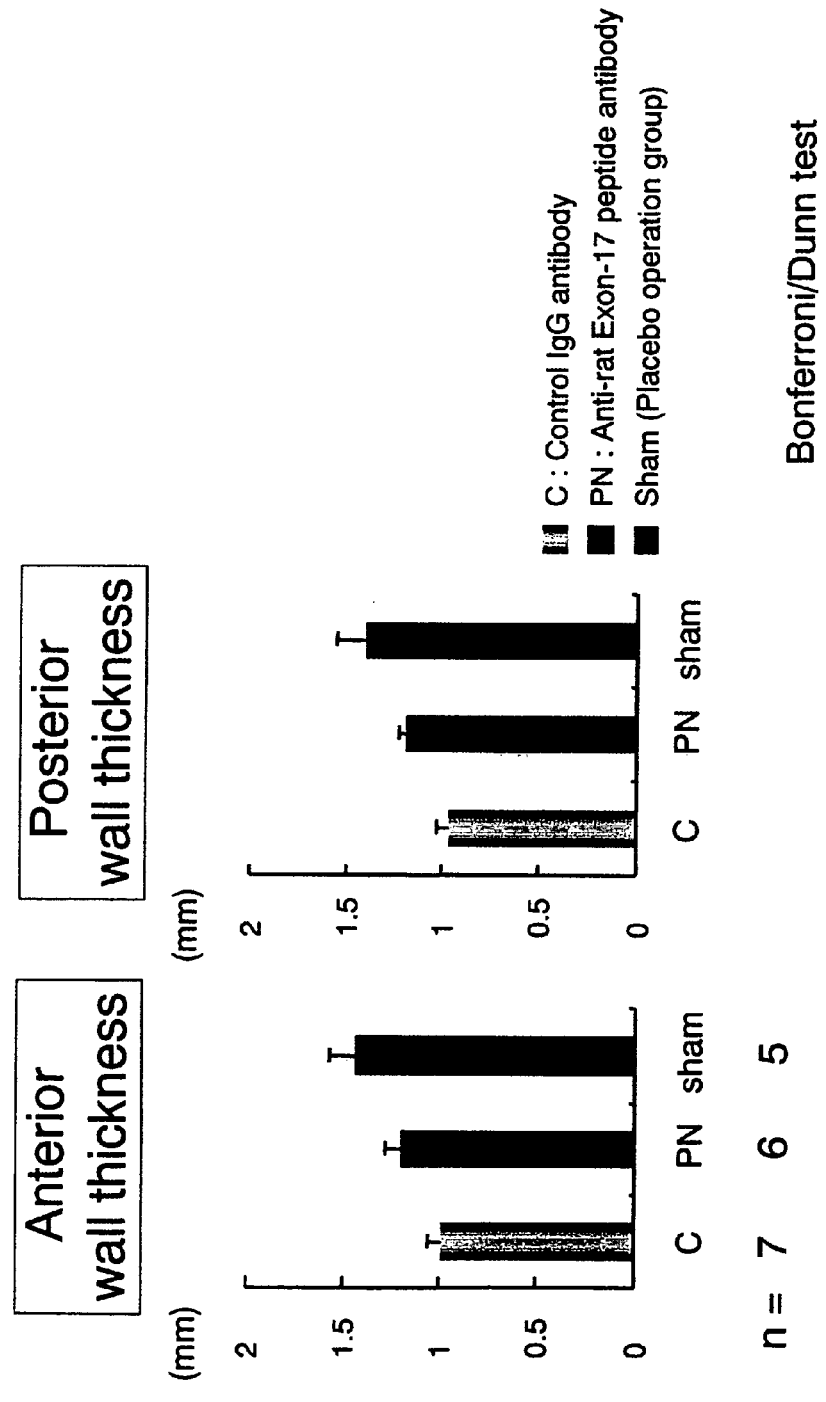
Figures 2, 5:
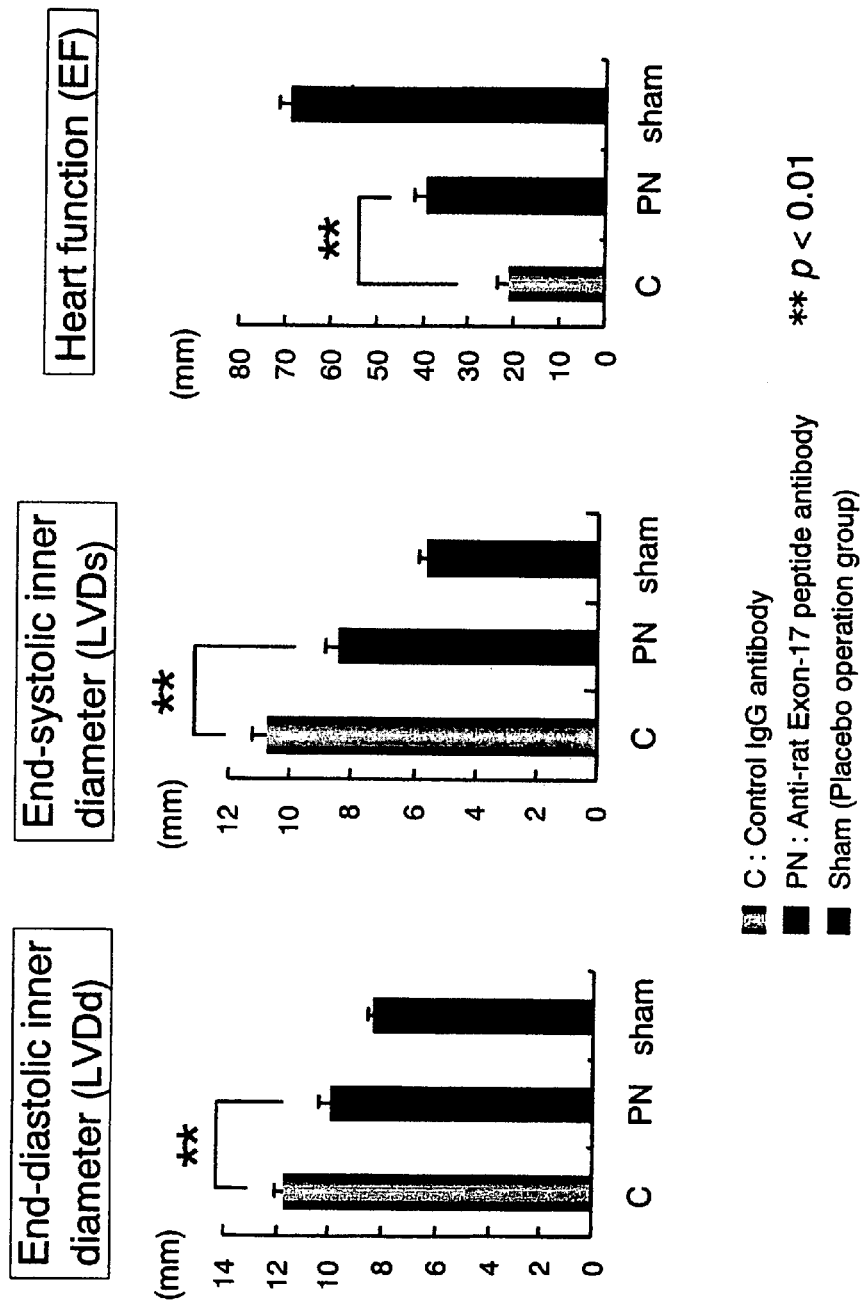
Figures 3, 5:
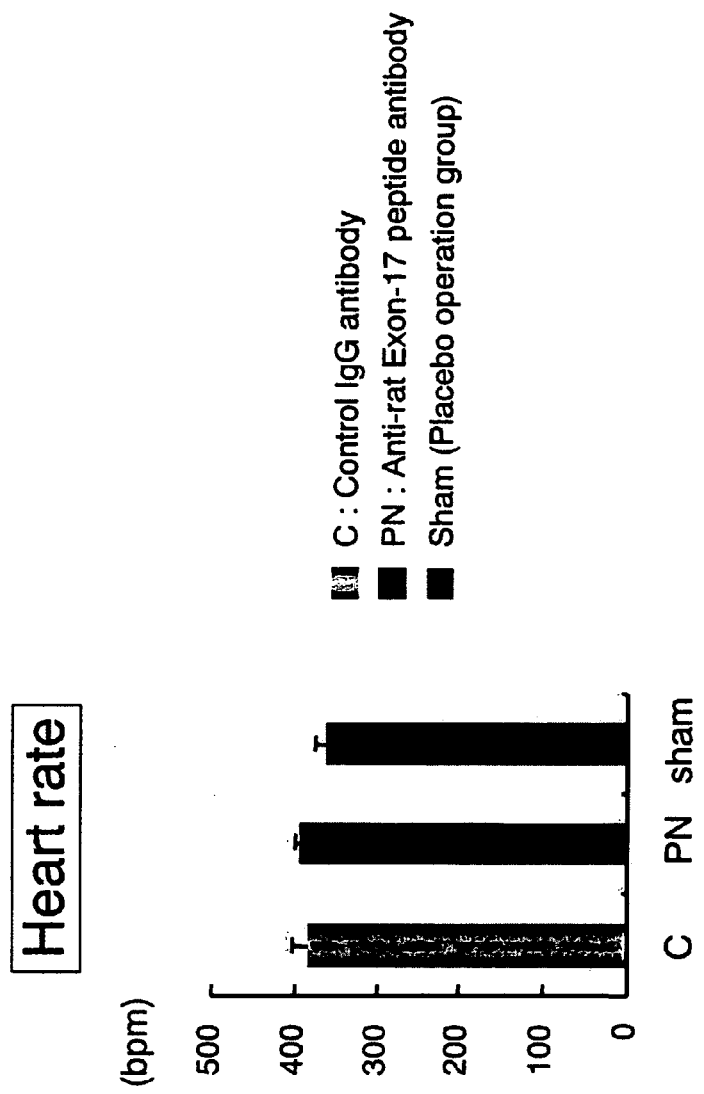
Figures 1, 6:
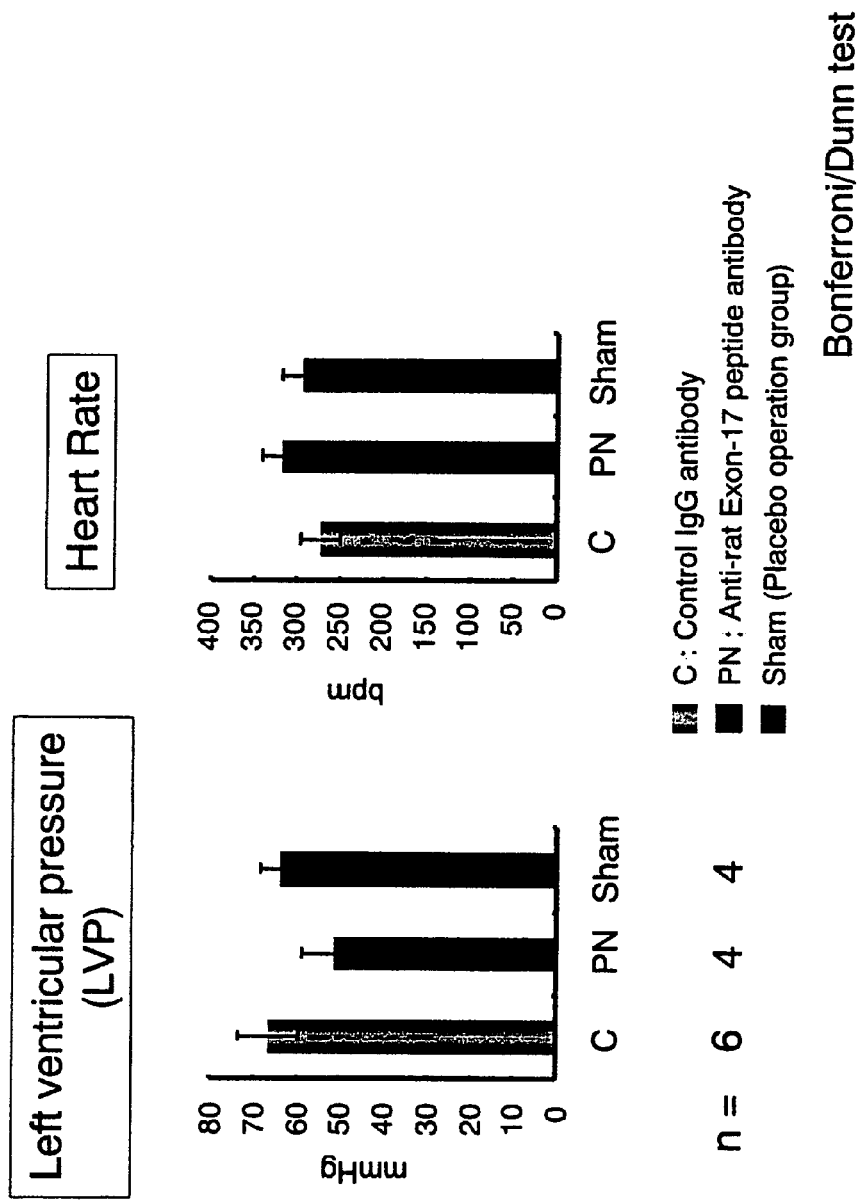
Figures 2, 6:
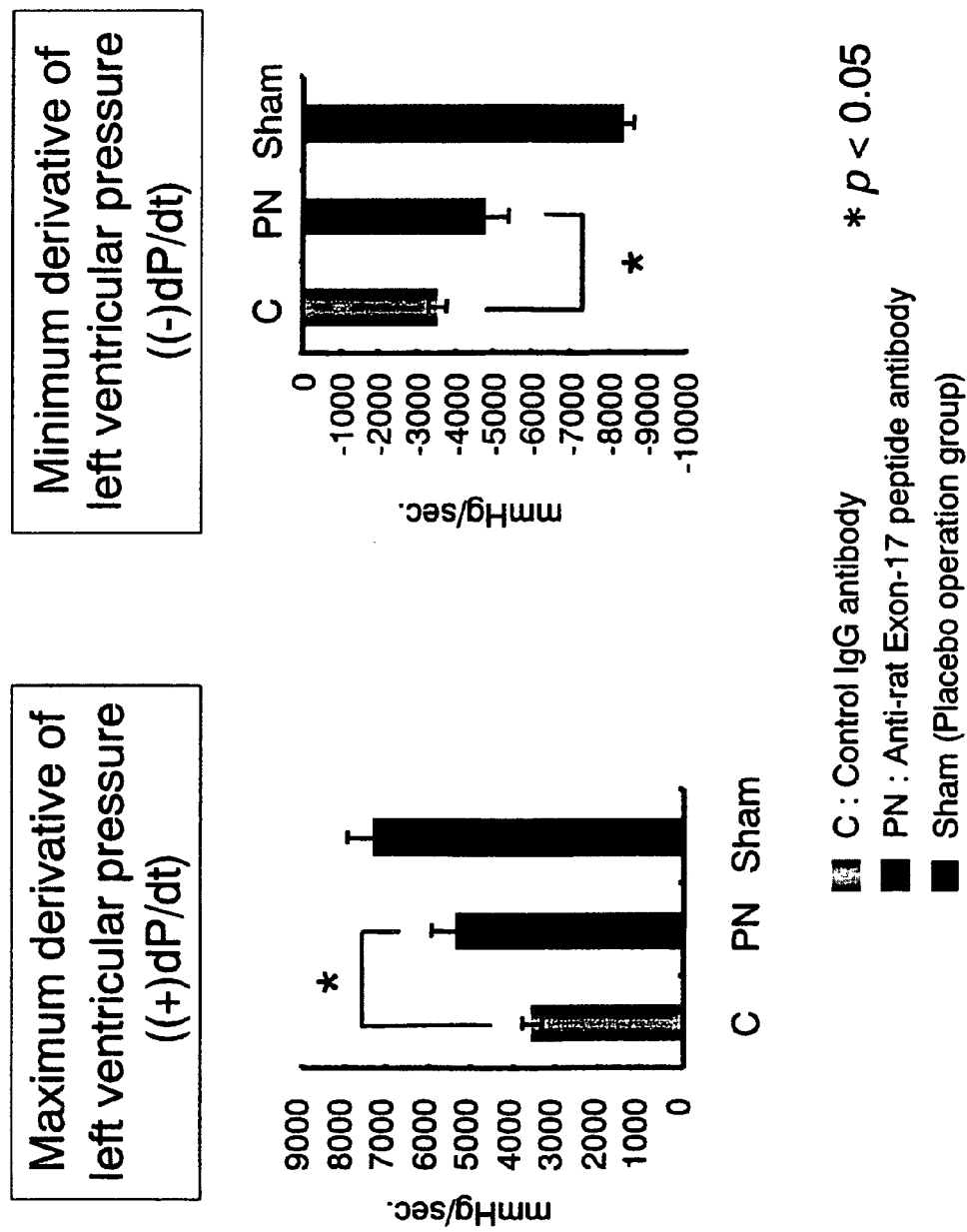
Figures 3, 6:
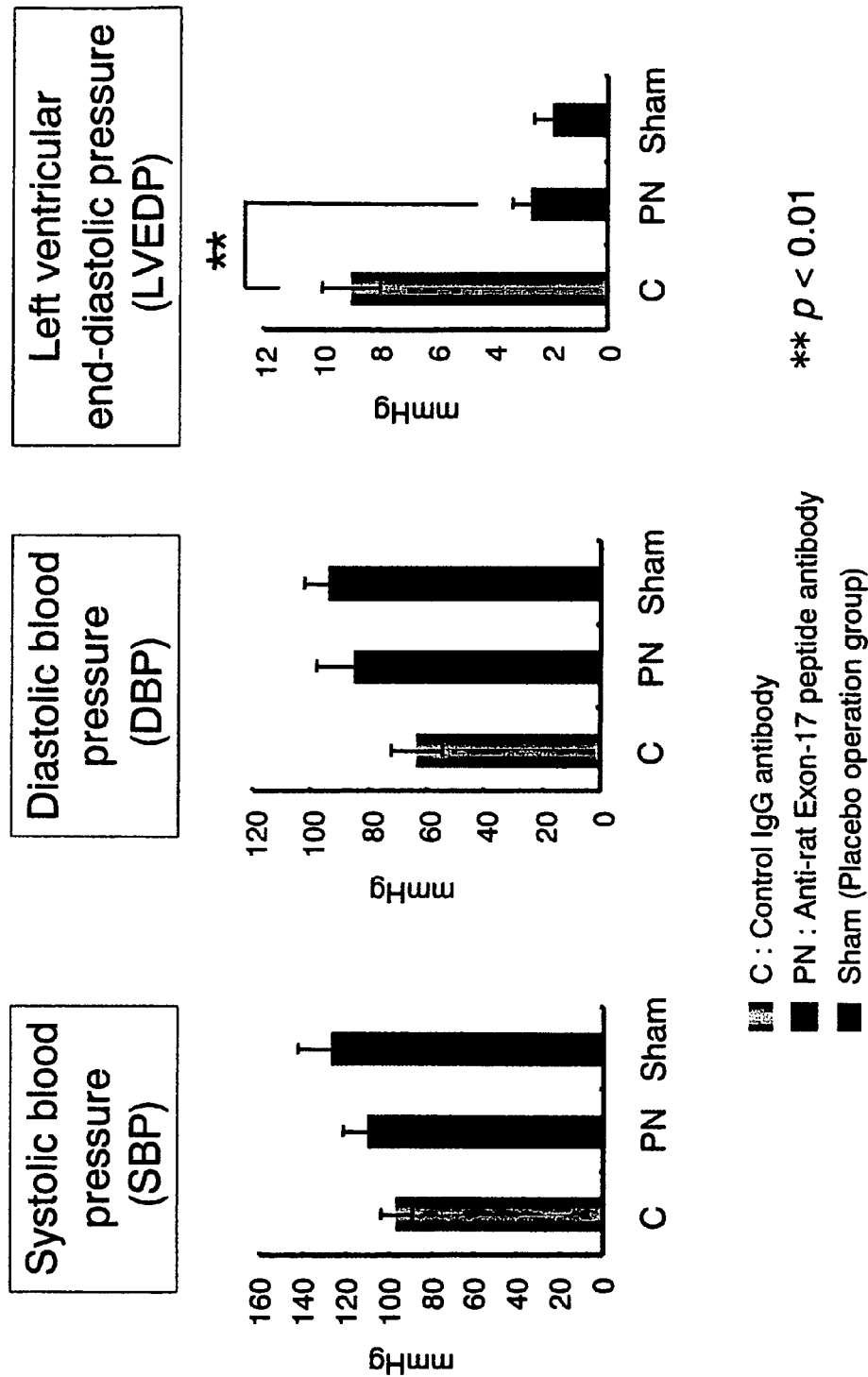
Figure 7:
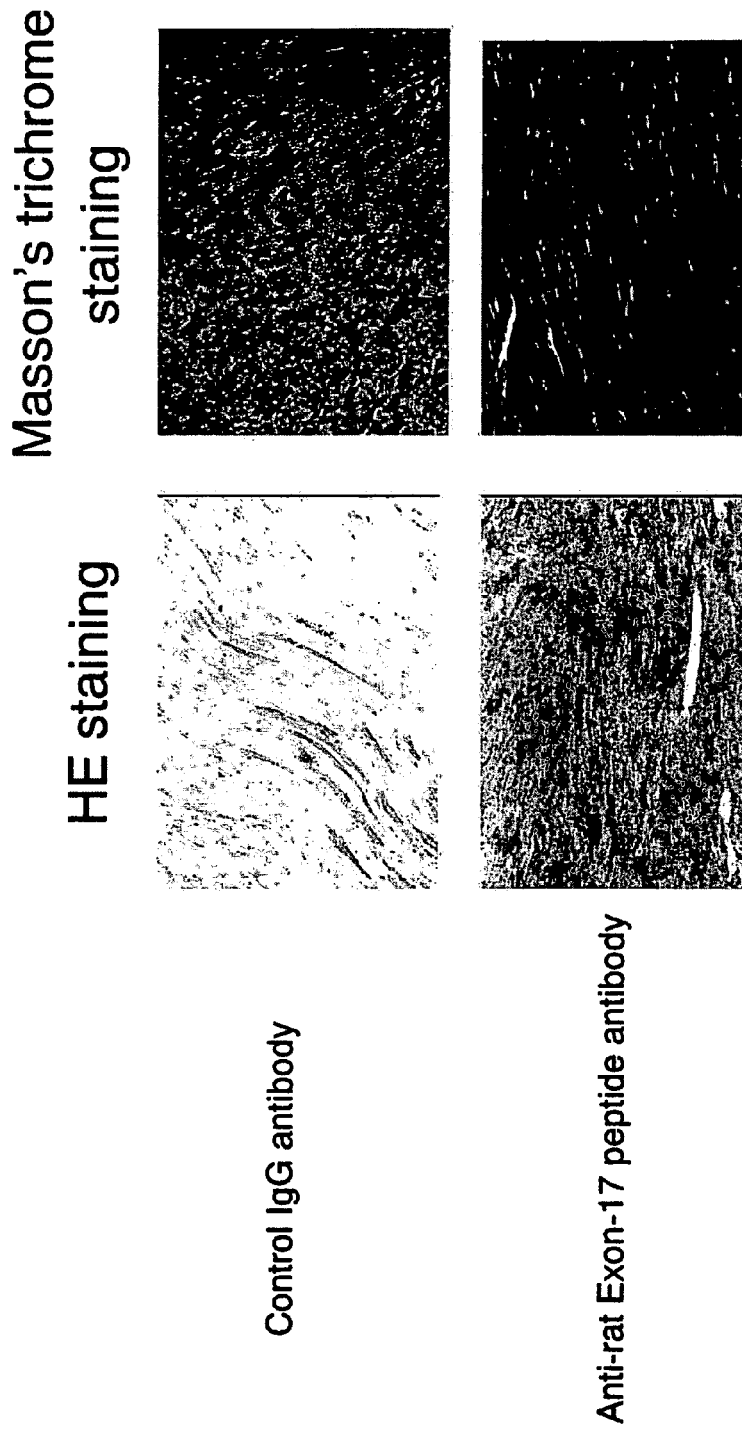
FIG. 7 is a diagram showing the results of histological analysis of model rats treated with anti-rat Exon-17 peptide antibody (Example 4).
Figure 8:
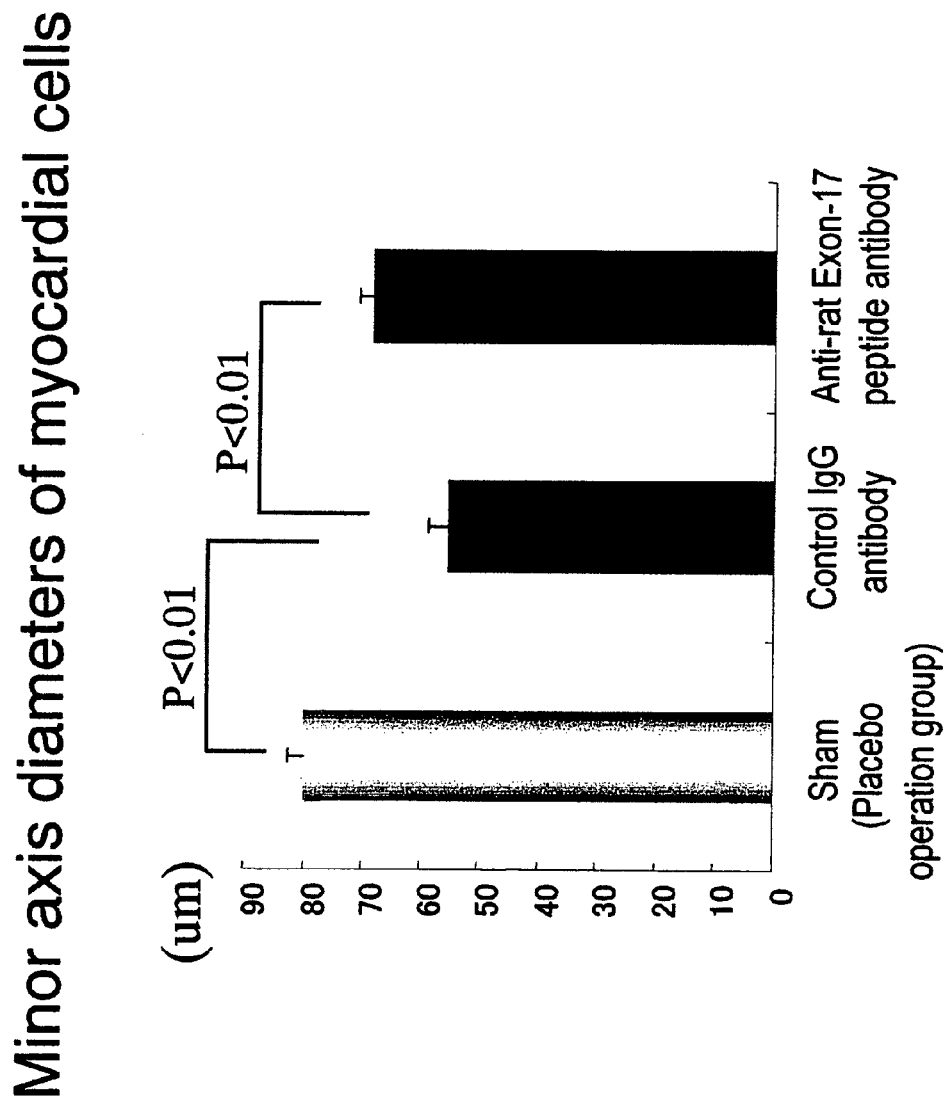
FIG. 8 is a diagram showing the minor axis diameters of myocardial cells of model rats treated with anti-rat Exon-17 peptide antibody (Example 4).
Figures 1, 9:
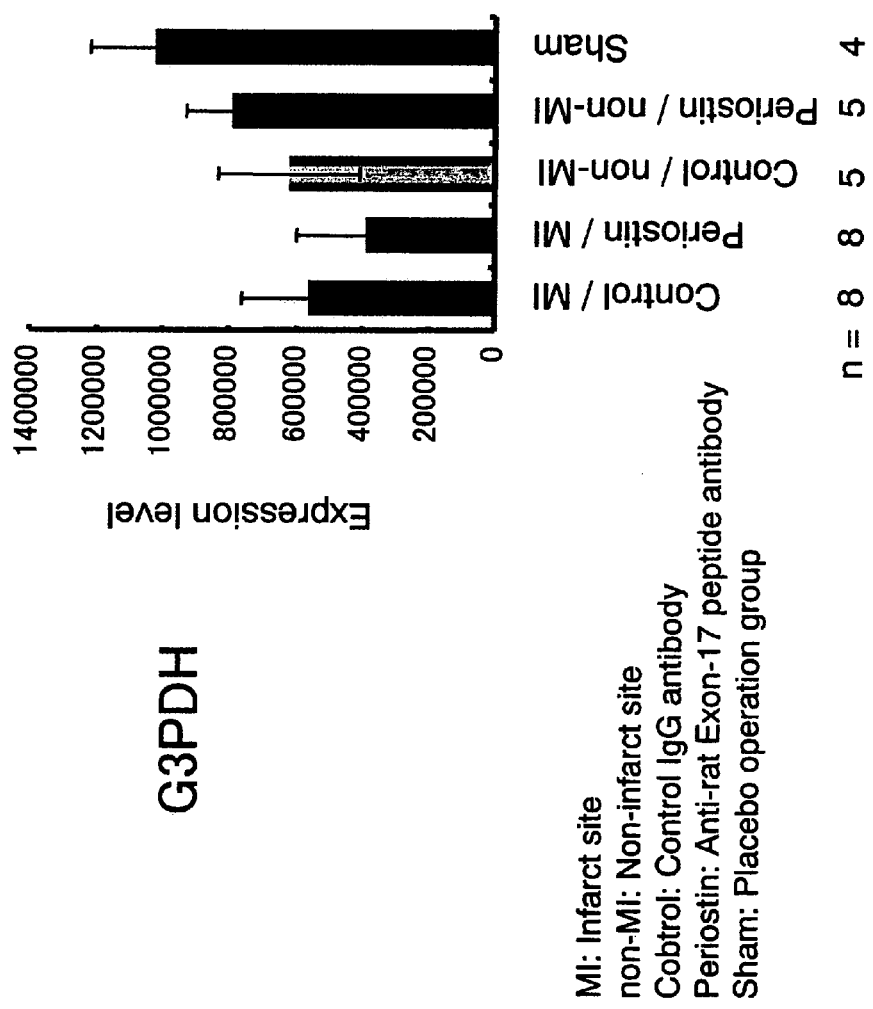
Figures 2, 9:
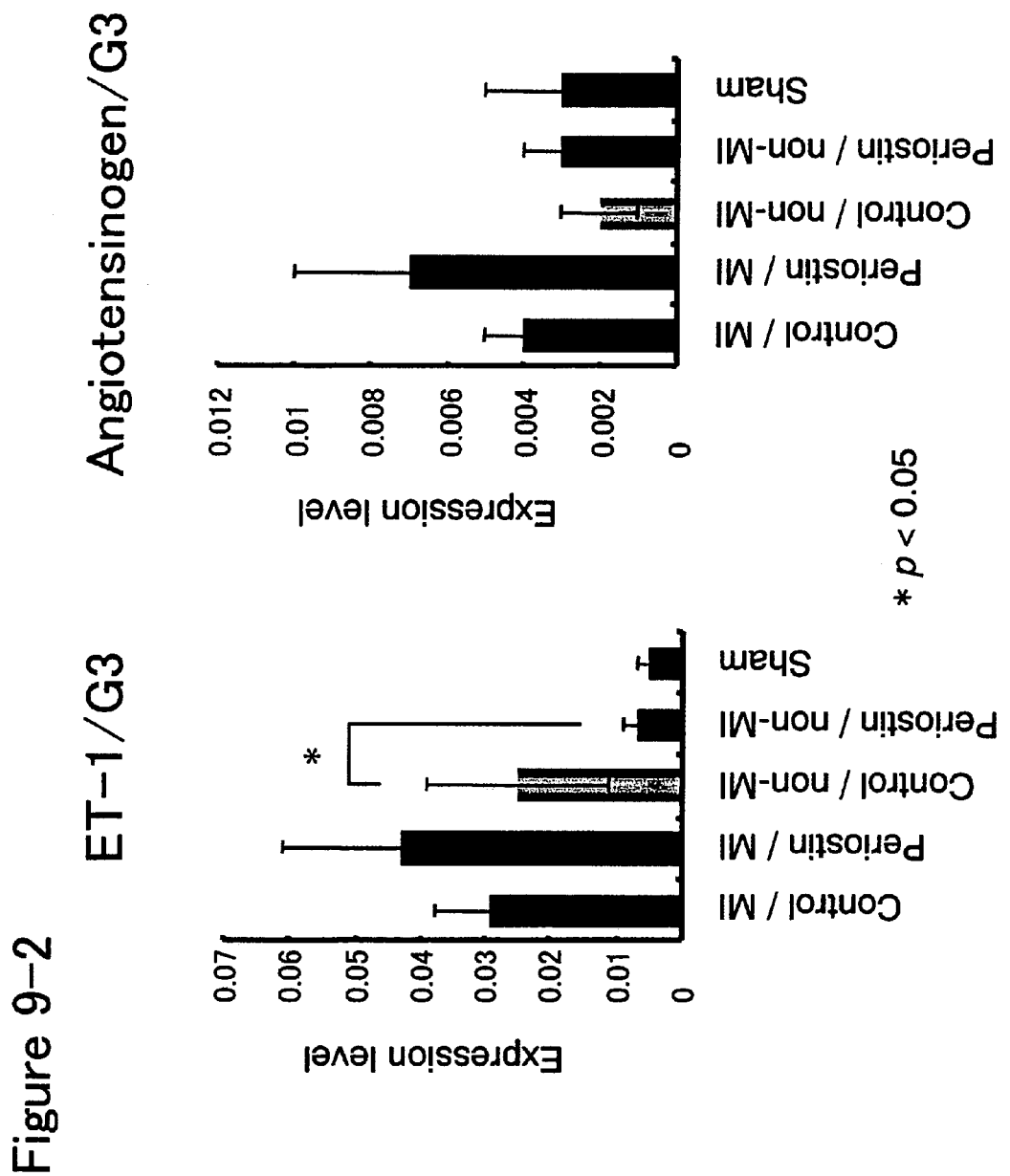
Figures 3, 9:
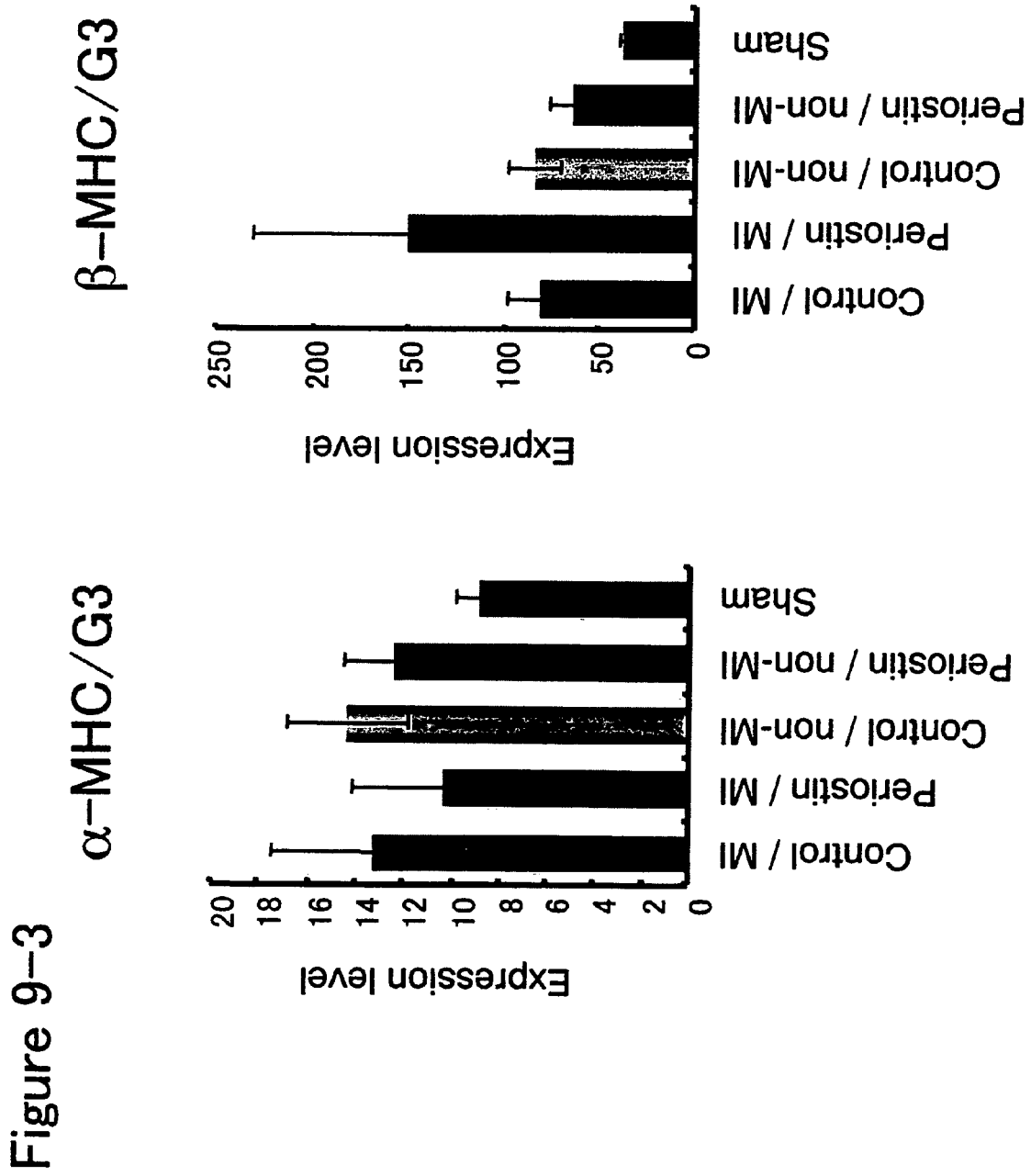
Figures 4, 9:
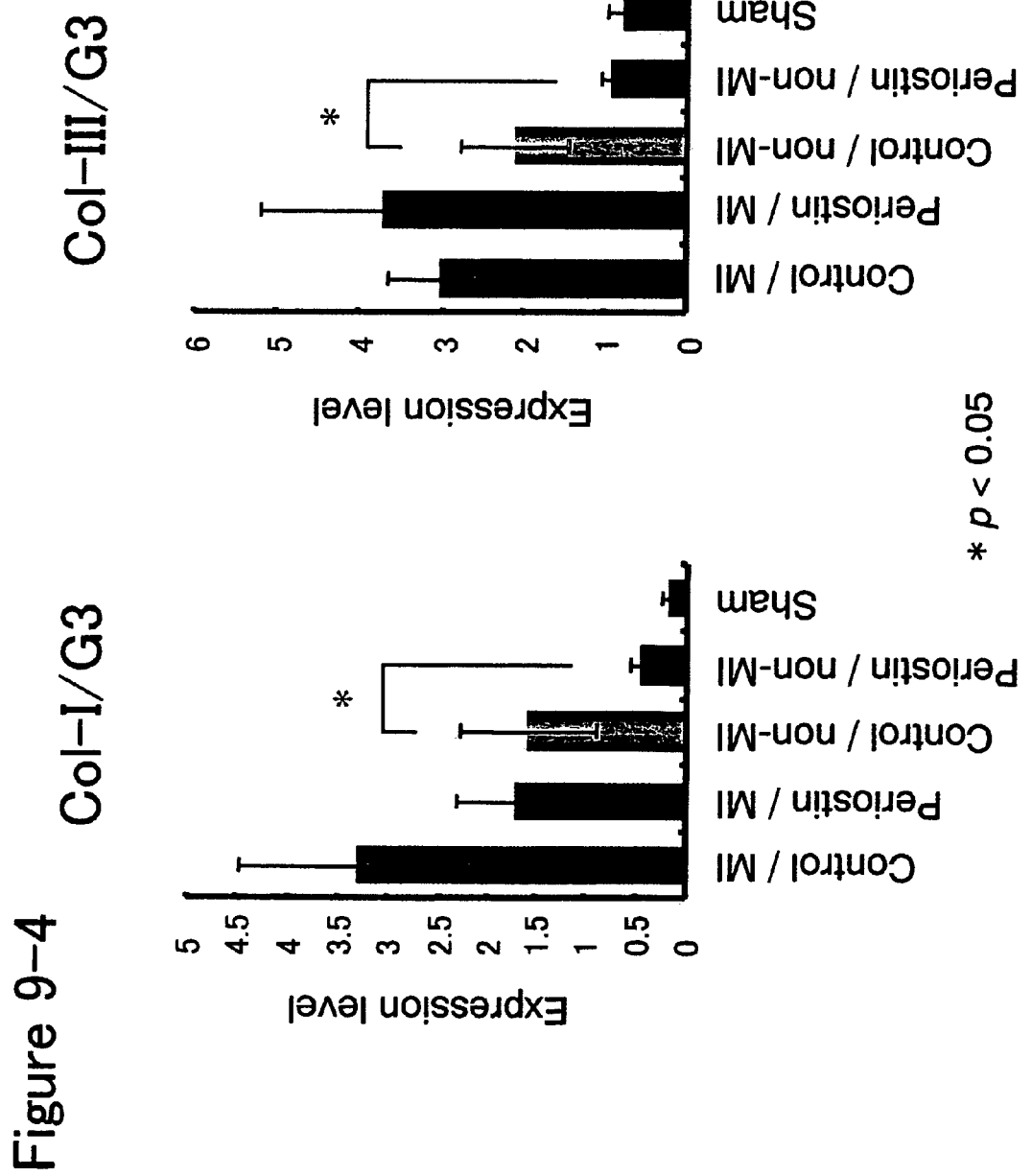
Figures 5, 9:
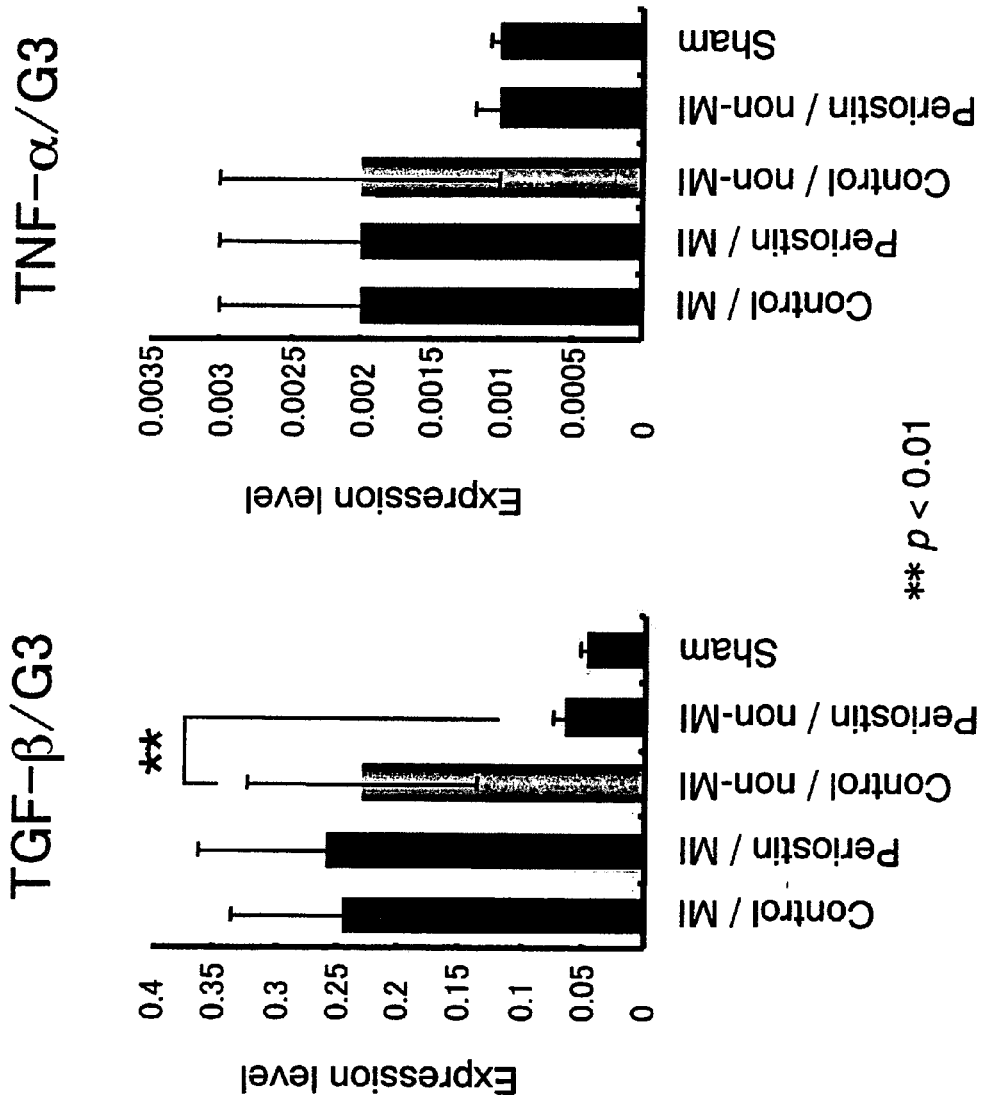

The results of echocardiography 4 weeks after the preparation of the models showed that the reduction of the anterior wall thickness and posterior wall thickness of the heart was inhibited, the increase of the end-diastolic inner diameter and end-systolic inner diameter was inhibited, and that the EF value indicative of the contractile function of the heart increased in the group treated with anti-rat Exon-17 peptide antibody significantly as compared with the control group treated with rabbit IgG. In brief, heart dilation was inhibited, showing that heart function was improved (FIG. 4-1 to FIG. 4-3). The results of echocardiography 8 weeks after the preparation of the models also showed inhibition of heart dilation and improvement of heart function in the same manner as the results after 4 weeks (FIG. 5-1 to FIG. 5-3). These results suggested that the effect of anti-rat Exon-17 peptide antibody inhibiting heart dilation and improving heart function is maintained even about 4 weeks after the administration of the antibody. Then, hemodynamics showed significant differences in maximum derivative of left ventricular pressure ((+)dP/dt), minimum derivative of left ventricular pressure ((−)dP/dt) and left ventricular end-diastolic pressure (LVEDP) in the group treated with anti-rat Exon-17 peptide antibody as compared with the control group treated with IgG, suggesting that heart function was improved (FIG. 6-1 to FIG. 6-3). In heart sections stained with Masson trichrome, blue sites decreased in the group treated with anti-rat Exon-17 peptide antibody as compared with the control group treated with IgG, showing that fibrosis was inhibited (FIG. 7). Analysis of the minor axis diameters of myocardial cells showed that the reduction of the minor axis diameters of myocardial cells was significantly inhibited in the group treated with anti-rat Exon-17 peptide antibody as compared with the control group treated with IgG (FIG. 8). This result correlates with the result of echocardiography. Moreover, the results of gene expression analysis in infarct sites and non-infarct sites showed that the expression levels of endothelin-1 (ET-1), collagen type I, III, and TGF-beta at non-infarct sites significantly decreased in the group treated with the neutralizing antibody as compared with the group treated with the control antibody to levels comparable to those of the sham group, indicating that the condition was improved (FIG. 9-1 to FIG. 9-5).

Example 5

Cloning of Full-Length Human Periostin-1 cDNA cDNA prepared from 1 µg of human heart-derived total RNA (Clontech, catalog Now 64100-1, lot No. 4120493) was used as a template to perform PCR with KOD plus DNA polymerase (Toyobo Co., Ltd.) using the following primers for full-length cloning: sense chain 5'-AAGCTAGCCAC-CATGATTCCCTTTTTACCCAT-3' (SEQ ID NO: 27) and antisense chain 5'-AACTCCACAATTTCCCTCAT-3' (SEQ ID NO: 28). The resulting PCR products were cloned using a Zero Blunt TOPO PCR Cloning kit (Invitrogen).

A sense chain 5'-TAACCAAAGTTGTGGAACCAA-3' (SEQ ID NO: 29) was prepared from a region corresponding to human periostin Exon-17, while an antisense chain 5'-TGTGTCTCCCTGAAGCAGTC-3' (SEQ ID NO: 30) was prepared from a region corresponding to Exon-21, followed by selection of clones detected with these primers from this clone group. Then, the nucleotide sequences of the selected clones were determined to select an unspliced clone, thereby completing the full-length cloning of human periostin-1 cDNA. The resulting clone was designated as pCR4/human periostin-1.

Example 6

Construction of Human Periostin-1 Expression Vector for In vitro Translation The plasmid pCR4/human periostin-1 obtained in Example 5 was digested with restriction enzymes Pme I and Not I to excise a DNA fragment human periostin-1, which was then blunted. A pTNT expression vector (Promega), into which CATCACCATCACCATCACTAA (6×His+termination codon) (SEQ ID NO: 31) had been inserted, was enzymatically digested at the Mlu I site in its multicloning site and then blunted. The DNA fragment obtained above was ligated to this vector using a ligation kit (TaKaRa Bio Inc.).

Then, for the purpose of creating in-frame fusion with the His tag, synthetic linkers (sense chain 5'-CTAGAAGAC-GATTAAGGGAAGGTCGTTCTCAGCTG-GAAGTTCTGTTCCAGGGGCCC-3' (SEQ ID NO: 32) and antisense chain 5'-GGGCCCCTGGAACAGAACTTC-CAGCTGAGAACGACCTTCCCTTAATCGTCTT-3' (SEQ ID NO: 33)) were prepared and ligated to the vector fragment digested with restriction enzymes Xba I and Sma I using a ligation kit. The nucleotide sequence of the ligated part was confirmed, and the resulting expression vector was designated as pTNT/human periostin-1/His.

Example 7

Protein Synthesis by In vitro Translation

The expression vector obtained in Example 6 was provided for in vitro protein synthesis with TNT SP6 Quick Coupled Transcription/Translation Systems (Promega). More specifically, relative to 2 μg of the pTNT/human periostin-1/His expression vector, 40 μl of SP6 Quick Master Mix and 1 μl of 1 mM methionine were added and diluted with DEPC-treated water to give a total volume of 50 μl, followed by reaction at 30° C. for 90 minutes. The reaction product was stored at -80° C. until purification.

Example 8

Purification of Human Periostin Protein (PN-1)

The synthetic protein obtained in Example 7 was purified using a MagZ Protein Purification System (Promega). More specifically, to the synthetic protein obtained in Example 7, 2 volumes of MagZ Binding/Wash buffer were added and mixed well. The sample thus prepared was added to MagZ Binding Particles. After stirring of this mixture at 4° C. for 1 hour, the supernatant was removed and the MagZ Binding Particles were washed four times with MagZ Binding/Wash buffer, followed by elution of the synthetic protein with MagZ Elution buffer. The protein thus purified was stored at -80° C. until use.

Example 9

Preparation of Monoclonal Antibody Against Human Periostin Exon-17 Peptide Chain (1) Antigen Preparation A peptide (SEQ ID NO: 25) having a Cys residue added to the N-terminus of the amino acid sequence constituting human periostin Exon-17 (SEQ ID NO: 4) was chemically synthesized by the Fmoc method to obtain the peptide in 10 mg yield at a purity of 90% or more. As a carrier protein, KLH (5 mg, CALBIOCHEM) was coupled to this peptide to give an antigen solution. Namely, KLH was dissolved in PBS (0.01M) and adjusted to 3.3 mg/mL, to which a 0.2524 mg/mL MBS solution (GE Healthcare Bio-Sciences KK) was then added dropwise and reacted with stirring at room temperature for 60 minutes. Dichloromethane was used to remove free MBS, to thereby obtain KLH-MB. This KLH-MB (5 mg) was mixed with the antigen peptide (5 mg) dissolved in 0.01M sodium phosphate buffer (pH7.2) and reacted with stirring at 4° C. for 12 hours to obtain the antigen solution.

(2) Immunization

Three female BALB/c mice at 6 weeks of age were each subcutaneously injected into both soles with the whole volume of a mixed emulsion of the antigen solution (50 μl) containing 100 μg KLH-coupled antigen peptide obtained in (1) and FCA (Freund's complete adjuvant, 50 μl). The mice were then injected twice into both soles with an in situ prepared mixed emulsion of the above antigen solution and FIA (Freund's incomplete adjuvant) at an interval of 2 weeks. The mice were then sacrificed by cervical dislocation and lymph nodes in their soles were aseptically collected.

While supplying RPMI medium (Kohjinbio Co., Ltd.), the above lymph nodes were crushed and passed through a mesh of about 10 μm pore size to obtain lymph node cells suspended in RPMI medium. This suspension was centrifuged at 1000 rpm for 10 minutes to obtain lymph node cells as a pellet fraction. After this pellet fraction was hemolyzed to remove red blood cells in a solution (1 ml) prepared by adding 20 mM HEPES buffer (pH7.4) to a 0.84% ammonium chloride solution, centrifugation was repeated at 1,000 rpm for 5 minutes. The resulting pellet fraction (cell fraction) was washed several times with RPMI medium and then used for cell fusion.

(3) Preparation of Myeloma Cells

The mouse myeloma cell line P3X63Ag8U.1 (P3U1) that was resistant to 8-azaguanine and secreted no immunoglobulin was cultured in RPMI medium containing 20% fetal calf serum (FCS) in a 10% $CO_2$, 37° C. incubator. Cells in the logarithmic growth phase were collected and centrifuged at 1,000 rpm for 5 minutes to obtain the cells alone as a pellet fraction, which were then suspended in RPMI medium.

(4) Cell Fusion

The RPMI medium obtained in (2) containing $10^8$ to $3 \times 10^8$ immunized lymph node cells and the RPMI medium obtained in (3) containing $10^8$ myeloma cells were mixed and then centrifuged at 1,000 rpm for 10 minutes. The supernatant was gently removed to obtain the cells as a pellet fraction, followed by addition of 1 ml of 25% (w/v) polyethylene glycol 1500 (PEG 1500, Boehringer). The cells were further diluted to a total volume of 10 ml by slow addition of RPMI medium. To this suspension, 20% FCS-containing RPMI medium (10 ml) was added and allowed to stand for a while, followed by centrifugation at 1,000 rpm for 5 minutes. The resulting pellet fraction (cell fraction) was adjusted to a cell density of $10^6$ cells/ml by addition of 20% FCS-containing RPMI, and this cell suspension was dispensed at 200 μl/well in 96-well culture plates (Corning). After culturing in a 5% $CO_2$, 37° C. incubator for 24 hours, HAT solution (Invitrogen) was added and culturing was continued for an additional 2 weeks.

(5) Screening by ELISA

Screening was performed to determine positive wells showing a reaction between the culture supernatant and the antigen peptide.

For use as an antigen solution for assay, the antigen peptide (2 mg) obtained in (1) was coupled to ovalbumin (OVA) as a carrier protein to prepare a conjugate.

Each well of a 96-well microtiter plate (Falcon 353912) was coated with the above conjugate (1 µg/ml) by standing overnight at 4° C. After washing this plate, the culture supernatant from (4) (50 µl, containing monoclonal antibodies) was added dropwise to each well and allowed to stand in a 37° C. incubator for 2 hours, followed by washing with PBS(−) (phosphate buffered saline). After addition of alkaline phosphatase-conjugated sheep anti-mouse IgG antibody (Zymed), the plate was allowed to stand in a 37° C. incubator for 1 hour, washed with PBS(−) and then color developed for 20 minutes by addition of a color development substrate (ALP). The absorbance (antibody titer) at OD 490 nm was measured for each well with a plate reader (BIO-RAD, Model 680 MICRO PLATE READER) to confirm its reactivity with the antigen peptide, to thereby determine positive wells showing a reaction between the culture supernatant and the antigen peptide.

(6) Cloning of Antibody-Producing Cells

Cells in the positive wells whose reactivity with the antigen peptide was confirmed by ELISA in (5) were provided for cloning of antibody-producing cell lines by limiting dilution. Namely, cells in the positive wells were plated into each well of a 96-well culture plate and cultured in a 5% $CO_2$, 37° C. incubator for 2 weeks. In the same manner as used in (5), reactivity with the antigen peptide was confirmed by ELISA for the culture supernatant in each well, and cloning by limiting dilution was repeated again for each positive well to obtain 30 cells having a high reactivity with the antigen peptide and showing good colony growth. These cells were transferred to 24-well culture plates and cultured in a 5% $CO_2$, 37° C. incubator for 2 weeks. In the same manner as used in (5), reactivity with the antigen peptide (antibody titer) was confirmed again by ELISA for each culture supernatant. Cells in 10 wells showing a high absorbance at OD 490 nm, i.e., 10 hybridoma cell lines were determined to be useful as antibody-producing cells and were selected.

| Hybridoma cell lines | |
|---|---|
| No. | OD value |
| 1 | 0.41 |
| 2 | 0.37 |
| 3 | 0.68 |
| 4 | 0.24 |
| 5 | 0.33 |
| 6 | 0.32 |
| 7 | 0.33 |
| 8 | 0.32 |
| 9 | 0.12 |
| 10 | 0.3 |

Since the antibody-producing cells thus obtained always produce the antibodies of the present invention, i.e., anti-human Exon-17 monoclonal antibodies, the supernatant of the culture in which these antibody-producing cells were cultured can be directly used as the antibody solution of the present invention. It is to be noted that the above antibody-producing cell line (hybridoma) No. 1 (SBM337), which produces anti-human Exon-17 monoclonal antibody, was deposited, pursuant to the Budapest Treaty, under FERM BP-10718 on Nov. 1, 2006 with the International Patent Organism Depositary, the National Institute of Advanced Industrial Science and Technology AIST Tsukuba Central 6, 1-1, Higashi 1-chome, Tsukuba-shi, Ibaraki-Ken 305-8566, Japan.

(7) Confirmation of Binding Capacity to Human Periostin Protein (PN-1)

Antibodies produced by the 10 antibody-producing cells obtained in (6) were confirmed for their binding capacity to human periostin protein (PN-1) by dot blotting. Namely, the synthetic protein obtained in Example 8 (30 µg/ml) was spotted in 5 µl volumes on a Hybond-ECL nitrocellulose membrane (GE Healthcare Bio-Sciences KK) and washed once with TBS solution (10 mM Tris-HCl (pH8.0), 150 mM NaCl). Blocking buffer (Block Ace, Snow Brand Milk Products Co., Ltd.) was added and shaken at room temperature for 1 hour. After a 1 µg/ml solution of each monoclonal antibody (primary antibody) obtained in (6) was added to the membrane and shaken for 3 hours, the membrane was washed four times with TBS solution under shaking for 10 minutes. After a 0.4 µg/ml solution of an HRP-labeled anti-mouse IgG antibody (Promega) (secondary antibody) was added to the membrane and shaken at room temperature for 1 hour, the membrane was washed four times with TBS solution under shaking for 10 minutes. Detection reagents (ECL plus western blotting detection system, GE Healthcare Bio-Sciences KK) were added and reacted for 1 minute to detect chemiluminescence. As a result, it was confirmed that all of the 10 antibody-producing cells cloned in (6) bind to human periostin PN-1.

(8) Mass Production and Purification of Monoclonal Antibody

BALB/c mice were intraperitoneally administered with pristane [2,6,10,14-tetramethyl pentadecane (0.5 ml, Wako Pure Chemical Industries, Ltd.) and kept for 2 to 3 weeks. The monoclonal antibody-producing hybridomas No. 1 and No. 3 which had been maintained at the logarithmic growth phase were collected and centrifuged to remove the culture supernatant. To the cells in each pellet fraction, FCS-free RPMI medium was added to prepare a cell suspension at a cell density of $1 \times 10^7$ cells/ml. This cell suspension was intraperitoneally injected into the BALB/c mice pretreated with pristane and, after about three weeks, the exuded ascites fluid was collected from the abdominal region by a syringe. After each collected ascites fluid was filtered using a filter with a pore size of φ0.22 µm, the filtrates were purified in a routine manner by affinity chromatography on a Protein G-sepharose column (Millipore, 11511324) to prepare two anti-human Exon-17 monoclonal antibodies.

Example 10

Recognition Site Analysis of Anti-human Exon-17 Monoclonal Antibody in Human Periostin Exon-17 Peptide Chain The resulting two monoclonal antibodies (No. 1 and No. 3) were analyzed for their recognition sites in the human periostin Exon-17 peptide chain (epitope identification). Namely, based on an amino acid sequence consisting of 45 amino acids in total between the -9th phenylalanine from the N-terminus and the 9th isoleucine from the C-terminus of the human periostin Exon-17 peptide chain (SEQ ID NO: 4; the 1st threonine up to the 27th glutamic acid), the following 36 peptides composed of 10 amino acids were synthesized on a cellulose membrane to prepare a membrane-bound peptide array (custom SPOTs service of Sigma-Aldrich Japan K.K.).

```
1      FKEIPVTVYT      (SEQ ID NO: 35)

2      KEIPVTVYTT      (SEQ ID NO: 36)

3      EIPVTVYTTK      (SEQ ID NO: 37)
```

-continued

| | | |
|---|---|---|
| 4 | IPVTVYTTKI | (SEQ ID NO: 38) |
| 5 | PVTVYTTKII | (SEQ ID NO: 39) |
| 6 | VTVYTTKIIT | (SEQ ID NO: 40) |
| 7 | TVYTTKIITK | (SEQ ID NO: 41) |
| 8 | VYTTKIITKV | (SEQ ID NO: 42) |
| 9 | YTTKIITKVV | (SEQ ID NO: 43) |
| 10 | TTKIITKVVE | (SEQ ID NO: 44) |
| 11 | TKIITKVVEP | (SEQ ID NO: 45) |
| 12 | KIITKVVEPK | (SEQ ID NO: 46) |
| 13 | IITKVVEPKI | (SEQ ID NO: 47) |
| 14 | ITKVVEPKIK | (SEQ ID NO: 48) |
| 15 | TKVVEPKIKV | (SEQ ID NO: 49) |
| 16 | KVVEPKIKVI | (SEQ ID NO: 50) |
| 17 | VVEPKIKVIE | (SEQ ID NO: 51) |
| 18 | VEPKIKVIEG | (SEQ ID NO: 52) |
| 19 | EPKIKVIEGS | (SEQ ID NO: 53) |
| 20 | PKIKVIEGSL | (SEQ ID NO: 54) |
| 21 | KIKVIEGSLQ | (SEQ ID NO: 55) |
| 22 | IKVIEGSLQP | (SEQ ID NO: 56) |
| 23 | KVIEGSLQPI | (SEQ ID NO: 57) |
| 24 | VIEGSLQPII | (SEQ ID NO: 58) |
| 25 | IEGSLQPIIK | (SEQ ID NO: 59) |
| 26 | EGSLQPIIKT | (SEQ ID NO: 60) |
| 27 | GSLQPIIKTE | (SEQ ID NO: 61) |
| 28 | SLQPIIKTEG | (SEQ ID NO: 62) |
| 29 | LQPIIKTEGP | (SEQ ID NO: 63) |
| 30 | QPIIKTEGPT | (SEQ ID NO: 64) |
| 31 | PIIKTEGPTL | (SEQ ID NO: 65) |
| 32 | IIKTEGPTLT | (SEQ ID NO: 66) |
| 33 | IKTEGPTLTK | (SEQ ID NO: 67) |
| 34 | KTEGPTLTKV | (SEQ ID NO: 68) |
| 35 | TEGPTLTKVK | (SEQ ID NO: 69) |
| 36 | EGPTLTKVKI | (SEQ ID NO: 70) |

This membrane was allowed to stand in a small volume of methanol for 5 minutes and was then washed three times with TBS solution. Blocking buffer (casein, included in SPOTs) was added and stirred at room temperature for 2 hours. After a 1 μg/ml solution of each monoclonal antibody (primary antibody) obtained in Example 9(8) was added to the membrane and shaken for 3 hours, the membrane was washed three times in TBS solution under shaking for 10 minutes. After a 0.4 μg/ml solution of an HRP-labeled anti-mouse IgG antibody (Promega) (secondary antibody) was added to the membrane and incubated for 2 hours, the membrane was washed three times with TBS solution under shaking for 5 minutes. Detection reagents (SuperSignal West Pico, Pierce) were added and reacted for 1 minute to detect chemiluminescence. As a result, monoclonal antibodies No. 1 and No. 3 were found to react with and bind to only synthetic peptide No. 9 consisting of the amino acid sequence YTTKIITKVV (SEQ ID NO: 26), i.e., a peptide consisting of an amino acid sequence covering from the −1st tyrosine to the 9th valine from the N-terminus of the amino acid sequence of the human periostin Exon-17 peptide chain (SEQ ID NO: 4) or covering from the 669th tyrosine to the 678th valine from the N-terminus of the amino acid sequence of human periostin PN-1 (SEQ ID NO: 2).

Example 11

Recognition Site Analysis of Anti-rat Exon-17 Polyclonal Antibody in Human Periostin Exon-17 Peptide Chain In the same manner as shown in Example 10, the polyclonal antibody prepared in Example 1 was analyzed for its recognition site in the human periostin Exon-17 peptide chain (epitope identification). As a result, as in the case of the monoclonal antibodies in Example 10, the polyclonal antibody was found to react with only synthetic peptide No. 9, indicating that the polyclonal antibody specifically recognizes the same site as the monoclonal antibodies. This suggests that antibodies having the same specificity are obtainable in both cases where a rat periostin Exon-17 peptide is used as an antigen to prepare a polyclonal antibody and where a human periostin Exon-17 peptide is used as an antigen to prepare a monoclonal antibody.

Example 12

Confirmation of Binding Capacity to Rat Periostin Protein (PN-1)

The resulting two monoclonal antibodies (No. 1 and No. 3) were confirmed for their binding capacity to rat periostin protein (PN-1) by dot blotting. Namely, the purified protein obtained in Preparation example 6 (30 μg/ml) was spotted in 5 μl volumes on a Hybond-ECL nitrocellulose membrane (GE Healthcare Bio-Sciences KK) and washed once with TBS solution (10 mM Tris-HCl (pH8.0), 150 mM NaCl). Blocking buffer (Block Ace, Snow Brand Milk Products Co., Ltd.) was added and shaken at room temperature for 1 hour. After a 1 μg/ml solution of each monoclonal antibody (primary antibody) was added to the membrane and shaken for 3 hours, the membrane was washed four times with TBS solution under shaking for 10 minutes. After a 0.4 μg/ml solution of an HRP-labeled anti-mouse IgG antibody (Promega) (secondary antibody) was added to the membrane and shaken at room temperature for 1 hour, the membrane was washed four times with TBS solution under shaking for 10 minutes. Detection reagents (ECL plus western blotting detection system, GE Healthcare Bio-Sciences KK) were added and reacted for 1 minute to detect chemiluminescence. As a result, it was confirmed that the resulting two monoclonal antibodies also bind to rat periostin PN-1.

Example 13

Epitope Analysis of Anti-human Exon-17 Monoclonal Antibody

The results of Example 10 indicated that the epitope site of each anti-human Exon-17 monoclonal antibody recognizes an amino acid sequence (TTKIITKVV; SEQ ID NO: 22) covering from the N-terminal threonine to the 9th valine of the human periostin Exon-17 peptide chain (SEQ ID NO: 4). Likewise, the results of Example 12 confirmed that each anti-human Exon-17 monoclonal antibody also binds to rat periostin protein (PN-1). These results suggested that the epitope site of each anti-human Exon-17 monoclonal antibody recognizes a region, whose amino acids do not differ between humans and rats, in the amino acid sequence (TTKIITKVV; SEQ ID NO: 22) covering from the N-terminal threonine to the 9th valine of the human periostin Exon-17 peptide chain (SEQ ID NO: 4), i.e., the entire amino acid sequence, or a part thereof, which covers from the N-terminal threonine to the 7th lysine of the human periostin Exon-17 peptide chain (SEQ ID NO: 4) or the rat periostin Exon-17 peptide chain (SEQ ID NO: 3). Thus, for further analysis of the epitope site, alanine scanning was performed.

Based on an amino acid sequence (YTTKIITKVV; SEQ ID NO: 26) covering from the −1st tyrosine to the 9th valine from the N-terminus of the human periostin Exon-17 peptide chain (SEQ ID NO: 4), the following 10 peptides modified to replace some amino acids by alanines were synthesized at a purity of 80% or more.

| #1  | YTTKIITKVV | (SEQ ID NO: 71) |
| #2  | ATTKIITKAA | (SEQ ID NO: 72) |
| #3  | AATKIITKAA | (SEQ ID NO: 73) |
| #4  | AAAKIITKAA | (SEQ ID NO: 74) |
| #5  | AAAAIITKAA | (SEQ ID NO: 75) |
| #6  | AAAAAITKAA | (SEQ ID NO: 76) |
| #7  | ATTKIITAAA | (SEQ ID NO: 77) |
| #8  | ATTKIIAAAA | (SEQ ID NO: 78) |
| #9  | ATTKIAAAAA | (SEQ ID NO: 79) |
| #10 | ATTKAAAAAA | (SEQ ID NO: 80) |

The synthetic peptides (1 mg each) were solubilized with 50 µl PBS(−), spotted in 1.5 µl volumes on a Hybond-ECL nitrocellulose membrane (GE Healthcare Bio-Sciences KK) and washed once with TBS solution. Blocking buffer (Block Ace, Snow Brand Milk Products Co., Ltd.) was added and shaken at room temperature for 1 hour. After a 1 µg/ml solution of each monoclonal antibody (primary antibody) obtained in Example 9(8) was added to the membrane and shaken for 3 hours, the membrane was washed four times with TBS solution under shaking for 10 minutes. After a 0.4 µg/ml solution of an HRP-labeled anti-mouse IgG antibody (Promega) (secondary antibody) was added to the membrane and shaken at room temperature for 1 hour, the membrane was washed four times with TBS solution under shaking for 10 minutes. Detection reagents (SuperSignal West Pico, Pierce) were added and reacted for 1 minute to detect chemiluminescence.

As a result, the monoclonal antibodies were found to strongly react with synthetic peptide #7 shown above (a peptide comprising alanine substitutions at the 1st and the 8-10th amino acids from the N-terminus of a peptide consisting of an amino acid sequence (YTTKIITKVV; SEQ ID NO: 26) covering from the −1st tyrosine to the 9th valine from the N-terminus of the human periostin Exon-17 peptide chain (SEQ ID NO: 4)), weakly react with synthetic peptides #1 (a peptide consisting of an amino acid sequence (YTTKIITKVV; SEQ ID NO: 26) covering from the −1st tyrosine to the 9th valine from the N-terminus of the human periostin Exon-17 peptide chain (SEQ ID NO: 4)) and #2 (a peptide comprising alanine substitutions at the 1st and the 9-10th amino acids from the N-terminus of a peptide consisting of an amino acid sequence (YTTKIITKVV; SEQ ID NO: 26) covering from the −1st tyrosine to the 9th valine from the N-terminus of the human periostin Exon-17 peptide chain (SEQ ID NO: 4)), and more weakly react with synthetic peptides #3 (a peptide comprising alanine substitutions at the 1st, the 2nd and the 9-10th amino acids from the N-terminus of a peptide consisting of an amino acid sequence (YTTKIITKVV; SEQ ID NO: 26) covering from the −1st tyrosine to the 9th valine from the N-terminus of the human periostin Exon-17 peptide chain (SEQ ID NO: 4)) and #8 (a peptide comprising alanine substitutions at the 1st and the 7-10th amino acids from the N-terminus of a peptide consisting of an amino acid sequence (YTTKIITKVV; SEQ ID NO: 26) covering from the −1st tyrosine to the 9th valine from the N-terminus of the human periostin Exon-17 peptide chain (SEQ ID NO: 4)).

Example 14

Recognition Site Analysis of Anti-rat Exon-17 Polyclonal Antibody in Human Periostin Exon-17 Peptide Chain In the same manner as shown in Example 13, the polyclonal antibody prepared in Example 1 was analyzed for its recognition site in the human periostin Exon-17 peptide chain (epitope identification). As a result, as in the case of the monoclonal antibodies in Example 13, the polyclonal antibody was found to strongly react with synthetic peptide #7, weakly react with synthetic peptides #1 and #2, and still more weakly react with synthetic peptides #3 and #8, indicating that the polyclonal antibody specifically recognizes the same site as the monoclonal antibodies. This suggests that antibodies having the same specificity are obtainable in both cases where a rat periostin Exon-17 peptide is used as an antigen to prepare a polyclonal antibody and where a human periostin Exon-17 peptide is used as an antigen to prepare a monoclonal antibody.

Example 15

In vitro Study of the Presence or Absence of Anti-Cell Adhesive Activity of Human Periostin Protein (Human PN-1)

Figure 10:
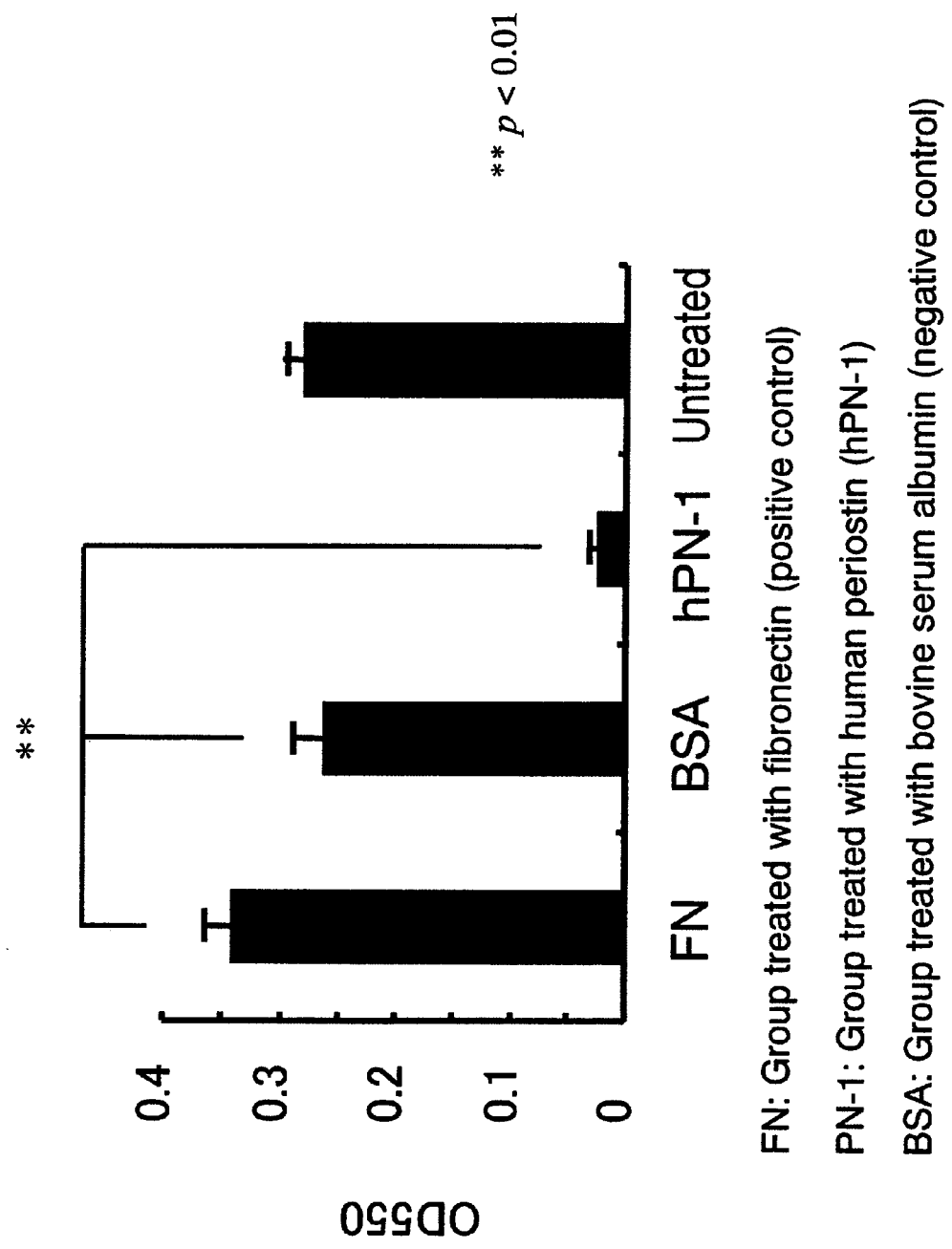
FIG. 10 is a diagram showing assay results of the anti-cell adhesive properties of human PN-1 (Example 15).

In the same manner as shown in Example 2, human heart fibroblasts (Dainippon Pharmaceutical Co., Ltd., catalog No. CS-ABI-5118) were plated on a 96-well plate at a density of $6.4 \times 10^4$ cells/100 µl and cultured overnight, and then the culture was incubated in fresh CSC medium (Cell System Corporation) with 10% FBS containing 10 µg/ml cycloheximide at 37° C. for 1 hour. Then, the cells were washed twice with CSC medium (serum free) prewarmed at 37° C., and human periostin protein (human PN-1) prepared according to the Examples was added to CSC medium (serum free) at a final concentration of 1 µg/ml. Fibronectin having cell adhesion-promoting properties was used as a positive control and BSA (bovine serum albumin) having no cell adhesive properties was used as a negative control. After incubation at 37° C. for 3.5 hours, microscopy showed that all the cells were separated in the group treated with human periostin protein, and the cells were washed twice with PBS (−) and then fixed in 10% neutral buffered formalin for 30 minutes. Then, the cells were washed with PBS (−) three times and then stained with crystal violet for 30 minutes. Then, the degree of staining was measured using a plate reader at 550 nm (BIO-RAD, Model 680 MICRO PLATE READER) (FIG. 10). As a result, the control groups treated with fibronectin and BSA and the untreated group did not show anti-cell adhesive properties, in contrast to the group treated with human periostin protein (human PN-1) in which the cells were separated, showing that human periostin protein (human PN-1) has anti-cell adhesive properties.

Example 16

Figure 11:
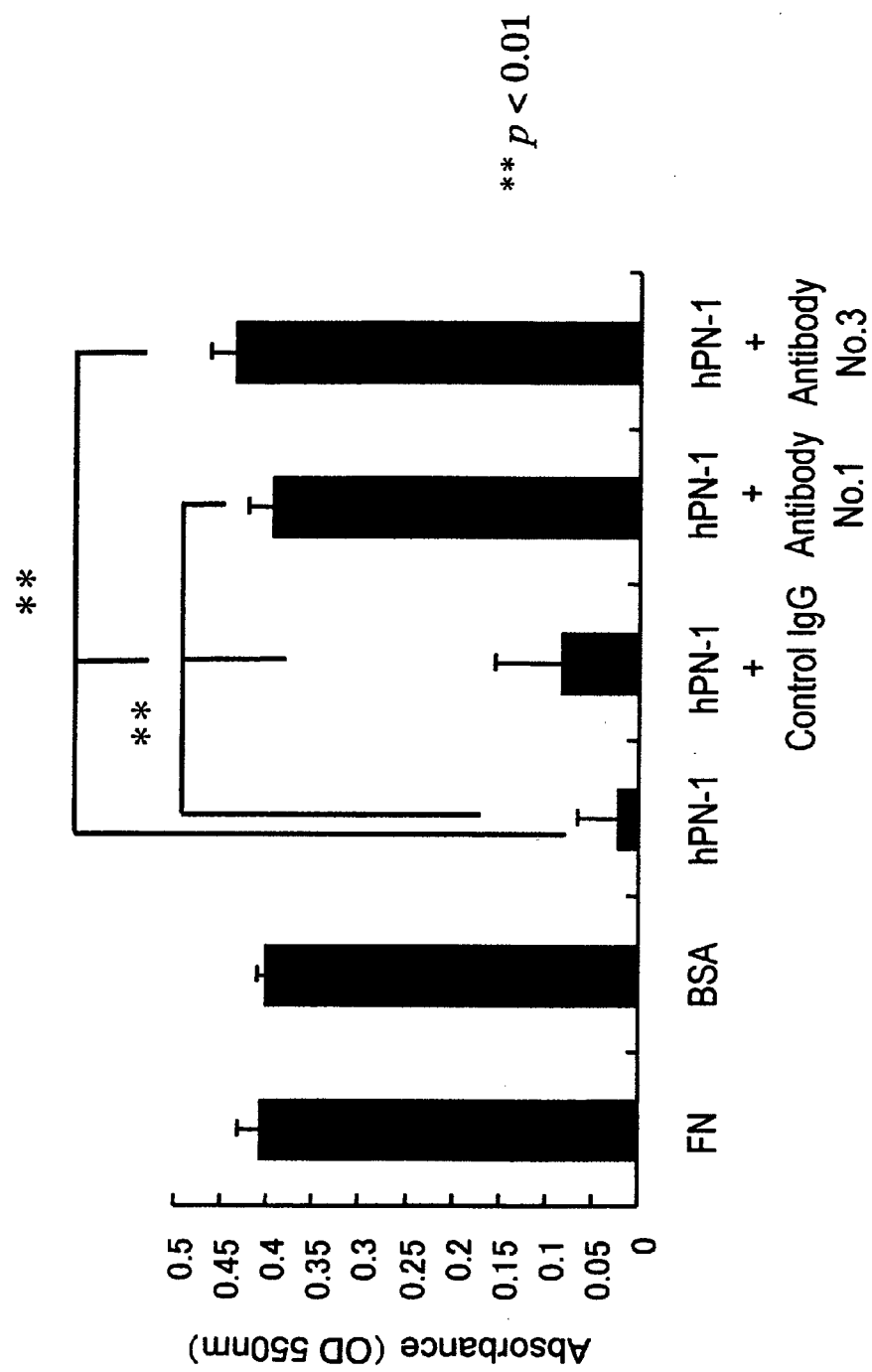
FIG. 11 is a diagram showing assay results of the inhibition of human PN-1 activity by anti-human Exon-17 monoclonal antibody (Example 16).

In vitro Study of the Neutralizing Activity of Anti-human Exon-17 Monoclonal Antibody In the same manner as shown in Example 3, human heart fibroblasts were plated on a 96-well plate at a density of $6.4 \times 10^4$ cells/100 µl and cultured overnight, and then the culture was incubated in fresh CSC medium with 10% FBS containing 10 µg/ml cycloheximide at 37° C. for 1 hour. Then, the cells were washed twice with CSC medium (serum free) prewarmed at 37° C., and human periostin protein (human PN-1) and anti-human Exon-17 monoclonal antibody (No. 1 or No. 3) were added to CSC medium (serum free) at final concentrations of 1 µg/ml and 200 µg/ml, respectively. Human periostin protein (human PN-1) alone was used as a positive control and BSA was used as a negative control. After incubation at 37° C. for 3.5 hours, microscopy showed that all the cells were separated in the group treated with human periostin protein (human PN-1) alone, and the cells were washed twice with PBS (−) and then fixed in 10% neutral buffered formalin for 30 minutes. Then, the cells were washed with PBS (−) three times and then stained with crystal violet for 30 minutes. Then, the degree of staining was measured using a plate reader at 550 nm (BIO-RAD, Model 680 MICRO PLATE READER) (FIG. 11). The results showed that anti-human Exon-17 monoclonal antibodies are antibodies having the activity of inhibiting the anti-cell adhesive properties of human periostin protein (human PN-1), i.e., neutralizing the anti-cell adhesive properties of human periostin protein (human PN-1).

As shown above, the anti-cell adhesive properties of human periostin protein (human PN-1) were inhibited by antibodies against Exon-17 of human periostin protein (human PN-1) which specifically recognize a sequence or a part thereof consisting of the N-terminal 1st to 6th amino acids of Exon-17, suggesting that Exon-17, at least a peptide segment or a part thereof consisting of the N-terminal 1st to 6th amino acids of Exon-17 constitutes a region related to the anti-cell adhesive properties of human periostin protein (human PN-1).

Example 17

Effect of Anti-human Exon-17 Monoclonal Antibody on Acute Myocardial Infarction Model Rats In the same manner as shown in Example 4, a male Lewis rat weighing 250-300 g was fixed on a rat surgical table after the animal was thoroughly anesthetized by peritoneal administration of pentobarbital (0.1 ml/100 g). A tube was orally inserted into the trachea and connected to a rat ventilator (tidal volume 3 ml, 80 breaths/min), and the skin was laterally incised from the left third intercostal space of the sternum and the underlying greater pectoral muscle was also laterally incised, and the intercostal space was opened using a rat rib spreader to expose the heart.

Then, the left coronary artery nearly beneath the left atrium was ligated with 1.0 silk using a curved needle having a diameter of 5 mm. After visual confirmation that the anterior and lateral walls along which the left coronary artery runs have been changed from red to white to show sufficient blockage of the coronary bloodstream and the disappearance of wall motion at these sites (in the sham operation group, the needle was passed through the coronary artery and then removed without ligation), the third and fourth ribs were fixed by ligation with 3.0 silk (after the lung was expanded to remove the air existing outside the lung in the rib cage so that the lung can be easily expanded). The incision site in the skin was sutured with 3.0 silk in the same manner and then observed for a while, and the tube was removed after confirmation of recovery of consciousness and resumption of spontaneous breathing.

Acute myocardial infarction models were sequentially prepared by the foregoing procedure.

On the following day, percutaneous echocardiography was performed under intranasal anesthesia with isoflurane, and small infarction models having an infarction size less than 20% of the entire periphery of the left ventricle were excluded. The remaining infarction models were ranked in order of increasing heart function, and alternately classified into a group treated with anti-human Exon-17 monoclonal antibody (No. 3) and a group treated with a control antibody (rabbit IgG) each 200 µg via tail vein.

The antibodies were administered to each group on the day following the preparation of the models and at intervals of 6 days after the initial administration, a total of 4 times.

Figures 1, 12:
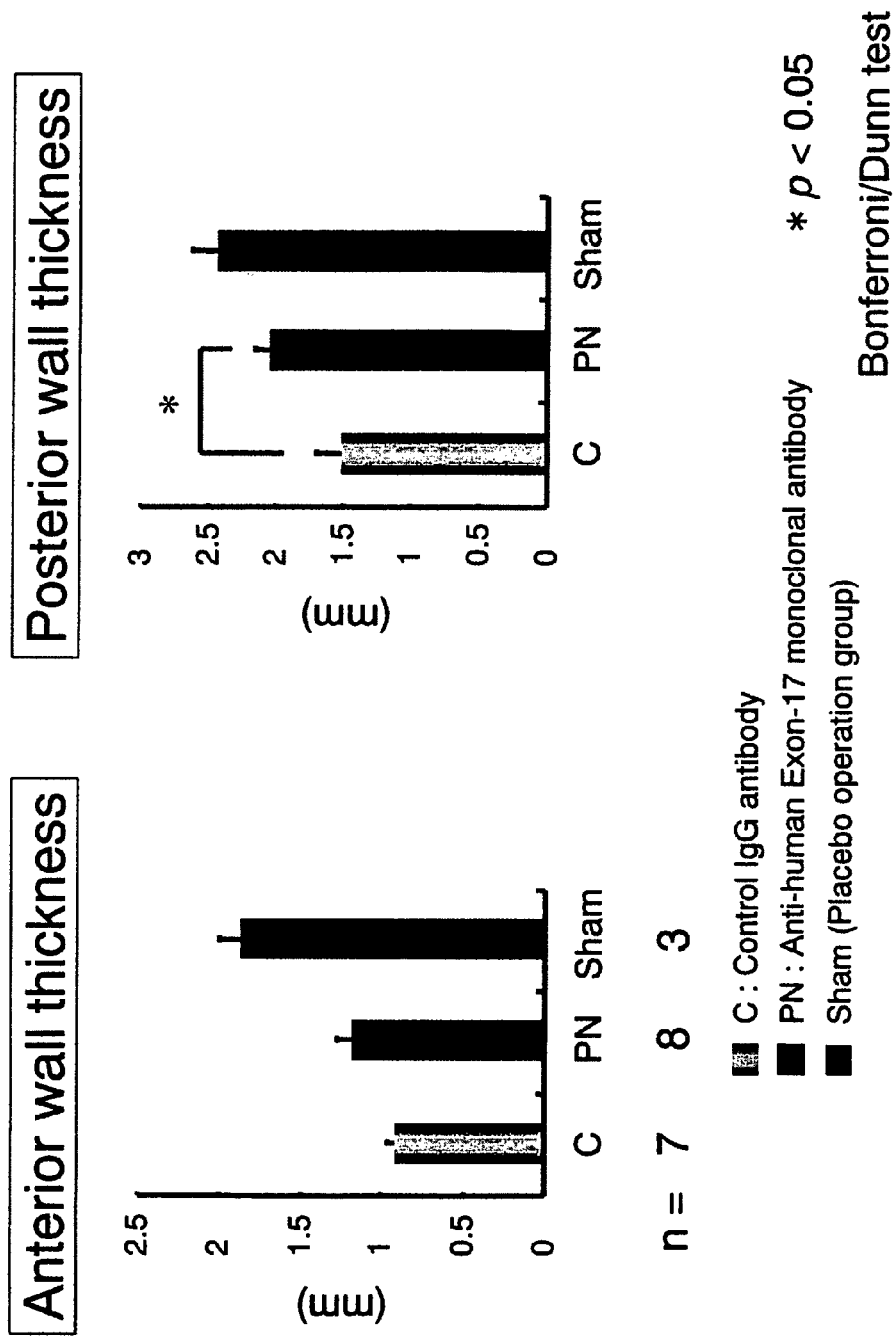
Figures 2, 12:
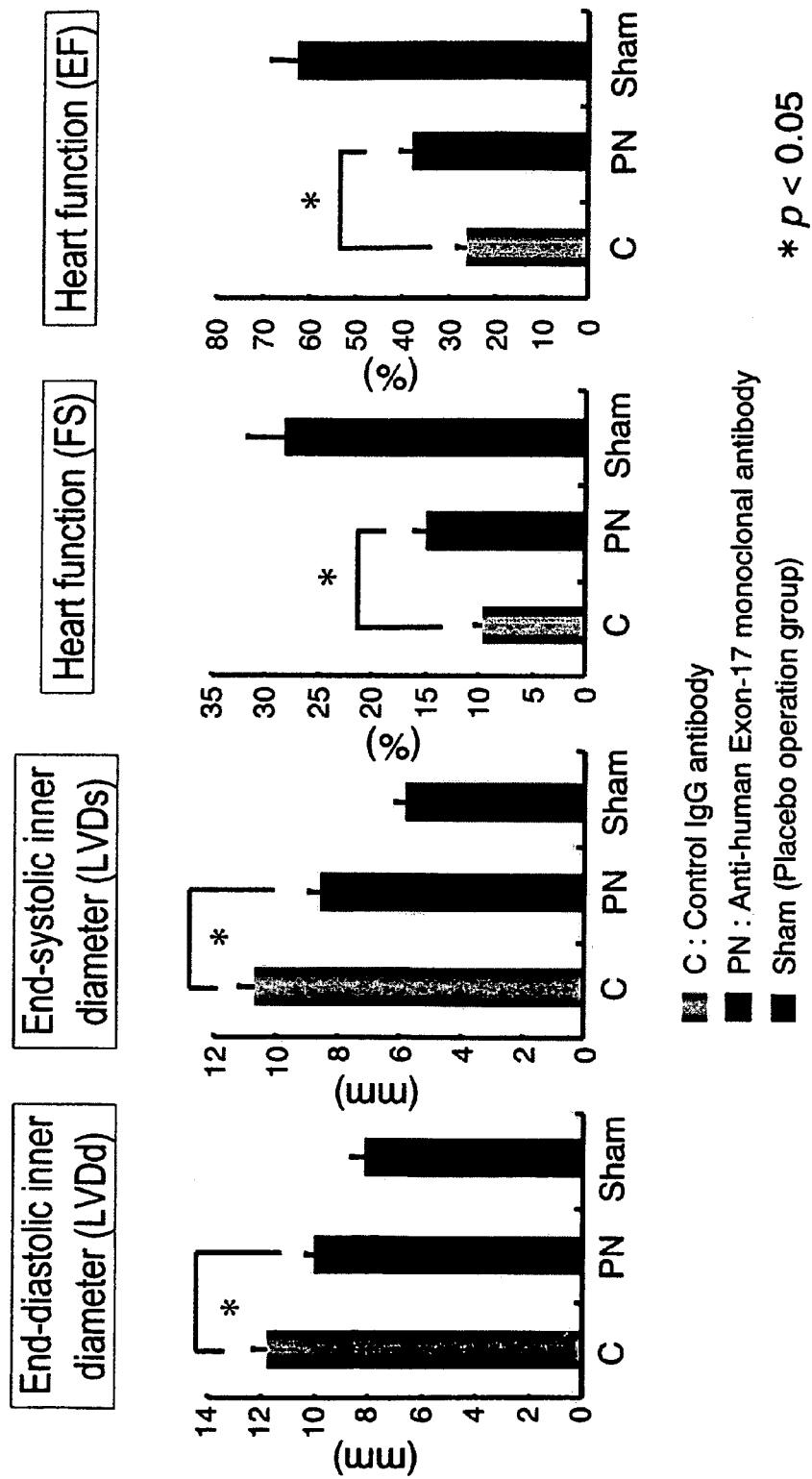
Figures 3, 12:
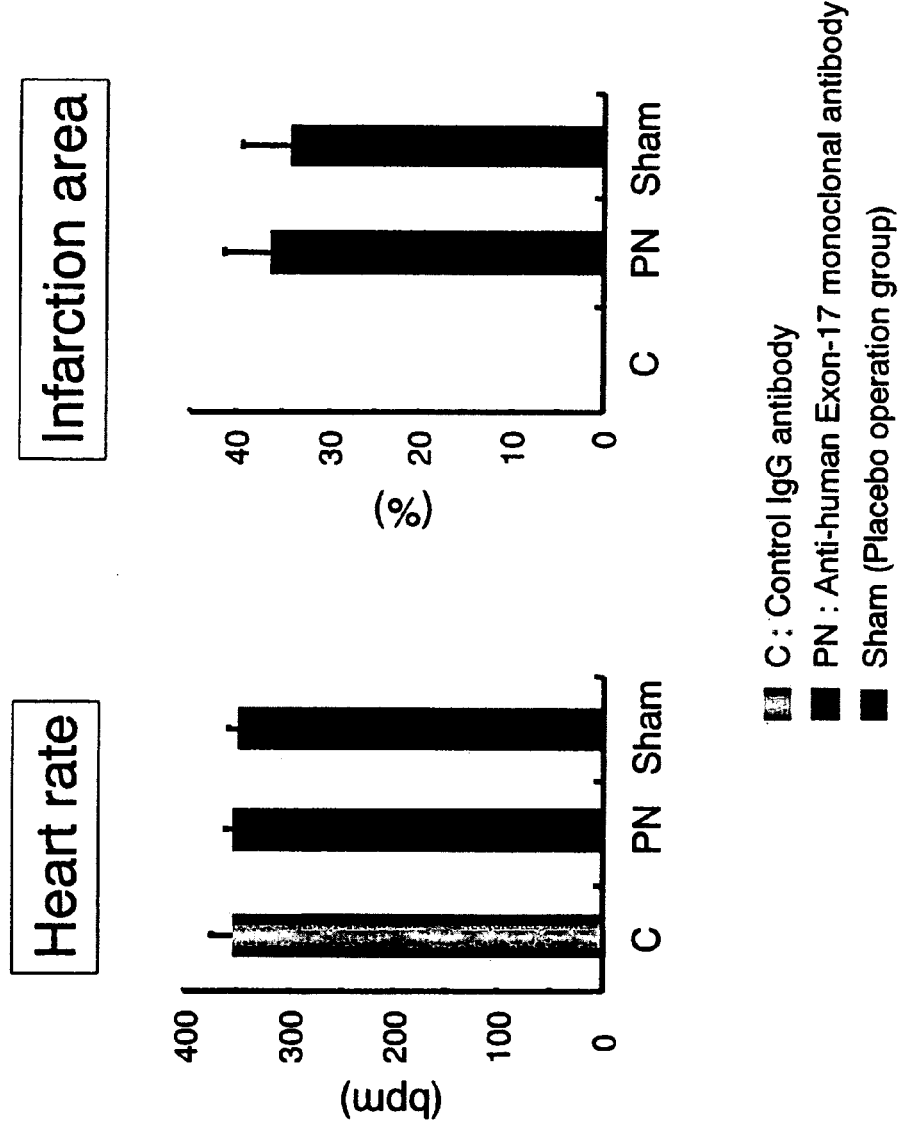

The heart was evaluated by echocardiography through the chest wall at intervals of one week until the end of 4 weeks. The results of echocardiography 4 weeks after the preparation of the models showed that the reduction of the anterior wall thickness and posterior wall thickness of the heart was inhibited, the increase of the end-diastolic inner diameter and end-systolic inner diameter was inhibited, and that the FS value or EF value indicative of the contractile function of the heart increased in the group treated with anti-human Exon-17 monoclonal antibody significantly as compared with the control group treated with rabbit IgG. In brief, heart dilation was inhibited, showing that heart function was improved (FIG. 12-1 to FIG. 12-3).

As shown above, in acute myocardial infarction model rats, effects of inhibiting heart dilation and improving heart function were caused by antibodies against Exon-17 of human periostin protein (human PN-1) which have an epitope composed of at least a sequence consisting of the N-terminal 1st to 6th amino acids of Exon-17, suggesting that Exon-17 of human periostin protein (human PN-1), especially a region comprising at least a peptide segment consisting of the N-terminal 1st to 6th amino acids of Exon-17 is a region related to heart dilation and reduced heart function following myocardial infarction.

Example 18

Figure 13:
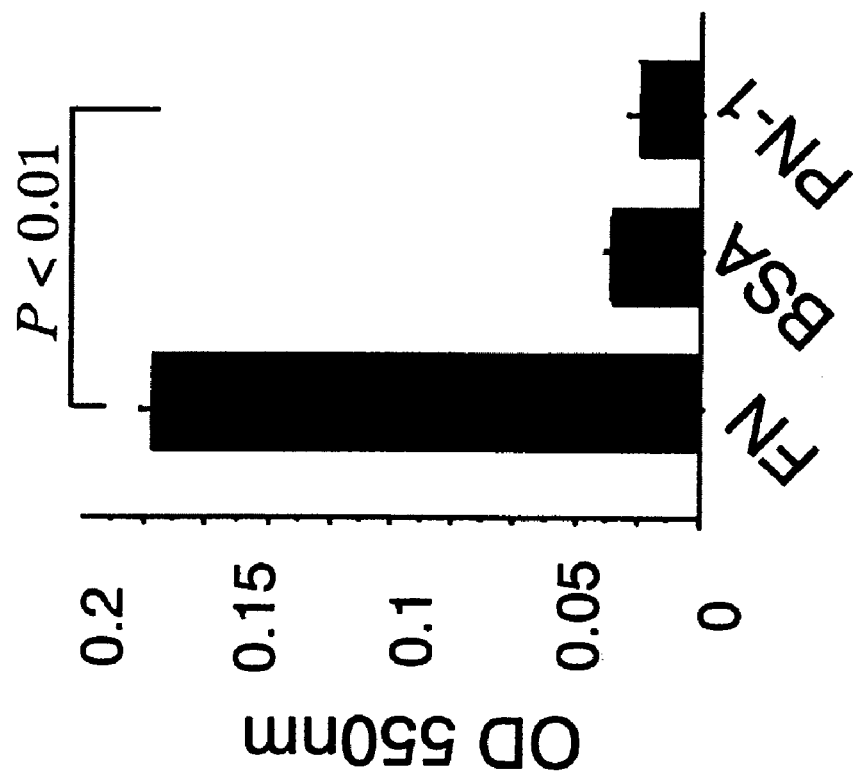
FIG. 13 is a diagram showing assay results of the non-cell adhesive properties of rat PN-1 protein (Example 18).

In vitro Study of the Presence or Absence of Non-cell Adhesive Activity of Rat PN-1 Protein To a 96-well cell culture multiwell plate, 10 µg/ml fibronectin, 100 µg/ml BSA or 10 µg/ml PN-1 protein was added and coated overnight at 4° C. After removal of the protein solution from the wells, mouse melanoma B16-F10 cells (ATCC No. CRL-6475) suspended in DMEM (10% BSA, PC: penicillin, SM: streptomycin) were added at $10^4$ cells/well and cultured in a 37° C. incubator for 3 hours. The level of cell adhesion was measured as follows. After removal of the culture supernatant, the cells were fixed in 2.5% glutaraldehyde for 30 minutes, stained with 0.02% crystal violet and then measured for their absorbance at OD 550 nm with a plate reader (BIO-RAD, Model 680 MICRO PLATE READER). Untreated wells were stained as background samples and used to correct the absorbance values for comparison purposes. Data analysis was made by the Fisher's PLSD test (FIG. 13). As a result, the positive control fibronectin showed cell adhesion, whereas the negative control BSA showed no cell adhesion. The group treated with rat PN-1 protein showed no cell adhesion, indicating that rat PN-1 protein has the effect of preventing cells from adhering, i.e., non-cell adhesive properties.

Example 19

Figure 14:
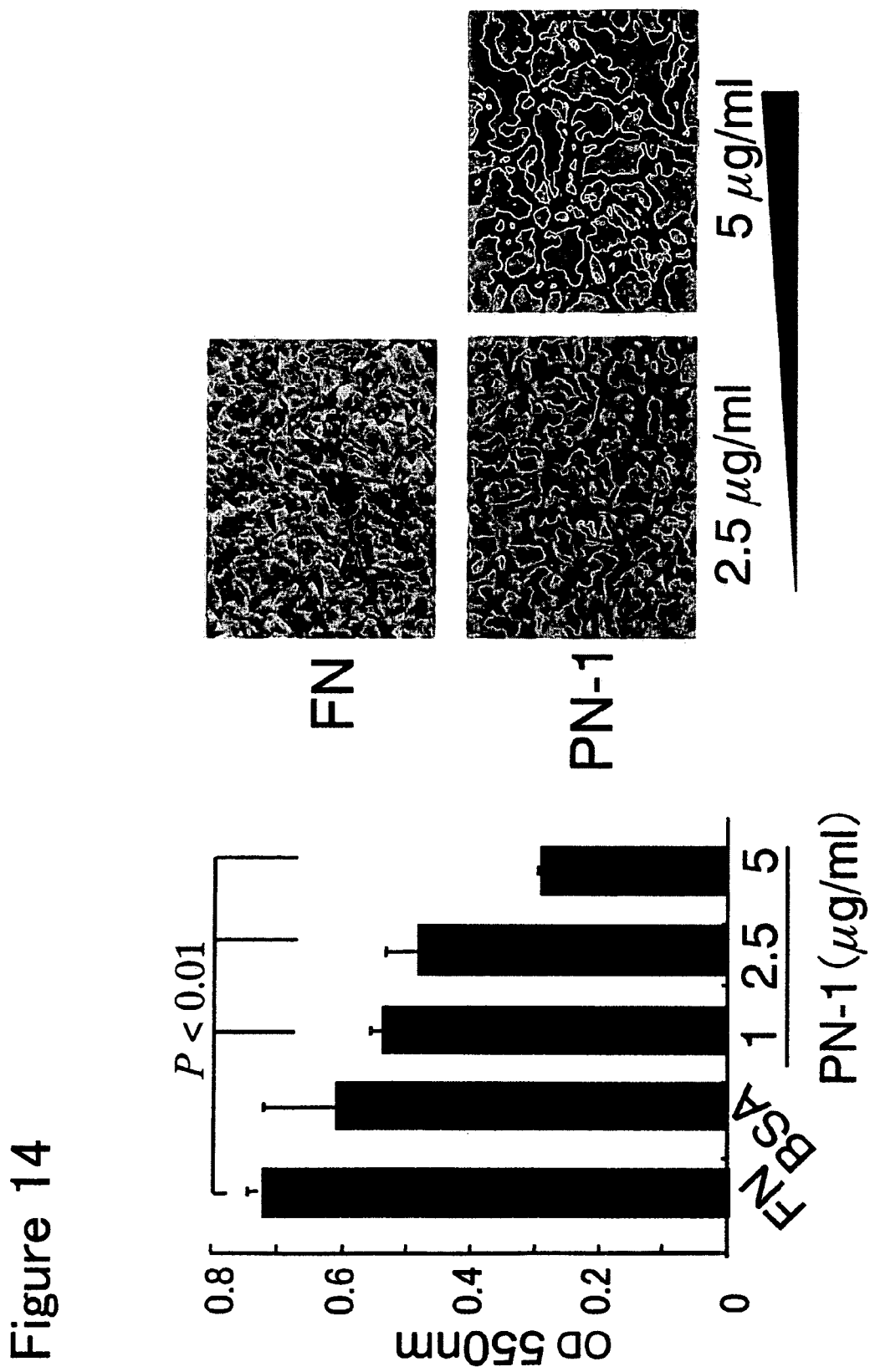
FIG. 14 is a diagram showing assay results of the anti-cell adhesive properties of rat PN-1 protein (Example 19).

In vitro Study of the Presence or Absence of Anti-cell Adhesive Activity of Rat PN-1 Protein To a 96-well cell culture multiwell plate, mouse melanoma B16-F10 cells suspended in DMEM (10% BSA, PC: penicillin, SM: streptomycin) were added at $10^4$ cells/well and cultured overnight in a 37° C. incubator. After removal of the culture supernatant, 10 µg/ml fibronectin (SIGMA), 100 µg/ml BSA (SIGMA) or PN-1 protein was added and cultured in a 37° C. incubator for 1 to 3 hours. The level of cell adhesion was measured as follows. After removal of the culture supernatant, the cells were fixed in 2.5% glutaraldehyde for 30 minutes, stained with 0.02% crystal violet and then measured for their absorbance at OD 550 nm with a plate reader (BIO-RAD, Model 680 MICRO PLATE READER). Untreated wells were stained as background samples and used to correct the absorbance values for comparison purposes. Data analysis was made by the Fisher's PLSD test (FIG. 14). The cells were photographed with a Nikon COOLPIX4500 attached to a stereoscopic microscope LEICA MZ16. As a result, the control groups treated with fibronectin and BSA and the untreated group did not show anti-cell adhesive properties because the adhered cells were not separated, in contrast to the group treated with rat PN-1 protein in which the cells were separated, indicating that rat PN-1 protein has a separating effect on adhered cells, i.e., anti-cell adhesive properties.

Example 20

Figure 15:
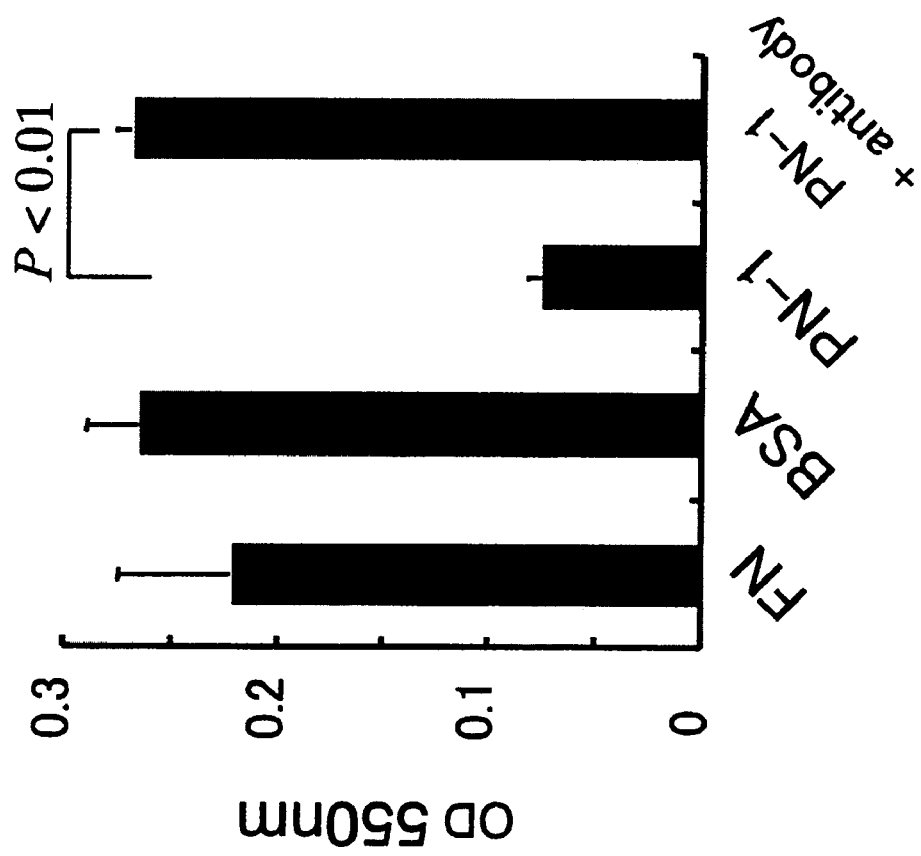
FIG. 15 is a diagram showing assay results of the inhibition of rat PN-1 activity by anti-rat Exon-17 polyclonal antibody (Example 20).

In vitro Study of the Neutralizing Activity of Anti-rat Exon-17 Polyclonal Antibody In the same manner as shown in Example 19, to a 96-well cell culture multiwell plate, mouse melanoma B16-F10 cells suspended in DMEM (10% BSA, PC: penicillin, SM: streptomycin) were added at $10^4$ cells/well and cultured overnight in a 37° C. incubator. After removal of the culture supernatant, the culture was incubated in fresh DMEM medium with 10% FBS containing 10 µg/ml cycloheximide at 37° C. for 1 hour. Then, the cells were washed twice with DMEM medium (serum free) prewarmed at 37° C., and rat periostin protein and anti-rat Exon-17 polyclonal antibody were added to DMEM medium (serum free) at final concentrations of 10 µg/ml and 100 µg/ml, respectively. Rat periostin protein alone was used as a positive control and BSA was used as a negative control. After incubation at 37° C. for 1 hour, microscopy showed that almost all the cells were separated in the group treated with rat periostin protein alone, and the cells were washed twice with PBS(-) and then fixed in 10 neutral buffered formalin for 30 minutes. Then, the cells were washed with PBS(-) three times and then stained with crystal violet for 30 minutes. Then, the degree of staining was measured using a plate reader at 550 nm (BIO-RAD, Model 680 MICRO PLATE READER) (FIG. 15). The results showed that the anti-rat Exon-17 polyclonal antibody is an antibody having the activity of inhibiting PN-1 protein-induced separation of adhered cells, i.e., inhibiting the anti-cell adhesive properties of PN-1 protein, i.e., neutralizing the anti-cell adhesive properties of rat PN-1 protein.

Example 21

Figure 16A:
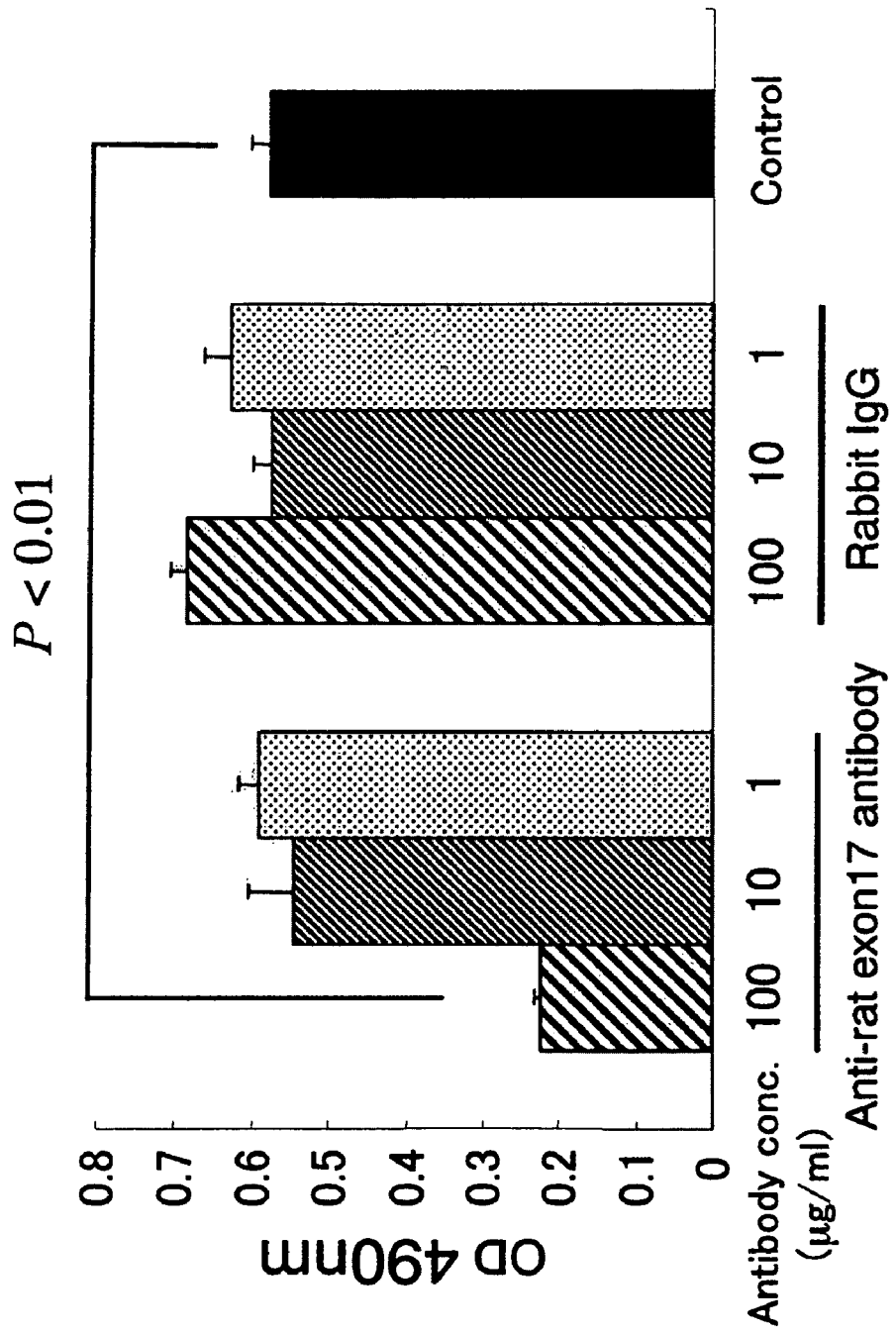
FIG. 16A is a diagram showing assay results of the inhibition of mouse melanoma B16-F10 cell proliferation by anti-rat Exon-17 polyclonal antibody (Example 21).
Figure 16B:
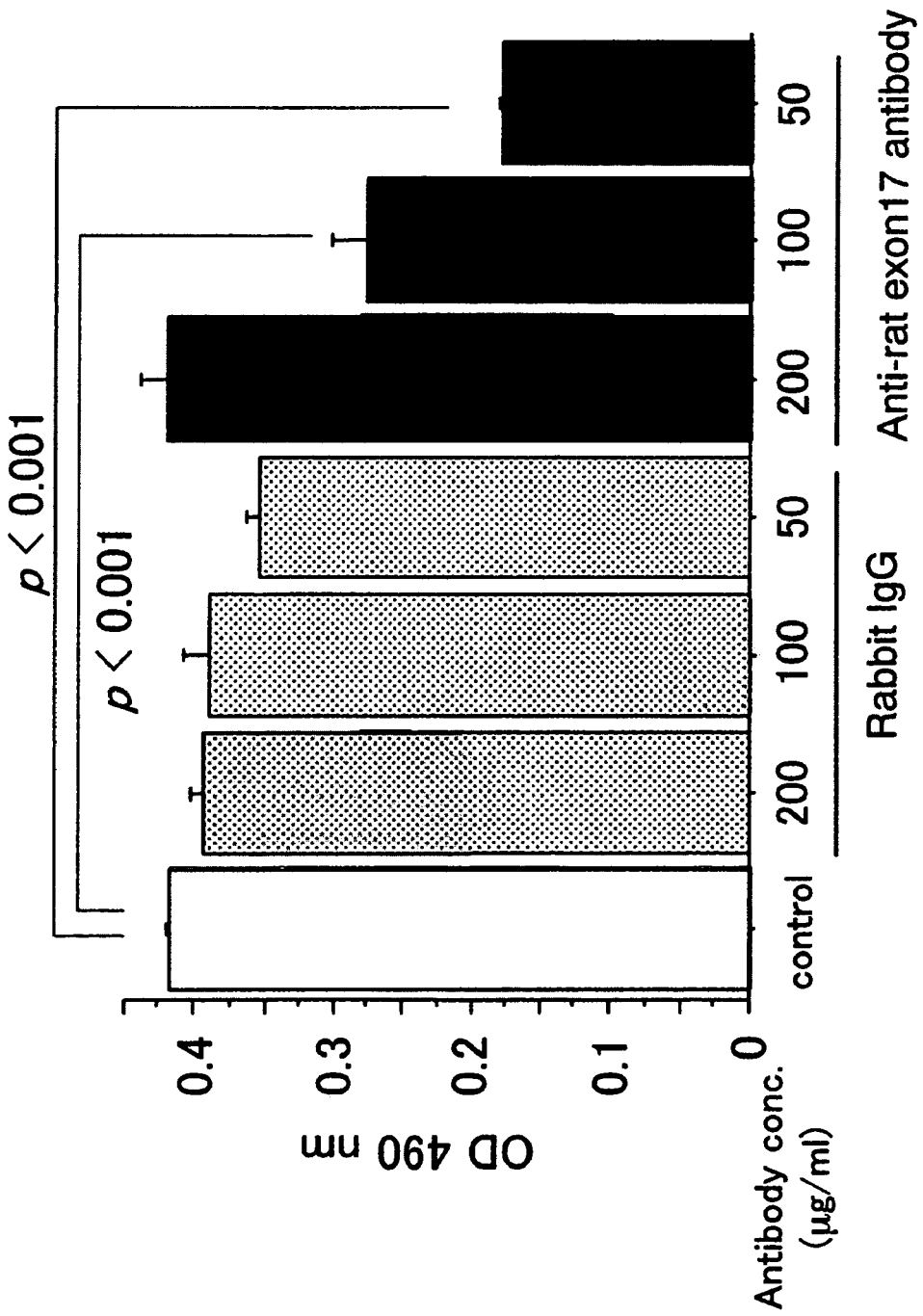
FIG. 16B is a diagram showing assay results of the inhibition of mouse 4T1 breast cancer cell proliferation by anti-rat Exon-17 polyclonal antibody (Example 21).

In vitro Study of the Effect of Anti-rat Exon-17 Polyclonal Antibody on Cell Proliferation In the same manner as shown in Example 19, to a 96-well cell culture multiwell plate, mouse melanoma B16-F10 cells suspended in DMEM (serum free, PC: penicillin, SM: streptomycin) were added at $10^4$ cells/well and cultured overnight in a 37° C. incubator. After removal of the culture supernatant, DMEM (serum free, PC: penicillin, SM: streptomycin) medium supplemented with anti-rat Exon-17 polyclonal antibody and rabbit IgG antibody, each at a final concentration of 100 µg/ml, 10 µg/ml or 1 µg/ml, was added to the cells, and overnight culturing was repeated again. On the following day, the medium in each well was replaced by DMEM (10% BSA, PC: penicillin, SM: streptomycin), and a Cell Titer 96 AQueous One Solution Cell Proliferation Assay kit (Promega) was used to add 20 µl Cell Titer solution per 100 µl medium, followed by incubation at 37° C. for 1 hour. Then, the degree of staining was measured using a plate reader at 490 nm (BIO-RAD, Model 680 MICRO PLATE READER) (FIG. 16A). Similary, in case of mouse 4T1 breast cancer cells, anti-rat Exon-17 polyclonal antibody and rabbit IgG antibody, each at a final concentration of 200 µg/ml, 100 µg/ml or 50 µg/ml, was added to the cells, and then measured (FIG. 16B). The results showed that the anti-rat Exon-17 polyclonal antibody is an antibody having the activity of inhibiting cell proliferation at high concentration.

Example 22

Figure 17:
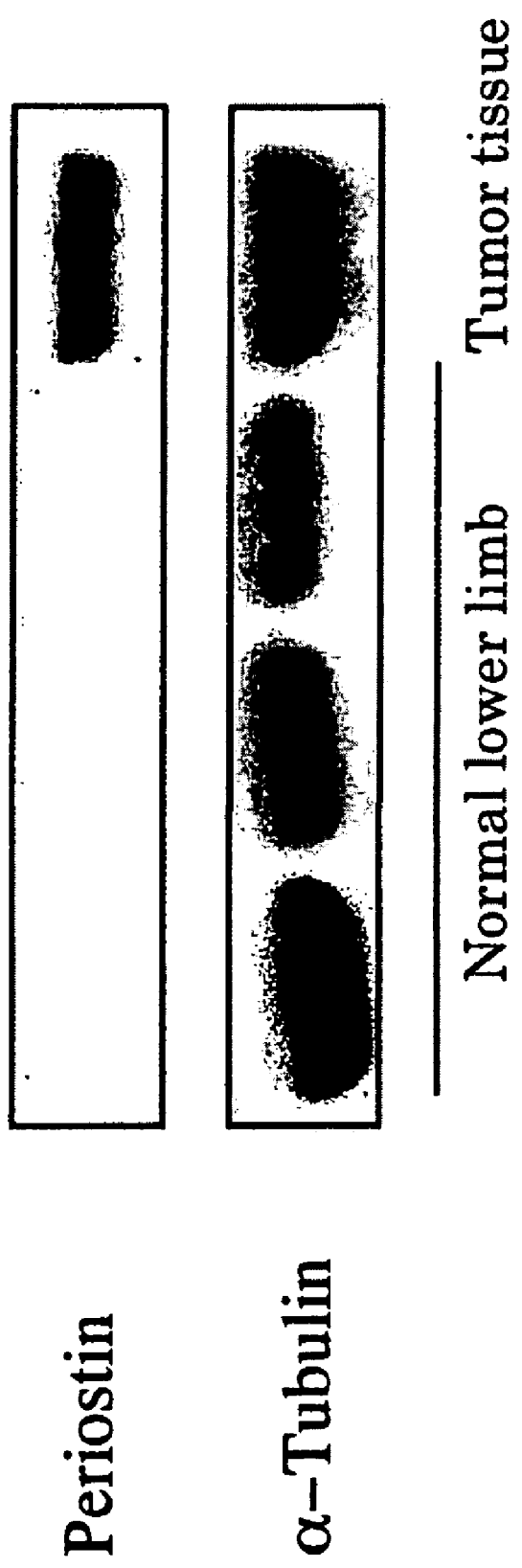
FIG. 17 is a diagram showing periostin expression in primary tumor inoculated with mouse melanoma B16-F10 cells and in normal tissue (Example 22).

Periostin Expression in Primary Tumor Using Model Mice for Lung Metastasis of Mouse Melanoma B16-F10 Cells At 2 weeks after injection of mouse melanoma B16-F10 cells, mouse primary tumors were collected and the homogenized tissue was allowed to stand on ice for 15 minutes after addition of RIPA buffer (RIPA Lyses Buffer 10×; Upstate), 180 mM $Na_3VO_4$, protease inhibitor cocktail (Nacalai Tesque, Inc.) and 200 mM NaF. The homogenate was then centrifuged at 15000 rpm, 4° C. for 20 minutes to collect the supernatant. The extracted proteins were measured for their concentration using DC protein assay reagents (BIO-RAD). Then, the proteins were mixed into 2× sample buffer (Laemmli Sample Buffer (BIO-RAD), 5% 2-mercaptoethanol) and treated by heating at 98° C. for 5 minutes. The prepared protein sample was electrophoresed at 10 mA for 180 minutes using Multigel II mini 7.5 (Daiichi Pure Chemicals Co., Ltd.) and then transferred overnight onto an Immobilon-P Transfer Membrane (MILLIPORE) at 30 V and 4° C. Then, the membrane was soaked in 5% skimmed milk in PBS-T for 1 hour or in Blocking One-P (Nacalai Tesque, Inc.) for 20 minutes and shaken at room temperature for blocking. Then, a primary antibody (anti-human Exon-17 monoclonal antibody (No. 3) at 1:500 dilution; anti-avian α-tubulin monoclonal IgG antibody (Sigma) at 1:5000 dilution as a control) was added and reacted overnight at 4° C., followed by washing three times in PBS-T for 5 minutes. Then, a secondary antibody (Anti mouse IgG HRP (PROMEGA) at 1:10000 dilution) was added and reacted for 1 hour at room temperature. The membrane was washed in PBS-T once for 10 minutes and then twice for 30 minutes, followed by chemiluminescence band detection using an ECL-Plus (Amersham Biosciences). The results indicated that normal lower limbs showed no periostin expression, whereas the tumor tissue showed enhanced expression (FIG. 17).

Example 23

Figure 18:
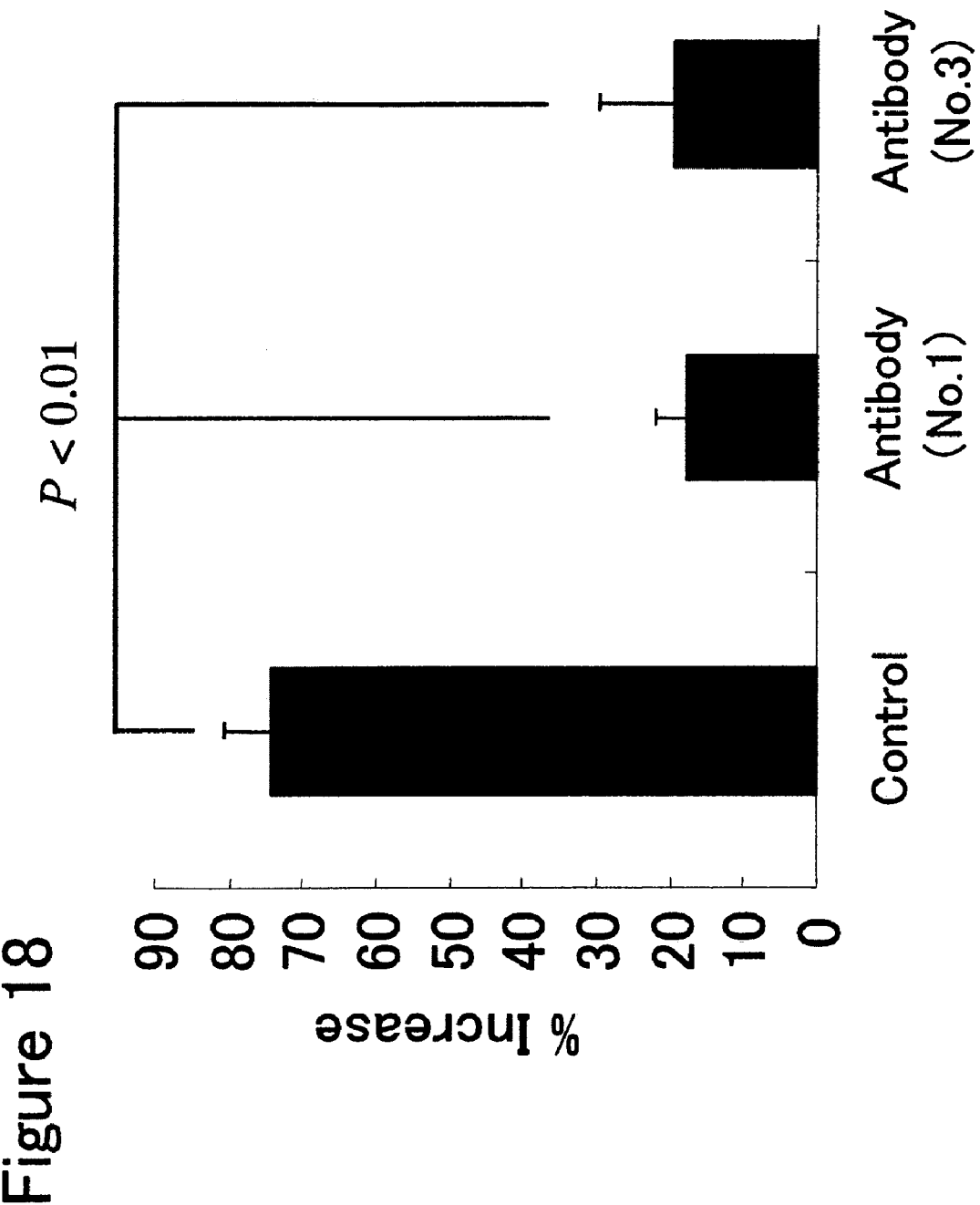
FIG. 18 is a diagram showing assay results of the effect of anti-human Exon-17 monoclonal antibodies (No. 1 and No. 3) by using model mice for lung metastasis of mouse melanoma B16-F10 cells (Example 23).

Effect of Anti-rat Exon-17 Polyclonal Antibody and Anti-human Exon-17 Monoclonal Antibody Using Model Mice for Lung Metastasis of Mouse Melanoma B16-F10 Cells Mouse melanoma B16-F10 cells were cultured in a 37° C. incubator, washed with PBS and then treated with trypsin/EDTA to float and collect the cells. Then, the cells collected by centrifugation at 1500 rpm for 3 minutes were counted to give $5 \times 10^5$ cells/animal and suspended in 100 μl PBS. The adjusted cells were injected into the sole of C57BL/6N male mice (8 weeks of age) using an insulin syringe equipped with a 29G Myjector injection needle (TERMO). First of all, to study the effect of the two monoclonal antibodies (No. 1 and No. 3) obtained in Example 6, these antibodies (2 μg/animal) were each administered to the mice via the jugular vein through an insulin syringe equipped with a 29G Myjector injection needle, simultaneously with the inoculation of the cells. As a control, Normal Rabbit IgG (R&D Systems) was used. At one week after administration of the cells and antibodies, the diameter of swelling lesions in the lower limbs was determined with a caliper to evaluate % increase in primary tumor size. As a result, the % increase in primary tumor size was 74.5±6.3% (n=11) in the control group, 17.8±4.4% (n=10) in the antibody (No. 1) group and 19.5±9.9% (n=10) in the antibody (No. 3) group, indicating that both antibodies have the same inhibitory activity on cancer growth (FIG. 18).

Next, subsequent to the inoculation of mouse melanoma B16-F10 cells, antibody administration was started after a given period of time to study whether the antibody has an effect under conditions much closer to clinical cases. At one week after cell injection for the experiment using anti-rat Exon-17 polyclonal antibody (0.75 mg/ml) and at 3 and 7 days after cell injection for the experiment using anti-human Exon-17 monoclonal antibody (No. 3) (2.14 mg/ml), each antibody (20 μg/animal) was administered to the mice via the jugular vein through an insulin syringe equipped with a 29G Myjector injection needle. As a control, Normal Rabbit IgG (R&D Systems) was used. After cell injection, the diameter of swelling lesions in the lower limbs was determined weekly with a caliper to evaluate % increase in primary tumor size. To avoid overgrowth of primary tumors which causes direct cancer invasion into the subperitoneal space and leads to death of the mice, lower limbs with primary tumors were excised at 2 weeks after cell injection. At 5 weeks after cell injection, autopsy was performed to determine the presence or absence of metastasis from primary tumor to lung and the number of colonies metastasized to lung. The % increase in primary tumor size was expressed as a percentage of increment, assuming that the limb diameter before injection of mouse melanoma B16-F10 cells was set to 100, and data analysis was made by the Student's t-test. Likewise, the metastasis rate from primary tumor to lung was analyzed by the $\chi^2$ test, while the number of colonies metastasized to lung was analyzed by the Mann-Whitney test.

Figure 19:
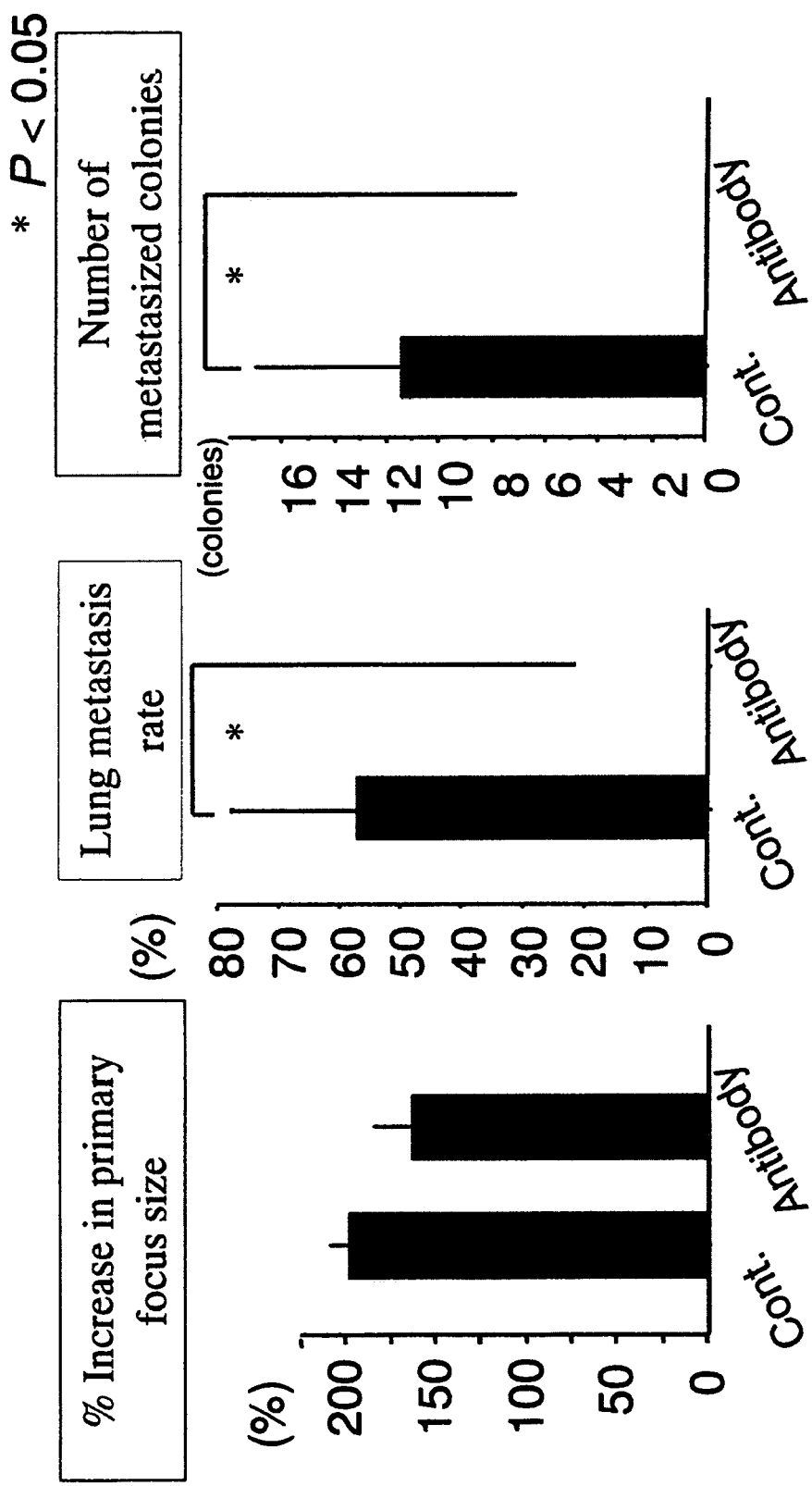
FIG. 19 is a diagram showing assay results of the effect of anti-rat Exon-17 polyclonal antibody by using model mice for lung metastasis of mouse melanoma B16-F10 cells (Example 23: % increase in primary tumor size, lung metastasis rate, number of metastasized colonies).

In the experiment where anti-rat Exon-17 polyclonal antibody was administered, the % increase in primary tumor size at 2 weeks after cell injection (in comparison with the limb diameter before cell injection) was 198.1±10.428% (n=10) in the control group and 163.2±21.015% (n=11) in the neutralizing antibody group (FIG. 19). On the other hand, the metastasis rate from primary tumor to lung was 57.1% (n=7) in the control group and 0% (n=6) in the neutralizing antibody group, indicating that the metastasis was significantly inhibited in the neutralizing antibody group (FIG. 19). The number of colonies metastasized from primary tumor to lung was 1.143±0.553 in the control group (FIG. 19).

Figure 20:
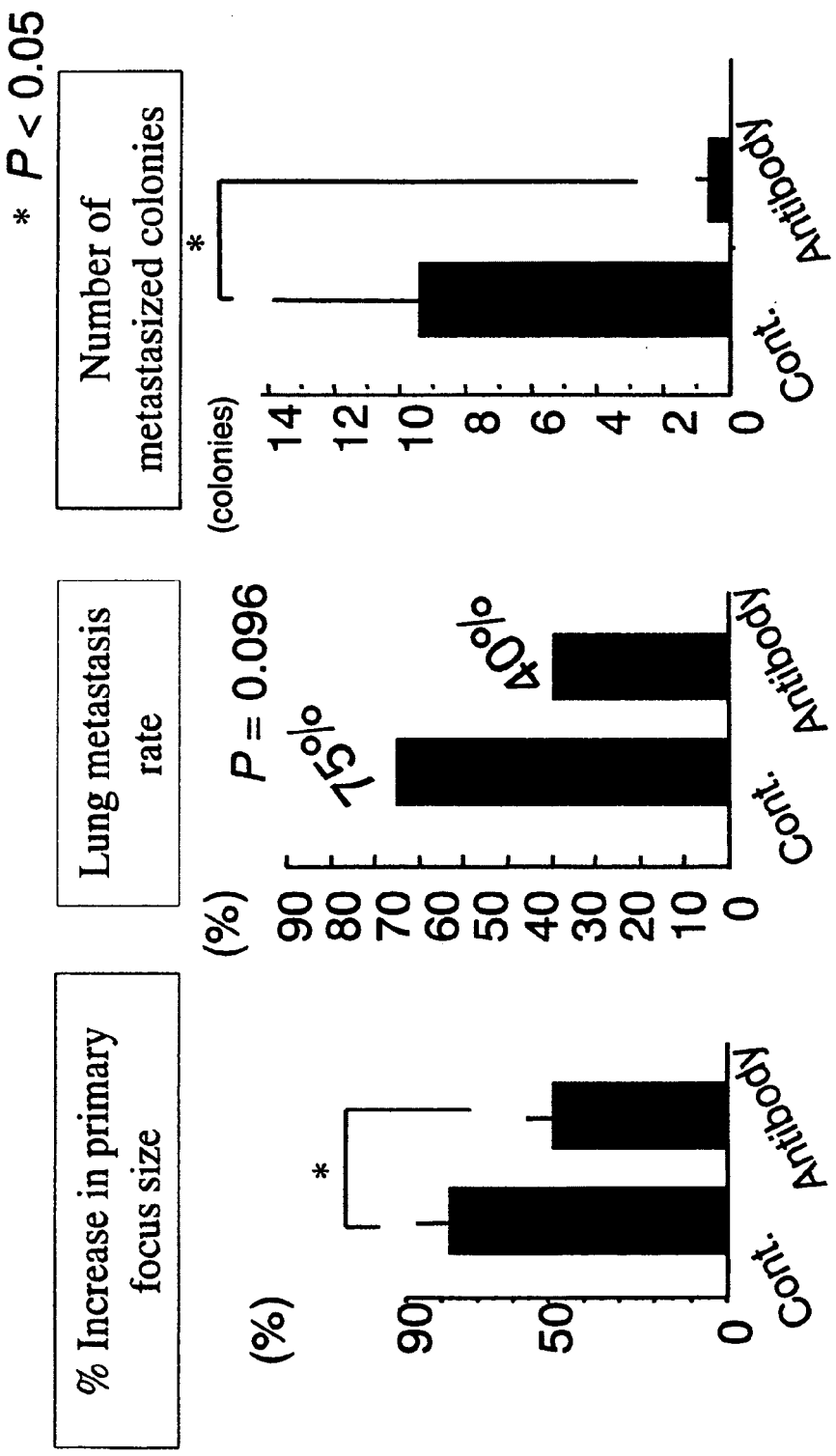
FIG. 20 is a diagram showing assay results of the effect of anti-human Exon-17 monoclonal antibody (No. 3) by using model mice for lung metastasis of mouse melanoma B16-F10 cells (Example 23: % increase in primary tumor size, lung metastasis rate, number of metastasized colonies).

Next, in the experiment where anti-human Exon-17 monoclonal antibody (No. 3) was administered, the % increase in primary tumor size at 1 week after cell injection (in comparison with the limb diameter before cell injection) was 77.6±9.484% (n=12) in the control group and 48.9±7.060% (n=11) in the neutralizing antibody group, indicating that primary tumor growth was significantly inhibited in the neutralizing antibody group (P<0.05) (FIG. 20). Likewise, the metastasis rate from primary tumor to lung was 75% (n=12) in the control group and 40% in the neutralizing antibody group (n=10), indicating that the metastasis rate tended to decrease in the neutralizing antibody group (P=0.0964) (FIG. 20). The number of colonies metastasized from primary tumor to lung was 9.41±4.38 in the control group and 0.7±0.335 in the neutralizing antibody group, indicating that the number of metastasized colonies was significantly inhibited in the neutralizing antibody group (P<0.05) (FIG. 20). These results showed that the anti-rat Exon-17 polyclonal antibody has an inhibitory effect on lung metastasis of melanoma cells. It was further found that the anti-human Exon-17 monoclonal antibody (No. 3) also has an inhibitory effect on primary tumor growth.

Example 24

Figure 21:
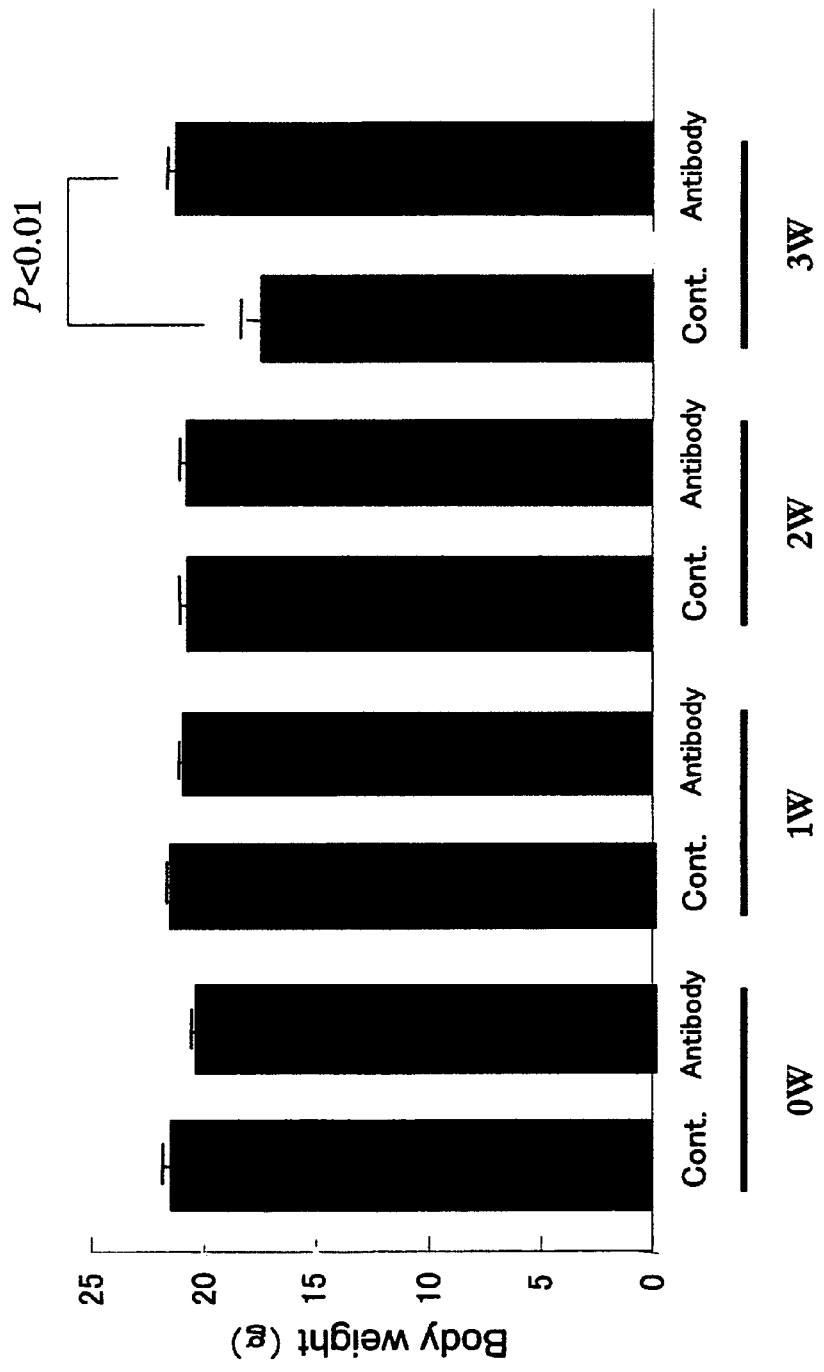
FIG. 21 is a diagram showing assay results of the effect of anti-rat Exon-17 polyclonal antibody by using model mice for lung metastasis of mouse 4T1 breast cancer cells (Example 24: body weight change).
Figure 22:
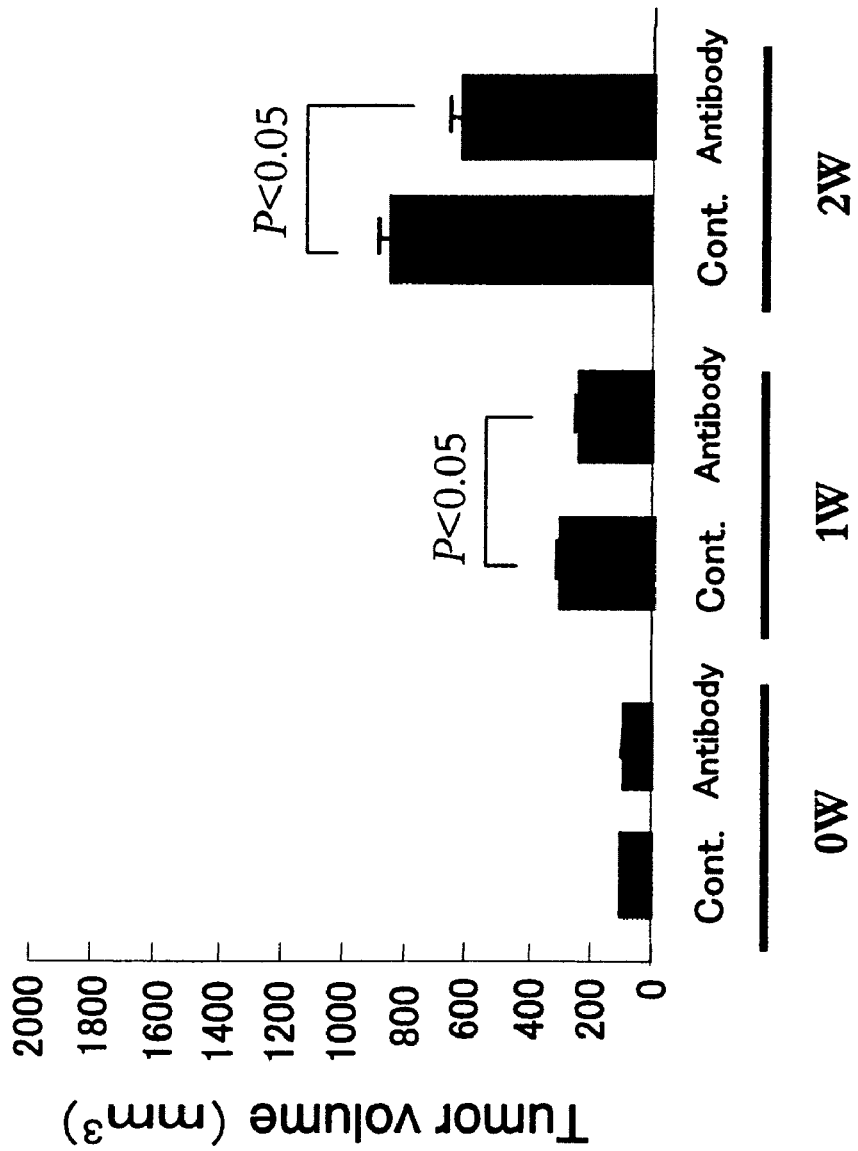
FIG. 22 is a diagram showing assay results of the effect of anti-rat Exon-17 polyclonal antibody by using model mice for lung metastasis of mouse 4T1 breast cancer cells (Example 24: tumor volume change in primary tumor).
Figure 23:
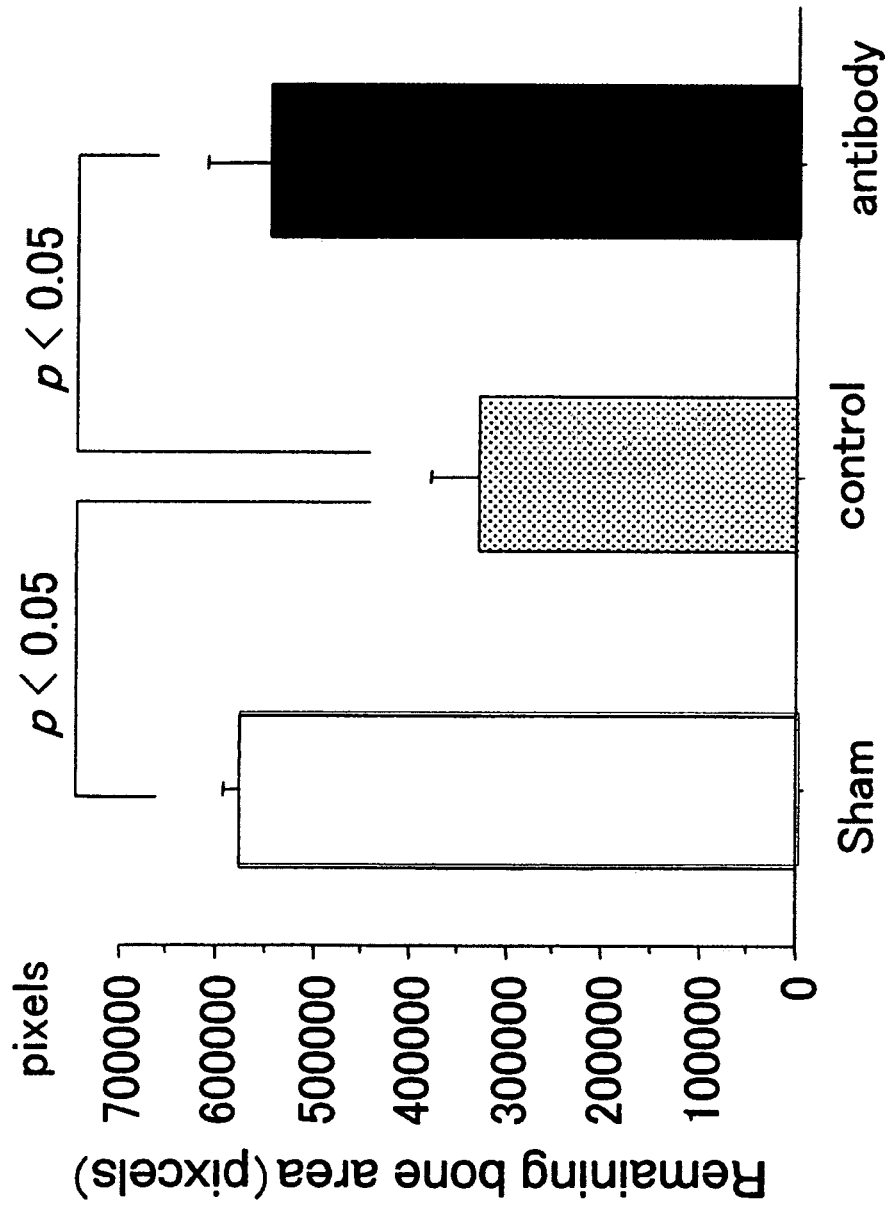
FIG. 23 is a diagram showing assay results of the effect of anti-rat Exon-17 polyclonal antibody by using model mice for lung metastasis of mouse 4T1 breast cancer cells (Example 24: comparison of bone area in bone destruction caused by bone invasion).
Figure 24:
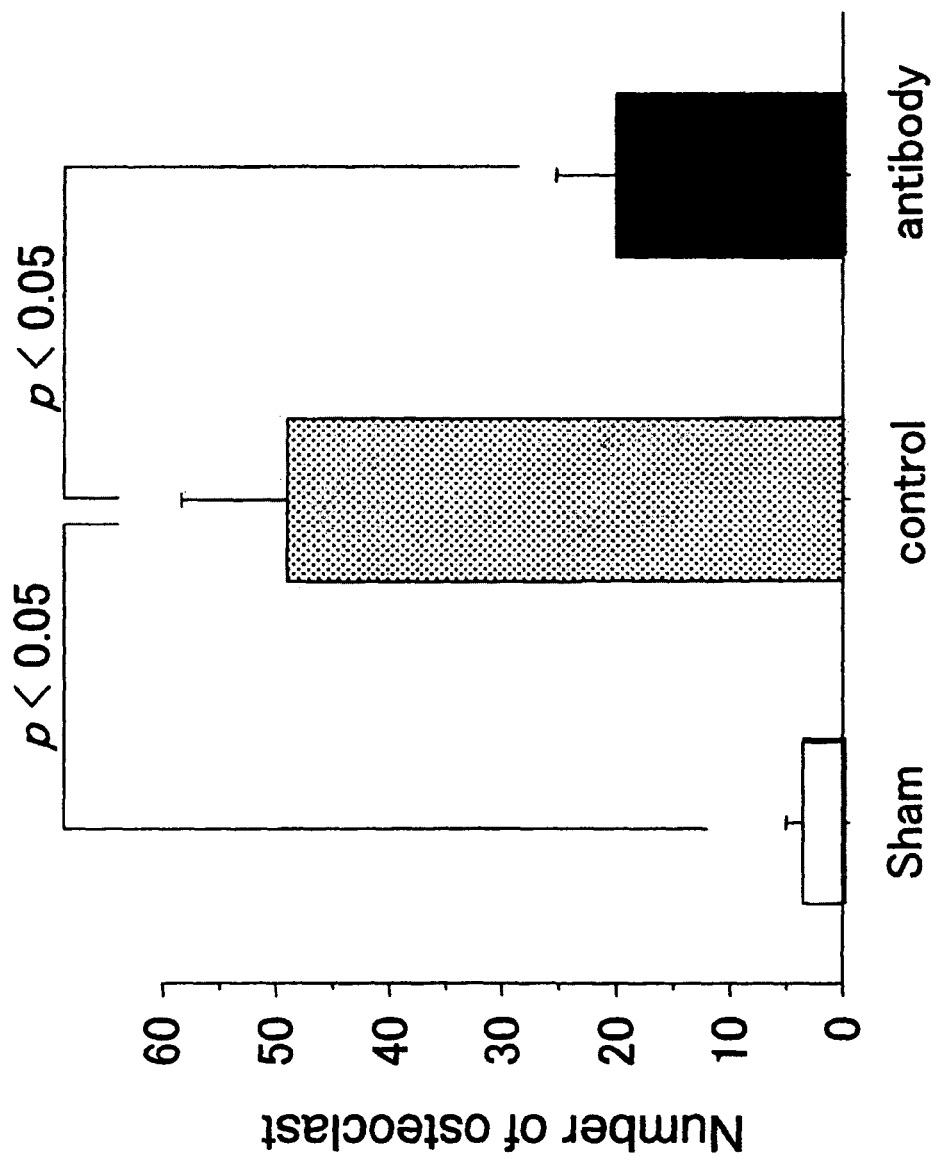
FIG. 24 is a diagram showing assay results of the effect of anti-rat Exon-17 polyclonal antibody by using model mice for lung metastasis of mouse 4T1 breast cancer cells (Example 24: comparison of number of osteoclast in bone destruction caused by bone invasion).
Figure 25:
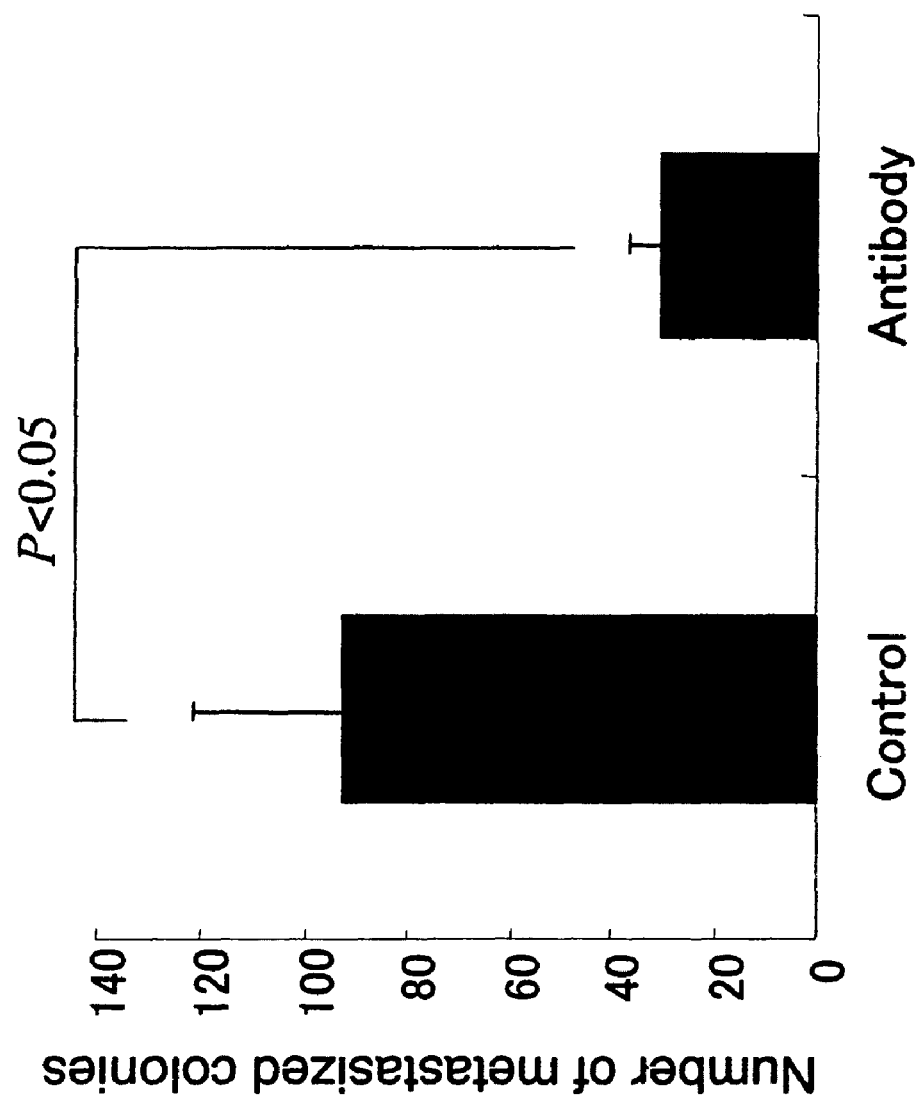
FIG. 25 is a diagram showing assay results of the effect of anti-rat Exon-17 polyclonal antibody by using model mice for lung metastasis of mouse 4T1 breast cancer cells (Example 24: number of metastasized colonies at 3 weeks after inoculation of mouse 4T1 breast cancer cells).

Effect of Anti-rat Exon-17 Polyclonal Antibody Using Model Mice for Lung Metastasis of Mouse 4T1 Breast Cancer Cells Mouse 4T1 cells (ATCC No. CRL-2539) were seeded in 10 cm Tissue Culture Dishes (Greiner) using RPMI1640 (Gibco) containing 10% bovine serum albumin (FBS) (Bio west) and a Penicillin-streptomycin Mixed solution (Nacalai Tesque, Inc.), and then cultured in a 37° C. incubator for 24 hours. After removal of the culture supernatant, the cells were washed with PBS and then allowed to float by treatment with trypsin/EDTA. The cells were collected and centrifuged at 1500 rpm for 3 minutes, $1.5 \times 10^5$ of which were then subcultured in a 37° C. incubator for 72 hours. Cells in the logarithmic growth phase were counted to give $1 \times 10^6$ cells/animal and suspended in 100 μl PBS. The adjusted cells were injected into the sole of BALB/c female mice (8 weeks of age) using an insulin syringe equipped with a 29G Myjector injection needle (TERMO). An antibody (20 μg/animal) was also administered to the mice via the jugular vein through an insulin syringe equipped with a 29G Myjector injection needle. In the experiment using anti-rat Exon-17 polyclonal antibody (1 mg/ml), the antibody was administered simultaneously with cell injection, and further administered at 1 and 2 weeks after cell injection. As a control, Normal Rabbit IgG (R&D Systems) was used. After cell injection, the mice were weekly measured for their body weight and the diameter of swelling lesions in their lower limbs with a caliper to evaluate primary tumor volume. Evaluation was accomplished as described in Dethlefsen L A, et al. J. Natl. Cancer Inst., 40, 389 (1968) to determine the volume according to the following equation: (sole length)×(square of sole width)/2. At 3 weeks after cell injection, autopsy was performed to determine body weight, the presence or absence of metastasis from primary tumor to lung, and the number of colonies metastasized to lung. Data analysis was made by the Student's t-test for each case. As a result, with respect to changes in body weight, there was no significant difference between both groups until 2 weeks after cell injection. After 3 weeks, however, the body weight was 17.50±0703 g (n=6) in the control group and 21.24±0.517 g (n=6) in the neutralizing antibody group, indicating that primary tumor growth was significantly inhibited in the neutralizing antibody group (P<0.05) (FIG. 21). Moreover, the tumor volume of primary tumor at 1 week after cell injection was 301.3±11.49 mm$^3$ (n=10) in the control group and 235.9±7.842 mm$^3$ (n=10) in the neutralizing antibody group, indicating that primary tumor growth was significantly inhibited in the neutralizing antibody group (P<0.05). Likewise, the tumor volume of primary tumor at 2 weeks after cell injection was 842.4±34.71 mm$^3$ (n=10) in the control group and 613.9±45.17 mm$^3$ (n=10) in the neutralizing antibody group, indicating that primary tumor growth was significantly inhibited in the neutralizing antibody group (P<0.05) (FIG. 22). At 3 weeks after cell injection, the control group showed loss of limbs due to necrosis, whereas the neutralizing antibody group showed no loss of limbs. Further, evaluation of bone destruction caused by bone invasion of breast cancer cells from primary tumor was accomplished by measuring bone area and the number of osteoclast after HE staining and TRAP staining was carried out to ancle bone of lower limb. The remaining bone area after direct invasion to bone was 326656±53628.7 (n=5) in the control group and 545756.8±65928.8 (n=5) in the neutralizing antibody group, indication that bone significantly remained in the neutralizing antibody group (P<0.05) (FIG. 23). Moreover, the number of osteoclast was adversely correlated the remaining bone area, and the number of osteoclast was 49±9.576 (n=5) in the control group and 20±5.167 (n=5) in the neutralizing antibody group, indication that the number of osteoclast was significantly low in the neutralizing antibody group (P<0.05) (FIG. 24). With respect to the metastasis rate from primary tumor to lung, both groups showed metastasis, but the number of metastasized colonies was 89±28.9 in the control group and 30.5±6.30 in the neutralizing antibody group, indicating that the number of metastasized colonies was significantly inhibited in the neutralizing antibody group (P<0.05) (FIG. 25). These results showed that the anti-rat Exon-17 polyclonal antibody not only inhibits primary tumor growth of breast cancer cells, but also has an inhibitory effect on lung metastasis of breast cancer cells.

INDUSTRIAL APPLICABILITY

Diseases in which periostin is involved can be prevented and treated by suppression of the function of a periostin isoform having anti-cell adhesive activity highly expressed in a disease such as heart failure, inhibition of the aggravation of condition and improvement of the function of tissue by use of an antibody against the periostin isoform having anti-cell adhesive activity. Moreover, the presence of the diseases and the degree of progress of symptoms can be known by measurement of the amount of the periostin isoform in a sample from a patient. The use of antibodies against a peptide encoded by the Exon-17 region of periostin enables cancer treatment, more specifically the inhibition of primary tumor growth and metastasis. It is also possible to know the presence or absence of cancers and the degree of their progress by measuring the amounts of periostin isoforms in patient samples using the above antibodies.

The invention claimed is:

1. A method for treating heart failure, myocardial infarction, or cancer, comprising administering to a patient an antibody against a periostin isoform having anti-cell adhesive activity, that specifically recognizes the amino acid sequence encoded by Exon-17 or a part thereof, and is capable of neutralizing anti-cell adhesive activity of periostin.

2. The method of claim 1, wherein the disease is cancer.

3. The method of claim 2, wherein the disease is cancer of breast, large intestine, lung, malignant melanoma, bone, pancreas, stomach, skin, uterus, ovary, rectum, colon, esophagus, small intestine, thyroid, adrenal gland, prostrate, bladder or kidney.

4. The method of claim 2, wherein cancer is treated by inhibiting cancer metastasis.

5. The method of claim 2, wherein cancer is treated by inhibiting the growth of primary tumor.

6. The method of claim 2, wherein cancer is treated by inhibiting the bone invasion of cancer or bone destruction caused by bone invasion of cancer.

7. The method of claim 2, wherein the cancer is malignant melanoma or breast cancer.

8. The method of claim 1, wherein the amino acid sequence encoded by Exon-17 or part thereof is the amino acid sequence of SEQ ID NO: 3, 4, 21, 22, 23, 24, 26 or 34.

9. The method of claim 8, wherein the amino acid sequence is the amino acid sequence of SEQ ID NO: 3, 4, or 21.

10. The method of any one of claims 1, 8, or 9, wherein the antibody is a monoclonal antibody.

11. The method of claim 10, further comprising producing the monoclonal antibody using a hydridoma cell line FERM BP-10718.

12. The method of claim 10, further comprising producing the monoclonal antibody by the method comprising:
    immunizing a mammal with a peptide having the amino acid sequence of SEQ ID NO: 3, 4, or 21, or a peptide thereof comprising cysteine residues introduced into the N-terminus thereof;
    fusing an antibody-producing cell of the mammal with a myeloma cell; and
    culturing the obtained hybridoma.

13. The method of claim 3, further comprising treating cancer by inhibiting cancer metastasis.

14. The method of claim 3, further comprising treating cancer by inhibiting the growth of primary tumor.

15. The method of claim 3, further comprising treating cancer by inhibiting the bone invasion of cancer or bone destruction caused by bone invasion of cancer.

16. The method of claim 3, wherein the cancer is malignant melanoma or breast cancer.

17. The method of claim 4, wherein the cancer is malignant melanoma or breast cancer.

18. The method of claim 5, wherein the cancer is malignant melanoma or breast cancer.

19. The method of claim 6, wherein the cancer is malignant melanoma or breast cancer.

20. The method of claim 1, wherein the disease is heart failure.

21. The method of claim 1, wherein the disease is myocardial infarction.

22. The method of claim 1, wherein the disease is lung metastasis of breast cancer.

23. A method for neutralizing anti-cell adhesive activity of periostin comprising binding an antibody that specifically recognizes the amino acid sequence encoded by Exon-17 or a part thereof, and is capable of neutralizing anti-cell adhesive activity of periostin.

24. The method of claim 23, wherein the amino acid sequence encoded by Exon-17 or a part thereof is produced in a cancer cell.

* * * * *

SEQUENCE LISTING

```
<160> NUMBER OF SEQ ID NOS: 80

<210> SEQ ID NO 1
<211> LENGTH: 838
<212> TYPE: PRT
<213> ORGANISM: Rattus sp.

<400> SEQUENCE: 1

Met Val Pro Leu Leu Pro Leu Ser Ala Leu Leu Leu Leu Phe Leu Cys
1               5                   10                  15

Asp Val Asp Pro Ala Asn Ala Asn Ser Tyr Tyr Asp Lys Val Leu Ala
            20                  25                  30

His Ser Arg Ile Arg Gly Arg Asp Gln Gly Pro Asn Val Cys Ala Leu
        35                  40                  45

Gln Gln Ile Leu Gly Thr Lys Lys Tyr Phe Ser Ser Cys Lys Asn
    50                  55                  60

Trp Tyr Gln Gly Ala Ile Cys Gly Lys Lys Thr Thr Val Leu Tyr Glu
65                  70                  75                  80

Cys Cys Pro Gly Tyr Met Arg Met Glu Gly Met Lys Gly Cys Pro Ala
                85                  90                  95

Val Met Pro Ile Asp His Val Tyr Gly Thr Leu Gly Ile Val Gly Ala
            100                 105                 110
```

-continued

```
Thr Thr Thr Gln His Tyr Ser Asp Val Ser Lys Leu Arg Glu Ile
        115                 120                 125
Glu Gly Lys Gly Ser Tyr Thr Tyr Phe Ala Pro Ser Asn Glu Ala Trp
130                 135                 140
Asp Asn Leu Asp Ser Asp Ile Arg Arg Gly Leu Glu Asn Asn Val Asn
145                 150                 155                 160
Val Glu Leu Leu Asn Ala Leu His Ser His Met Val Asn Lys Arg Met
                165                 170                 175
Leu Thr Lys Asp Leu Lys His Gly Met Val Ile Pro Ser Met Tyr Asn
                180                 185                 190
Asn Leu Gly Leu Phe Ile Asn His Tyr Pro Asn Gly Val Val Thr Val
            195                 200                 205
Asn Cys Ala Arg Val Ile His Gly Asn Gln Ile Ala Thr Asn Gly Val
        210                 215                 220
Val His Val Ile Asp Arg Val Leu Thr Gln Ile Gly Thr Ser Ile Gln
225                 230                 235                 240
Asp Phe Ile Glu Ala Glu Asp Glu Leu Ser Ser Phe Arg Ala Ala Ala
                245                 250                 255
Ile Thr Ser Asp Leu Leu Glu Ser Leu Gly Arg Asp Gly His Phe Thr
                260                 265                 270
Leu Phe Ala Pro Thr Asn Glu Ala Phe Glu Lys Leu Pro Arg Gly Val
            275                 280                 285
Leu Glu Arg Ile Met Gly Asp Lys Val Ala Ser Glu Ala Leu Met Lys
        290                 295                 300
Tyr His Ile Leu Asn Thr Leu Gln Cys Ser Glu Ala Ile Thr Gly Gly
305                 310                 315                 320
Ala Val Phe Glu Thr Met Glu Gly Asn Thr Ile Glu Ile Gly Cys Glu
                325                 330                 335
Gly Asp Ser Ile Ser Ile Asn Gly Ile Lys Met Val Asn Lys Lys Asp
            340                 345                 350
Ile Val Thr Lys Asn Gly Val Ile His Leu Ile Asp Glu Val Leu Ile
        355                 360                 365
Pro Asp Ser Ala Lys Gln Val Ile Glu Leu Ala Gly Lys Gln Gln Thr
    370                 375                 380
Thr Phe Thr Asp Leu Val Ala Gln Leu Gly Leu Ala Ser Ser Leu Lys
385                 390                 395                 400
Pro Asp Gly Glu Tyr Thr Leu Leu Ala Pro Val Asn Asn Ala Phe Ser
                405                 410                 415
Asp Asp Thr Leu Ser Met Asp Gln Arg Leu Leu Lys Leu Ile Leu Gln
            420                 425                 430
Asn His Ile Leu Lys Val Lys Val Gly Leu Ser Asp Leu Tyr Asn Gly
        435                 440                 445
Gln Ile Leu Glu Thr Ile Gly Gly Lys Gln Leu Arg Val Phe Val Tyr
    450                 455                 460
Arg Thr Ala Ile Cys Ile Glu Asn Ser Cys Met Val Arg Gly Ser Lys
465                 470                 475                 480
Gln Gly Arg Asn Gly Ala Ile His Ile Phe Arg Glu Ile Ile Gln Pro
                485                 490                 495
Ala Glu Lys Ser Leu His Glu Lys Leu Arg Gln Asp Lys Arg Phe Ser
            500                 505                 510
Ile Phe Leu Ser Leu Leu Glu Ala Ala Asp Leu Lys Asp Leu Leu Thr
        515                 520                 525
Gln Pro Gly Asp Trp Thr Leu Phe Ala Pro Thr Asn Asp Ala Phe Lys
```

```
                530                 535                 540
Gly Met Thr Asn Glu Glu Arg Glu Ile Leu Ile Gly Asp Lys Asn Ala
545                 550                 555                 560

Leu Gln Asn Ile Ile Leu Tyr His Leu Thr Pro Gly Val Tyr Ile Gly
                565                 570                 575

Lys Gly Phe Glu Pro Gly Val Thr Asn Ile Leu Lys Thr Thr Gln Gly
            580                 585                 590

Ser Lys Ile Tyr Val Lys Gly Val Asn Glu Thr Leu Leu Val Asn Glu
            595                 600                 605

Leu Lys Ser Lys Glu Ser Asp Ile Met Thr Thr Asn Gly Val Ile His
        610                 615                 620

Val Val Asp Lys Leu Leu Tyr Pro Ala Asp Ile Pro Val Gly Asn Asp
625                 630                 635                 640

Gln Leu Leu Glu Leu Leu Asn Lys Leu Ile Lys Tyr Ile Gln Ile Lys
                645                 650                 655

Phe Val Arg Gly Ser Thr Phe Lys Glu Ile Pro Met Thr Val Tyr Thr
            660                 665                 670

Thr Lys Ile Ile Thr Lys Leu Val Glu Pro Lys Ile Lys Val Ile Gln
            675                 680                 685

Gly Ser Leu Gln Pro Ile Ile Lys Thr Glu Gly Pro Ala Met Thr Lys
        690                 695                 700

Ile His Ile Glu Gly Glu Pro Asp Phe Arg Leu Ile Lys Glu Gly Glu
705                 710                 715                 720

Thr Val Thr Glu Val Ile His Gly Glu Pro Val Ile Lys Lys Tyr Thr
                725                 730                 735

Lys Ile Ile Asp Gly Val Pro Val Glu Ile Thr Glu Lys Glu Thr Arg
            740                 745                 750

Glu Glu Arg Ile Ile Thr Gly Pro Glu Ile Lys Tyr Thr Arg Ile Ser
        755                 760                 765

Thr Gly Gly Gly Glu Thr Glu Glu Thr Leu Gln Lys Phe Leu Gln Lys
        770                 775                 780

Glu Val Ser Lys Val Thr Lys Phe Ile Glu Gly Gly Asp Gly His Leu
785                 790                 795                 800

Phe Glu Asp Glu Ala Ile Lys Arg Leu Leu Gln Gly Asp Thr Pro Ala
                805                 810                 815

Lys Lys Ile Gln Ala Asn Lys Arg Val Gln Gly Ser Arg Arg Arg Ser
            820                 825                 830

Arg Glu Gly Arg Ser Gln
            835

<210> SEQ ID NO 2
<211> LENGTH: 836
<212> TYPE: PRT
<213> ORGANISM: Homo sapiens

<400> SEQUENCE: 2

Met Ile Pro Phe Leu Pro Met Phe Ser Leu Leu Leu Leu Leu Ile Val
1               5                   10                  15

Asn Pro Ile Asn Ala Asn Asn His Tyr Asp Lys Ile Leu Ala His Ser
                20                  25                  30

Arg Ile Arg Gly Arg Asp Gln Gly Pro Asn Val Cys Ala Leu Gln Gln
            35                  40                  45

Ile Leu Gly Thr Lys Lys Lys Tyr Phe Ser Thr Cys Lys Asn Trp Tyr
        50                  55                  60

Lys Lys Ser Ile Cys Gly Gln Lys Thr Thr Val Leu Tyr Glu Cys Cys
```

-continued

```
                65                  70                  75                  80
        Pro Gly Tyr Met Arg Met Glu Gly Met Lys Gly Cys Pro Ala Val Leu
                        85                  90                  95

Pro Ile Asp His Val Tyr Gly Thr Leu Gly Ile Val Gly Ala Thr Thr
                        100                 105                 110

Thr Gln Arg Tyr Ser Asp Ala Ser Lys Leu Arg Glu Ile Glu Gly
                        115                 120                 125

Lys Gly Ser Phe Thr Tyr Phe Ala Pro Ser Asn Glu Ala Trp Asp Asn
                        130                 135                 140

Leu Asp Ser Asp Ile Arg Arg Gly Leu Glu Ser Asn Val Asn Val Glu
        145                 150                 155                 160

Leu Leu Asn Ala Leu His Ser His Met Ile Asn Lys Arg Met Leu Thr
                        165                 170                 175

Lys Asp Leu Lys Asn Gly Met Ile Ile Pro Ser Met Tyr Asn Asn Leu
                        180                 185                 190

Gly Leu Phe Ile Asn His Tyr Pro Asn Gly Val Val Thr Val Asn Cys
                        195                 200                 205

Ala Arg Ile Ile His Gly Asn Gln Ile Ala Thr Asn Gly Val Val His
                        210                 215                 220

Val Ile Asp Arg Val Leu Thr Gln Ile Gly Thr Ser Ile Gln Asp Phe
        225                 230                 235                 240

Ile Glu Ala Glu Asp Asp Leu Ser Ser Phe Arg Ala Ala Ile Thr
                        245                 250                 255

Ser Asp Ile Leu Glu Ala Leu Gly Arg Asp Gly His Phe Thr Leu Phe
                        260                 265                 270

Ala Pro Thr Asn Glu Ala Phe Glu Lys Leu Pro Arg Gly Val Leu Glu
                        275                 280                 285

Arg Phe Met Gly Asp Lys Val Ala Ser Glu Ala Leu Met Lys Tyr His
                        290                 295                 300

Ile Leu Asn Thr Leu Gln Cys Ser Glu Ser Ile Met Gly Gly Ala Val
        305                 310                 315                 320

Phe Glu Thr Leu Glu Gly Asn Thr Ile Glu Ile Gly Cys Asp Gly Asp
                        325                 330                 335

Ser Ile Thr Val Asn Gly Ile Lys Met Val Asn Lys Asp Ile Val
                        340                 345                 350

Thr Asn Asn Gly Val Ile His Leu Ile Asp Gln Val Leu Ile Pro Asp
                        355                 360                 365

Ser Ala Lys Gln Val Ile Glu Leu Ala Gly Lys Gln Gln Thr Thr Phe
                        370                 375                 380

Thr Asp Leu Val Ala Gln Leu Gly Leu Ala Ser Ala Leu Arg Pro Asp
        385                 390                 395                 400

Gly Glu Tyr Thr Leu Leu Ala Pro Val Asn Asn Ala Phe Ser Asp Asp
                        405                 410                 415

Thr Leu Ser Met Val Gln Arg Leu Leu Lys Leu Ile Leu Gln Asn His
                        420                 425                 430

Ile Leu Lys Val Lys Val Gly Leu Asn Glu Leu Tyr Asn Gly Gln Ile
                        435                 440                 445

Leu Glu Thr Ile Gly Gly Lys Gln Leu Arg Val Phe Val Tyr Arg Thr
        450                 455                 460

Ala Val Cys Ile Glu Asn Ser Cys Met Glu Lys Gly Ser Lys Gln Gly
        465                 470                 475                 480

Arg Asn Gly Ala Ile His Ile Phe Arg Glu Ile Ile Lys Pro Ala Glu
                        485                 490                 495
```

```
Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
        515                 520                 525

Gly Asp Trp Thr Leu Phe Val Pro Thr Asn Asp Ala Phe Lys Gly Met
    530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
    610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Thr Thr Lys
            660                 665                 670

Ile Ile Thr Lys Val Val Glu Pro Lys Ile Lys Val Ile Glu Gly Ser
        675                 680                 685

Leu Gln Pro Ile Ile Lys Thr Glu Gly Pro Thr Leu Thr Lys Val Lys
    690                 695                 700

Ile Glu Gly Glu Pro Glu Phe Arg Leu Ile Lys Glu Gly Glu Thr Ile
705                 710                 715                 720

Thr Glu Val Ile His Gly Glu Pro Ile Ile Lys Lys Tyr Thr Lys Ile
                725                 730                 735

Ile Asp Gly Val Pro Val Glu Ile Thr Glu Lys Glu Thr Arg Glu Glu
            740                 745                 750

Arg Ile Ile Thr Gly Pro Glu Ile Lys Tyr Thr Arg Ile Ser Thr Gly
        755                 760                 765

Gly Gly Glu Thr Glu Glu Thr Leu Lys Lys Leu Leu Gln Glu Glu Val
    770                 775                 780

Thr Lys Val Thr Lys Phe Ile Glu Gly Gly Asp Gly His Leu Phe Glu
785                 790                 795                 800

Asp Glu Glu Ile Lys Arg Leu Leu Gln Gly Asp Thr Pro Val Arg Lys
                805                 810                 815

Leu Gln Ala Asn Lys Lys Val Gly Ser Arg Arg Leu Arg Glu
        820                 825                 830

Gly Arg Ser Gln
        835

<210> SEQ ID NO 3
<211> LENGTH: 27
<212> TYPE: PRT
<213> ORGANISM: Rattus sp.

<400> SEQUENCE: 3

Thr Thr Lys Ile Ile Thr Lys Leu Val Glu Pro Lys Ile Lys Val Ile
1               5                   10                  15

Gln Gly Ser Leu Gln Pro Ile Ile Lys Thr Glu
            20                  25
```

<210> SEQ ID NO 4
<211> LENGTH: 27
<212> TYPE: PRT
<213> ORGANISM: Homo sapiens

<400> SEQUENCE: 4

Thr Thr Lys Ile Ile Thr Lys Val Val Glu Pro Lys Ile Lys Val Ile
1               5                   10                  15

Glu Gly Ser Leu Gln Pro Ile Ile Lys Thr Glu
            20                  25

<210> SEQ ID NO 5
<211> LENGTH: 811
<212> TYPE: PRT
<213> ORGANISM: Rattus sp.

<400> SEQUENCE: 5

Met Val Pro Leu Leu Pro Leu Ser Ala Leu Leu Leu Phe Leu Cys
1               5                   10                  15

Asp Val Asp Pro Ala Asn Ala Asn Ser Tyr Tyr Asp Lys Val Leu Ala
            20                  25                  30

His Ser Arg Ile Arg Gly Arg Asp Gln Gly Pro Asn Val Cys Ala Leu
        35                  40                  45

Gln Gln Ile Leu Gly Thr Lys Lys Lys Tyr Phe Ser Ser Cys Lys Asn
    50                  55                  60

Trp Tyr Gln Gly Ala Ile Cys Gly Lys Lys Thr Thr Val Leu Tyr Glu
65                  70                  75                  80

Cys Cys Pro Gly Tyr Met Arg Met Glu Gly Met Lys Gly Cys Pro Ala
                85                  90                  95

Val Met Pro Ile Asp His Val Tyr Gly Thr Leu Gly Ile Val Gly Ala
            100                 105                 110

Thr Thr Thr Gln His Tyr Ser Asp Val Ser Lys Leu Arg Glu Glu Ile
        115                 120                 125

Glu Gly Lys Gly Ser Tyr Thr Tyr Phe Ala Pro Ser Asn Glu Ala Trp
    130                 135                 140

Asp Asn Leu Asp Ser Asp Ile Arg Arg Gly Leu Glu Asn Asn Val Asn
145                 150                 155                 160

Val Glu Leu Leu Asn Ala Leu His Ser His Met Val Asn Lys Arg Met
                165                 170                 175

Leu Thr Lys Asp Leu Lys His Gly Met Val Ile Pro Ser Met Tyr Asn
            180                 185                 190

Asn Leu Gly Leu Phe Ile Asn His Tyr Pro Asn Gly Val Val Thr Val
        195                 200                 205

Asn Cys Ala Arg Val Ile His Gly Asn Gln Ile Ala Thr Asn Gly Val
    210                 215                 220

Val His Val Ile Asp Arg Val Leu Thr Gln Ile Gly Thr Ser Ile Gln
225                 230                 235                 240

Asp Phe Ile Glu Ala Glu Asp Leu Ser Ser Phe Arg Ala Ala
                245                 250                 255

Ile Thr Ser Asp Leu Leu Glu Ser Leu Gly Arg Asp Gly His Phe Thr
            260                 265                 270

Leu Phe Ala Pro Thr Asn Glu Ala Phe Glu Lys Leu Pro Arg Gly Val
        275                 280                 285

Leu Glu Arg Ile Met Gly Asp Lys Val Ala Ser Glu Ala Leu Met Lys
    290                 295                 300

Tyr His Ile Leu Asn Thr Leu Gln Cys Ser Glu Ala Ile Thr Gly Gly

```
                305                 310                 315                 320
            Ala Val Phe Glu Thr Met Glu Gly Asn Thr Ile Glu Ile Gly Cys Glu
                            325                 330                 335

Gly Asp Ser Ile Ser Ile Asn Gly Ile Lys Met Val Asn Lys Lys Asp
                            340                 345                 350

Ile Val Thr Lys Asn Gly Val Ile His Leu Ile Asp Glu Val Leu Ile
                            355                 360                 365

Pro Asp Ser Ala Lys Gln Val Ile Glu Leu Ala Gly Lys Gln Gln Thr
                            370                 375                 380

Thr Phe Thr Asp Leu Val Ala Gln Leu Gly Leu Ala Ser Ser Leu Lys
            385                 390                 395                 400

Pro Asp Gly Glu Tyr Thr Leu Leu Ala Pro Val Asn Asn Ala Phe Ser
                            405                 410                 415

Asp Asp Thr Leu Ser Met Asp Gln Arg Leu Leu Lys Leu Ile Leu Gln
                            420                 425                 430

Asn His Ile Leu Lys Val Lys Val Gly Leu Ser Asp Leu Tyr Asn Gly
                            435                 440                 445

Gln Ile Leu Glu Thr Ile Gly Gly Lys Gln Leu Arg Val Phe Val Tyr
                            450                 455                 460

Arg Thr Ala Ile Cys Ile Glu Asn Ser Cys Met Val Arg Gly Ser Lys
            465                 470                 475                 480

Gln Gly Arg Asn Gly Ala Ile His Ile Phe Arg Glu Ile Ile Gln Pro
                            485                 490                 495

Ala Glu Lys Ser Leu His Glu Lys Leu Arg Gln Asp Lys Arg Phe Ser
                            500                 505                 510

Ile Phe Leu Ser Leu Leu Glu Ala Ala Asp Leu Lys Asp Leu Leu Thr
                            515                 520                 525

Gln Pro Gly Asp Trp Thr Leu Phe Ala Pro Thr Asn Asp Ala Phe Lys
                            530                 535                 540

Gly Met Thr Asn Glu Glu Arg Glu Ile Leu Ile Gly Asp Lys Asn Ala
            545                 550                 555                 560

Leu Gln Asn Ile Ile Leu Tyr His Leu Thr Pro Gly Val Tyr Ile Gly
                            565                 570                 575

Lys Gly Phe Glu Pro Gly Val Thr Asn Ile Leu Lys Thr Thr Gln Gly
                            580                 585                 590

Ser Lys Ile Tyr Val Lys Gly Val Asn Glu Thr Leu Leu Val Asn Glu
                            595                 600                 605

Leu Lys Ser Lys Glu Ser Asp Ile Met Thr Thr Asn Gly Val Ile His
                            610                 615                 620

Val Val Asp Lys Leu Leu Tyr Pro Ala Asp Ile Pro Val Gly Asn Asp
            625                 630                 635                 640

Gln Leu Leu Glu Leu Leu Asn Lys Leu Ile Lys Tyr Ile Gln Ile Lys
                            645                 650                 655

Phe Val Arg Gly Ser Thr Phe Lys Glu Ile Pro Met Thr Val Tyr Arg
                            660                 665                 670

Pro Ala Met Thr Lys Ile His Ile Glu Gly Glu Pro Asp Phe Arg Leu
                            675                 680                 685

Ile Lys Glu Gly Glu Thr Val Thr Glu Val Ile His Gly Glu Pro Val
                            690                 695                 700

Ile Lys Lys Tyr Thr Lys Ile Ile Asp Gly Val Pro Val Glu Ile Thr
            705                 710                 715                 720

Glu Lys Glu Thr Arg Glu Glu Arg Ile Ile Thr Gly Pro Glu Ile Lys
                            725                 730                 735
```

```
Tyr Thr Arg Ile Ser Thr Gly Gly Glu Thr Glu Glu Thr Leu Gln
                740                 745                 750

Lys Phe Leu Gln Lys Glu Val Ser Lys Val Thr Lys Phe Ile Glu Gly
            755                 760                 765

Gly Asp Gly His Leu Phe Glu Asp Glu Ala Ile Lys Arg Leu Leu Gln
            770                 775                 780

Gly Asp Thr Pro Ala Lys Lys Ile Gln Ala Asn Lys Arg Val Gln Gly
785                 790                 795                 800

Ser Arg Arg Arg Ser Arg Glu Gly Arg Ser Gln
                805                 810

<210> SEQ ID NO 6
<211> LENGTH: 2517
<212> TYPE: DNA
<213> ORGANISM: Rattus sp.

<400> SEQUENCE: 6
```

| | | | | |
|---|---|---|---|---|
| atggttcctc | tcctgccctt | atctgctctg | ctgctgctgt | tcctgtgtga cgttgacccc | 60 |
| gcaaatgcca | acagttacta | tgacaaggtc | ctagctcaca | gccgcatcag gggtcgggat | 120 |
| cagggcccaa | atgtctgtgc | cctccagcag | attctgggcc | caaaaagaa atacttcagc | 180 |
| tcctgtaaga | actggtatca | aggtgctatc | tgcgggaaga | aaaccactgt gctatatgaa | 240 |
| tgctgccccg | ctatatgag | aatggaaggg | atgaaaggct | gcccagcagt gatgcccatt | 300 |
| gaccatgttt | atggcacgct | gggcatcgtg | ggagccacga | ccactcaaca ctattctgat | 360 |
| gtctcgaagc | tcagggaaga | gattgaagga | aagggtcct | acacatactt cgcgccgagt | 420 |
| aacgaagctt | gggacaacct | ggattccgac | atccgcagag | actagagaa caatgtcaat | 480 |
| gttgagttac | tgaacgcttt | acacagccac | atggttaata | gagaatgct aaccaaggac | 540 |
| ctgaaacacg | gcatggttat | tccttcaatg | tacaacaatc | tggggctttt tatcaatcat | 600 |
| tatcccaatg | gggttgtcac | tgtgaactgt | gctcgagtaa | tccacgggaa ccagattgcc | 660 |
| acaaatggtg | ttgtccatgt | catcgaccgt | gtcctgacac | aaattggcac ctccatccaa | 720 |
| gacttcattg | aagcagaaga | tgagctttca | tcattcagag | cggctgccat cacttctgac | 780 |
| cttttggagt | cccttggaag | agacggtcac | ttcacactct | tgctcccac caatgaggct | 840 |
| ttcgagaaac | tcccacgagg | agtcctagaa | aggatcatgg | agacaaagt ggcttctgaa | 900 |
| gctctcatga | agtaccacat | cctgaatacc | ctccagtgct | ctgaggctat acaggagga | 960 |
| gcggtgtttg | agaccatgga | aggaaacact | attgaaatag | ggtgtgaggg agacagcatc | 1020 |
| tccattaacg | gaatcaagat | ggtgaacaag | aaagacattg | tgacgaagaa tggtgtcatc | 1080 |
| cacctgattg | atgaagtcct | cattcctgat | tctgctaaac | aagttattga gctggctgga | 1140 |
| aaacagcaaa | ccactttcac | ggacctggta | gcccagttag | ggttggcgtc ttctctgaag | 1200 |
| ccggatggag | agtacacgct | gttagcgcct | gtgaacaatg | cgttctctga tgacactctg | 1260 |
| agcatggacc | agcgccttct | taagctaatt | ctgcaaaatc | acatattgaa agtaaaagtc | 1320 |
| ggccttagtg | atctctacaa | tggacagatt | ctggagacca | ttggaggcaa acaactccgt | 1380 |
| gtcttcgtgt | atcggacggc | tatctgcata | gaaaactcat | gcatggtgag aggaagcaag | 1440 |
| caggggagga | acgtgccat | tcacatattc | cgagagatca | tccaaccggc ggagaagtcc | 1500 |
| ctgcacgaaa | aactgcgcca | agataagcgc | ttcagcatct | tcctcagcct cctcgaagct | 1560 |
| gcagatctga | agatcttct | gacacagccc | ggagattgga | ccttgtttgc accaaccaat | 1620 |
| gatgccttca | aggaatgac | taatgaagaa | gggagattc | tgattgggga taaaaatgct | 1680 |
| ctccaaaaca | tcattcttta | ccacctgacc | ccaggggttt | atattggaaa gggatttgaa | 1740 |

```
cccggagtca ccaacatcct gaagaccaca cagggaagca aaatctatgt gaaaggagtc    1800
aatgagacgc ttttggtgaa tgagttgaag tccaaagaat ctgacatcat gacaacaaac    1860
ggcgtcattc acgttgtgga caaactcctc tatccagcag acattccggt tggaaatgat    1920
cagctcttgg aattactgaa caaactgata aaatacatcc aaattaagtt cgttcgtggc    1980
agcaccttca agaaatccc catgactgtc tatacaacta aaattataac caaactcgtg      2040
gaaccaaaaa ttaaagtcat tcaaggcagt cttcagccta ttatcaaaac agaaggacct    2100
gcaatgacga agatccacat tgaaggcgag cctgacttca ggctgattaa agaaggtgaa    2160
acagtgacag aagtgatcca cggagaacca gtcattaaaa agtacaccaa aatcatagac    2220
ggggttcctg ttgaaataac tgaaaaagag acccgggaag aacgcatcat cacaggtcct    2280
gagataaaat acactaggat ttccacagga ggtgggaaaa cagaagagac cctgcagaaa    2340
ttcttgcaaa aagaggtctc caaggtcaca aagttcattg aaggtggcga tggtcactta    2400
tttgaagatg aggcgattaa aagactgctt cagggagaca cacctgcaaa aagatacaa     2460 gccaacaaaa gggttcaagg gtctagaagg cgatcaagag aaggccgttc tcagtga       2517

<210> SEQ ID NO 7
<211> LENGTH: 2436
<212> TYPE: DNA
<213> ORGANISM: Rattus sp.

<400> SEQUENCE: 7
atggttcctc tcctgcccttt atctgctctg ctgctgctgt tcctgtgtga cgttgaccccc    60 gcaaatgcca acagttacta tgacaaggtc ctagctcaca gccgcatcag ggtcgggat     120 cagggcccaa atgtctgtgc cctccagcag attctgggca caaaaagaa atacttcagc      180 tcctgtaaga actggtatca aggtgctatc tgcgggaaga aaaccactgt gctatatgaa     240
tgctgccccg gctatatgag aatgaaaggg atgaaaggct gcccagcagt gatgcccatt    300
gaccatgttt atggcacgct gggcatcgtg ggagccacga ccactcaaca ctattctgat    360
gtctcgaagc tcagggaaga gattgaagga aaagggtcct acacatactt cgcgccgagt    420
aacgaagctt gggacaacct ggattccgac atccgcagag gactagagaa caatgtcaat    480
gttgagttac tgaacgcttt acacagccac atggttaata gagaatgct aaccaaggac    540 ctgaaacacg gcatggttat tccttcaatg tacaacaatc tggggctttt tatcaatcat     600
tatcccaatg gggttgtcac tgtgaactgt gctcgagtaa tccacgggaa ccagattgcc    660
acaaatggtg ttgtccatgt catcgaccgt gtcctgacac aaattggcac ctccatccaa    720
gacttcattg aagcagaaga tgagctttca tcattcagag cggctgccat cacttctgac    780
cttttggagt cccttggaag agacggtcac ttcacactct ttgctcccac caatgaggct    840
ttcgagaaac tcccacgagg agtcctagaa aggatcatgg agacaaagt ggcttctgaa     900 gctctcatga agtaccacat cctgaatacc ctccagtgct ctgaggctat acaggagga     960 gcggtgtttg agaccatgga aggaaacact attgaaatag ggtgtgaggg agacagcatc    1020
tccattaacg gaatcaagat ggtgaacaag aaagacattg tgacgaagaa tggtgtcatc    1080
cacctgattg atgaagtcct cattcctgat tctgctaaac aagttattga gctggctgga    1140
aaacagcaaa ccactttcac ggacctggta gcccagttag ggttggcgtc ttctctgaag    1200
ccggatggag agtacacgct gttagcgcct gtgaacaatg cgttctctga tgacactctg    1260
agcatggacc agcgccttct taagctaatt ctgcaaaatc acatattgaa agtaaaagtc    1320
ggccttagtg atctctacaa tggacagatt ctggagacca ttggaggcaa acaactccgt    1380
```

-continued

```
gtcttcgtgt atcggacggc tatctgcata gaaaactcat gcatggtgag aggaagcaag    1440
caggggagga acggtgccat tcacatattc cgagagatca tccaaccggc ggagaagtcc    1500
ctgcacgaaa aactgcgcca agataagcgc ttcagcatct tcctcagcct cctcgaagct    1560
gcagatctga aagatcttct gacacagccc ggagattgga ccttgtttgc accaaccaat    1620
gatgccttca aggaatgac taatgaagaa agggagattc tgattgggga taaaaatgct    1680
ctccaaaaca tcattcttta ccacctgacc ccaggggttt atattggaaa gggatttgaa    1740
cccggagtca ccaacatcct gaagaccaca cagggaagca aaatctatgt gaaaggagtc    1800
aatgagacgc ttttggtgaa tgagttgaag tccaaagaat ctgacatcat gacaacaaac    1860
ggcgtcattc acgttgtgga caaactcctc tatccagcag acattccggt tggaaatgat    1920
cagctcttgg aattactgaa caaactgata aaatacatcc aaattaagtt cgttcgtggc    1980
agcaccttca agaaatccc catgactgtc tatagacctg caatgacgaa gatccacatt    2040
gaaggcgagc ctgacttcag gctgattaaa gaaggtgaaa cagtgacaga agtgatccac    2100
ggagaaccag tcattaaaaa gtacaccaaa atcatagacg gggttcctgt tgaaataact    2160
gaaaaagaga cccgggaaga acgcatcatc acaggtcctg agataaaata cactaggatt    2220
tccacaggag gtggggaaac agaagagacc ctgcagaaat tcttgcaaaa agaggtctcc    2280
aaggtcacaa agttcattga aggtggcgat ggtcacttat ttgaagatga ggcgattaaa    2340
agactgcttc agggagacac acctgcaaag aagatacaag ccaacaaaag ggttcaaggg    2400
tctagaaggc gatcaagaga aggccgttct cagtga                              2436
```

<210> SEQ ID NO 8
<211> LENGTH: 838
<212> TYPE: PRT
<213> ORGANISM: Mus musculus

<400> SEQUENCE: 8

```
Met Val Pro Leu Leu Pro Leu Tyr Ala Leu Leu Leu Phe Leu Cys
1               5                   10                  15

Asp Ile Asn Pro Ala Asn Ala Asn Ser Tyr Tyr Asp Lys Val Leu Ala
            20                  25                  30

His Ser Arg Ile Arg Gly Arg Asp Gln Gly Pro Asn Val Cys Ala Leu
        35                  40                  45

Gln Gln Ile Leu Gly Thr Lys Lys Tyr Phe Ser Ser Cys Lys Asn
    50                  55                  60

Trp Tyr Gln Gly Ala Ile Cys Gly Lys Lys Thr Val Leu Tyr Glu
65                  70                  75                  80

Cys Cys Pro Gly Tyr Met Arg Met Glu Gly Met Lys Gly Cys Pro Ala
                85                  90                  95

Val Met Pro Ile Asp His Val Tyr Gly Thr Leu Gly Ile Val Gly Ala
            100                 105                 110

Thr Thr Thr Gln His Tyr Ser Asp Val Ser Lys Leu Arg Glu Glu Ile
        115                 120                 125

Glu Gly Lys Gly Ser Tyr Thr Tyr Phe Ala Pro Ser Asn Glu Ala Trp
    130                 135                 140

Glu Asn Leu Asp Ser Asp Ile Arg Arg Gly Leu Glu Asn Asn Val Asn
145                 150                 155                 160

Val Glu Leu Leu Asn Ala Leu His Ser His Met Val Asn Lys Arg Met
                165                 170                 175

Leu Thr Lys Asp Leu Lys His Gly Met Val Ile Pro Ser Met Tyr Asn
            180                 185                 190
```

```
Asn Leu Gly Leu Phe Ile Asn His Tyr Pro Asn Gly Val Val Thr Val
            195                 200                 205

Asn Cys Ala Arg Val Ile His Gly Asn Gln Ile Ala Thr Asn Gly Val
        210                 215                 220

Val His Val Ile Asp Arg Val Leu Thr Gln Ile Gly Thr Ser Ile Gln
225                 230                 235                 240

Asp Phe Leu Glu Ala Glu Asp Leu Ser Ser Phe Arg Ala Ala Ala
                245                 250                 255

Ile Thr Ser Asp Leu Leu Glu Ser Leu Gly Arg Asp Gly His Phe Thr
                260                 265                 270

Leu Phe Ala Pro Thr Asn Glu Ala Phe Glu Lys Leu Pro Arg Gly Val
        275                 280                 285

Leu Glu Arg Ile Met Gly Asp Lys Val Ala Ser Glu Ala Leu Met Lys
        290                 295                 300

Tyr His Ile Leu Asn Thr Leu Gln Cys Ser Glu Ala Ile Thr Gly Gly
305                 310                 315                 320

Ala Val Phe Glu Thr Met Glu Gly Asn Thr Ile Glu Ile Gly Cys Glu
                325                 330                 335

Gly Asp Ser Ile Ser Ile Asn Gly Ile Lys Met Val Asn Lys Lys Asp
                340                 345                 350

Ile Val Thr Lys Asn Gly Val Ile His Leu Ile Asp Glu Val Leu Ile
        355                 360                 365

Pro Asp Ser Ala Lys Gln Val Ile Glu Leu Ala Gly Lys Gln Gln Thr
        370                 375                 380

Thr Phe Thr Asp Leu Val Ala Gln Leu Gly Leu Ala Ser Ser Leu Lys
385                 390                 395                 400

Pro Asp Gly Glu Tyr Thr Leu Leu Ala Pro Val Asn Asn Ala Phe Ser
                405                 410                 415

Asp Asp Thr Leu Ser Met Asp Gln Arg Leu Leu Lys Leu Ile Leu Gln
                420                 425                 430

Asn His Ile Leu Lys Val Lys Val Gly Leu Ser Asp Leu Tyr Asn Gly
        435                 440                 445

Gln Ile Leu Glu Thr Ile Gly Gly Lys Gln Leu Arg Val Phe Val Tyr
        450                 455                 460

Arg Thr Ala Ile Cys Ile Glu Asn Ser Cys Met Val Arg Gly Ser Lys
465                 470                 475                 480

Gln Gly Arg Asn Gly Ala Ile His Ile Phe Arg Glu Ile Ile Gln Pro
                485                 490                 495

Ala Glu Lys Ser Leu His Asp Lys Leu Arg Gln Asp Lys Arg Phe Ser
                500                 505                 510

Ile Phe Leu Ser Leu Leu Glu Ala Ala Asp Leu Lys Asp Leu Leu Thr
        515                 520                 525

Gln Pro Gly Asp Trp Thr Leu Phe Ala Pro Thr Asn Asp Ala Phe Lys
        530                 535                 540

Gly Met Thr Ser Glu Glu Arg Glu Leu Leu Ile Gly Asp Lys Asn Ala
545                 550                 555                 560

Leu Gln Asn Ile Ile Leu Tyr His Leu Thr Pro Gly Val Tyr Ile Gly
                565                 570                 575

Lys Gly Phe Glu Pro Gly Val Thr Asn Ile Leu Lys Thr Thr Gln Gly
                580                 585                 590

Ser Lys Ile Tyr Leu Lys Gly Val Asn Glu Thr Leu Leu Val Asn Glu
        595                 600                 605

Leu Lys Ser Lys Glu Ser Asp Ile Met Thr Thr Asn Gly Val Ile His
```

```
                610             615             620
Val Val Asp Lys Leu Leu Tyr Pro Ala Asp Ile Pro Val Gly Asn Asp
625             630             635             640

Gln Leu Leu Glu Leu Leu Asn Lys Leu Ile Lys Tyr Ile Gln Ile Lys
                645             650             655

Phe Val Arg Gly Ser Thr Phe Lys Glu Ile Pro Met Thr Val Tyr Thr
            660             665             670

Thr Lys Ile Ile Thr Lys Val Val Glu Pro Lys Ile Lys Val Ile Gln
                675             680             685

Gly Ser Leu Gln Pro Ile Ile Lys Thr Glu Gly Pro Ala Met Thr Lys
690             695             700

Ile Gln Ile Glu Gly Asp Pro Asp Phe Arg Leu Ile Lys Glu Gly Glu
705             710             715             720

Thr Val Thr Glu Val Ile His Gly Glu Pro Val Ile Lys Lys Tyr Thr
                725             730             735

Lys Ile Ile Asp Gly Val Pro Val Glu Ile Thr Glu Lys Gln Thr Arg
            740             745             750

Glu Glu Arg Ile Ile Thr Gly Pro Glu Ile Lys Tyr Thr Arg Ile Ser
                755             760             765

Thr Gly Gly Glu Thr Gly Glu Thr Leu Gln Lys Phe Leu Gln Lys
770             775             780

Glu Val Ser Lys Val Thr Lys Phe Ile Glu Gly Asp Gly His Leu
785             790             795             800

Phe Glu Asp Glu Glu Ile Lys Arg Leu Leu Gln Gly Asp Thr Pro Ala
                805             810             815

Lys Lys Ile Pro Ala Asn Lys Arg Val Gln Gly Pro Arg Arg Ser
                820             825             830

Arg Glu Gly Arg Ser Gln
        835

<210> SEQ ID NO 9
<211> LENGTH: 2517
<212> TYPE: DNA
<213> ORGANISM: Mus musculus

<400> SEQUENCE: 9
atggttcctc tcctgccctt atatgctctg ctgctgctgt tcctgtgtga tattaaccct     60
gcaaatgcca acagttacta tgacaaggtc ctggctcaca gccgcatcag ggtcgggat    120 cagggcccaa acgtctgtgc cctccagcaa attctgggca ccaaaaagaa atacttcagc    180
tcctgtaaga actggtatca aggtgctatc tgcgggaaga aaaccactgt gctatatgaa    240
tgctgccctg ctatatgag aatggaaggg atgaaaggct cccccgcagt gatgcctatt    300
gaccatgttt atggcacgct gggcattgtg ggagccacta ccactcagca ctactccgat    360
gtctcgaagc tgagagaaga gattgaagga aaagggtcat acacgtactt cgcgccgagt    420
aacgaggctt gggagaacct ggattctgac attcgcagag actggagaa caatgtcaat    480 gttgagctac tgaatgcctt acacagccac atggttaata agagaatgtt aaccaaggac    540
ctgaaacacg gcatggttat tccttcaatg tacaacaatc tggggcttttt tattaaccat    600 tatcccaatg ggggttgtcac tgtgaactgt gctcgagtca tccatgggaa ccagattgcc    660
acaaatggtg tcgtccatgt cattgaccgt gtcctgacac aaattggtac ctccatccaa    720
gacttccttg aagcagaaga cgacctttca tcatttagag cagccgccat cacctctgac    780
ctcttggagt cccttggaag agatggtcac ttcacgctct ttgctcccac caatgaagct    840
```

```
ttcgagaaac tgccacgagg tgtcctagaa aggatcatgg agacaaagt ggcttctgaa      900
gctctcatga agtaccacat cctaaatacc ctccagtgct ctgaggccat cactggagga     960
gccgtgtttg agaccatgga aggaaacact attgagatag gtgcgaagg ggacagtatc     1020
tccattaacg gaatcaagat ggtgaacaag aaagacattg tgactaagaa tggtgtcatc    1080
cacctgattg atgaagtcct cattcctgat tctgccaaac aagttattga gctggctgga    1140
aaacagcaaa ccactttcac cgacctggta gcccaattag gcttggcatc ctctctgaag    1200
ccagatggag agtacacctt attagcacct gtgaacaatg cgttctctga tgacactctg    1260
agcatggacc aacgccttct taagctaatt ctgcaaaatc acatattgaa agtaaaagtt    1320
ggccttagcg acctctacaa tggacagata ctggaaacca ttggaggcaa acaactccga    1380
gtctttgtgt atcggacggc tatctgcata gaaaactcat gcatggtgag aggaagcaag    1440
cagggaagga atggtgccat tcacatattc gagaaatca tccaaccagc agagaaatcc     1500
ctgcacgaca agctgcggca agacaagcgc tttagcatct tcctcagcct ccttgaagct    1560
gcagatttga agatctcct gacacagccc ggagattgga ccttgtttgc accaaccaat     1620
gatgccttca agggaatgac tagcgaagaa agggagcttc tgattgggga taaaaatgct    1680
ctccaaaaca tcattcttta tcacctgacc ccaggggttt atattggaaa gggattcgaa    1740
cccggagtca ctaatatcct gaagaccaca caggaagca aatctatct gaaggagta      1800
aacgaaacgc ttctagtgaa tgagttgaag tccaagaat ctgacatcat gacgacaaat    1860
ggtgtcatcc acgtcgtgga caaactcctc tatccagcag atattccagt tggaaatgat    1920
cagctcttgg aattactgaa caaactgata aaatacatcc aaatcaagtt tgttcgtggc    1980
agcaccttca agaaatccc catgactgtc tatacaacta aaattataac caaagtcgtg    2040
gaaccaaaaa ttaaagtcat tcaaggcagt cttcagccta ttatcaaaac ggaaggacct    2100
gcaatgacga agatccaaat tgaaggtgat cccgacttca ggctgattaa agaaggcgaa    2160
acggtgacag aagtgatcca cggagagcca gtcattaaaa agtacaccaa aatcatagat    2220
ggagttcctg ttgaaataac tgaaaaacag actcgggaag aacgaatcat acaggtcct    2280
gagataaaat ataccaggat ttccacagga ggtgagaaa caggagagac cttgcagaaa    2340
ttcttgcaaa agaggtctc caaggtcaca aagttcattg aaggtggcga tggtcactta    2400
tttgaagatg aggagattaa aagactgctt caggagaca cacctgcaaa gaagatacca    2460
gccaacaaaa gggttcaagg gcctagaaga cgatcaagag aaggccgttc tcagtga       2517
```

<210> SEQ ID NO 10
<211> LENGTH: 811
<212> TYPE: PRT
<213> ORGANISM: Mus musculus

<400> SEQUENCE: 10

Met Val Pro Leu Leu Pro Leu Tyr Ala Leu Leu Leu Phe Leu Cys
1               5                   10                  15

Asp Ile Asn Pro Ala Asn Ala Asn Ser Tyr Tyr Asp Lys Val Leu Ala
        20                  25                  30

His Ser Arg Ile Arg Gly Arg Asp Gln Gly Pro Asn Val Cys Ala Leu
        35                  40                  45

Gln Gln Ile Leu Gly Thr Lys Lys Lys Tyr Phe Ser Ser Cys Lys Asn
    50                  55                  60

Trp Tyr Gln Gly Ala Ile Cys Gly Lys Lys Thr Thr Val Leu Tyr Glu
65                  70                  75                  80

Cys Cys Pro Gly Tyr Met Arg Met Glu Gly Met Lys Gly Cys Pro Ala

-continued

```
                85                  90                  95
Val Met Pro Ile Asp His Val Tyr Gly Thr Leu Gly Ile Val Gly Ala
            100                 105                 110

Thr Thr Thr Gln His Tyr Ser Asp Val Ser Lys Leu Arg Glu Glu Ile
            115                 120                 125

Glu Gly Lys Gly Ser Tyr Thr Tyr Phe Ala Pro Ser Asn Glu Ala Trp
            130                 135                 140

Glu Asn Leu Asp Ser Asp Ile Arg Arg Gly Leu Glu Asn Asn Val Asn
145                 150                 155                 160

Val Glu Leu Leu Asn Ala Leu His Ser His Met Val Asn Lys Arg Met
            165                 170                 175

Leu Thr Lys Asp Leu Lys His Gly Met Val Ile Pro Ser Met Tyr Asn
            180                 185                 190

Asn Leu Gly Leu Phe Ile Asn His Tyr Pro Asn Gly Val Val Thr Val
            195                 200                 205

Asn Cys Ala Arg Val Ile His Gly Asn Gln Ile Ala Thr Asn Gly Val
            210                 215                 220

Val His Val Ile Asp Arg Val Leu Thr Gln Ile Gly Thr Ser Ile Gln
225                 230                 235                 240

Asp Phe Leu Glu Ala Glu Asp Leu Ser Ser Phe Arg Ala Ala Ala
            245                 250                 255

Ile Thr Ser Asp Leu Leu Glu Ser Leu Gly Arg Asp Gly His Phe Thr
            260                 265                 270

Leu Phe Ala Pro Thr Asn Glu Ala Phe Glu Lys Leu Pro Arg Gly Val
            275                 280                 285

Leu Glu Arg Ile Met Gly Asp Lys Val Ala Ser Glu Ala Leu Met Lys
            290                 295                 300

Tyr His Ile Leu Asn Thr Leu Gln Cys Ser Glu Ala Ile Thr Gly Gly
305                 310                 315                 320

Ala Val Phe Glu Thr Met Glu Gly Asn Thr Ile Glu Ile Gly Cys Glu
            325                 330                 335

Gly Asp Ser Ile Ser Ile Asn Gly Ile Lys Met Val Asn Lys Lys Asp
            340                 345                 350

Ile Val Thr Lys Asn Gly Val Ile His Leu Ile Asp Glu Val Leu Ile
            355                 360                 365

Pro Asp Ser Ala Lys Gln Val Ile Glu Leu Ala Gly Lys Gln Gln Thr
            370                 375                 380

Thr Phe Thr Asp Leu Val Ala Gln Leu Gly Leu Ala Ser Ser Leu Lys
385                 390                 395                 400

Pro Asp Gly Glu Tyr Thr Leu Leu Ala Pro Val Asn Asn Ala Phe Ser
            405                 410                 415

Asp Asp Thr Leu Ser Met Asp Gln Arg Leu Leu Lys Leu Ile Leu Gln
            420                 425                 430

Asn His Ile Leu Lys Val Lys Val Gly Leu Ser Asp Leu Tyr Asn Gly
            435                 440                 445

Gln Ile Leu Glu Thr Ile Gly Gly Lys Gln Leu Arg Val Phe Val Tyr
            450                 455                 460

Arg Thr Ala Ile Cys Ile Glu Asn Ser Cys Met Val Arg Gly Ser Lys
465                 470                 475                 480

Gln Gly Arg Asn Gly Ala Ile His Ile Phe Arg Glu Ile Ile Gln Pro
            485                 490                 495

Ala Glu Lys Ser Leu His Asp Lys Leu Arg Gln Asp Lys Arg Phe Ser
            500                 505                 510
```

```
Ile Phe Leu Ser Leu Leu Glu Ala Ala Asp Leu Lys Asp Leu Leu Thr
         515                 520                 525
Gln Pro Gly Asp Trp Thr Leu Phe Ala Pro Thr Asn Asp Ala Phe Lys
     530                 535                 540
Gly Met Thr Ser Glu Glu Arg Glu Leu Leu Ile Gly Asp Lys Asn Ala
545                 550                 555                 560
Leu Gln Asn Ile Ile Leu Tyr His Leu Thr Pro Gly Val Tyr Ile Gly
                 565                 570                 575
Lys Gly Phe Glu Pro Gly Val Thr Asn Ile Leu Lys Thr Thr Gln Gly
             580                 585                 590
Ser Lys Ile Tyr Leu Lys Gly Val Asn Glu Thr Leu Leu Val Asn Glu
         595                 600                 605
Leu Lys Ser Lys Glu Ser Asp Ile Met Thr Thr Asn Gly Val Ile His
     610                 615                 620
Val Val Asp Lys Leu Leu Tyr Pro Ala Asp Ile Pro Val Gly Asn Asp
625                 630                 635                 640
Gln Leu Leu Glu Leu Leu Asn Lys Leu Ile Lys Tyr Ile Gln Ile Lys
                 645                 650                 655
Phe Val Arg Gly Ser Thr Phe Lys Glu Ile Pro Met Thr Val Tyr Arg
             660                 665                 670
Pro Ala Met Thr Lys Ile Gln Ile Glu Gly Asp Pro Asp Phe Arg Leu
         675                 680                 685
Ile Lys Glu Gly Glu Thr Val Thr Glu Val Ile His Gly Glu Pro Val
     690                 695                 700
Ile Lys Lys Tyr Thr Lys Ile Ile Asp Gly Val Pro Val Glu Ile Thr
705                 710                 715                 720
Glu Lys Gln Thr Arg Glu Glu Arg Ile Ile Thr Gly Pro Glu Ile Lys
                 725                 730                 735
Tyr Thr Arg Ile Ser Thr Gly Gly Glu Thr Gly Glu Thr Leu Gln
             740                 745                 750
Lys Phe Leu Gln Lys Glu Val Ser Lys Val Thr Lys Phe Ile Glu Gly
         755                 760                 765
Gly Asp Gly His Leu Phe Glu Asp Glu Ile Lys Arg Leu Leu Gln
     770                 775                 780
Gly Asp Thr Pro Ala Lys Lys Ile Pro Ala Asn Lys Arg Val Gln Gly
785                 790                 795                 800
Pro Arg Arg Arg Ser Arg Glu Gly Arg Ser Gln
                 805                 810

<210> SEQ ID NO 11
<211> LENGTH: 2436
<212> TYPE: DNA
<213> ORGANISM: Mus musculus

<400> SEQUENCE: 11
atggttcctc tcctgccctt atatgctctg ctgctgctgt tcctgtgtga tattaaccct      60
gcaaatgcca acagttacta tgacaaggtc ctggctcaca gccgcatcag ggtcgggat     120 cagggcccaa acgtctgtgc cctccagcaa attctgggca ccaaaaagaa atacttcagc    180
tcctgtaaga actggtatca aggtgctatc tgcgggaaga aaaccactgt gctatatgaa    240
tgctgccctg gctatatgag aatggaaggg atgaaaggct gccccgcagt gatgcctatt    300
gaccatgttt atggcacgct gggcattgtg ggagccacta ccactcagca ctactccgat    360
gtctcgaagc tgagagaaga gattgaagga aagggtcat acacgtactt cgcgccgagt    420
aacgaggctt gggagaacct ggattctgac attcgcagag gactggagaa caatgtcaat    480
```

```
gttgagctac tgaatgcctt acacagccac atggttaata agagaatgtt aaccaaggac      540
ctgaaacacg gcatggttat tccttcaatg tacaacaatc tggggctttt tattaaccat      600
tatcccaatg gggttgtcac tgtgaactgt gctcgagtca tccatgggaa ccagattgcc      660
acaaatggtg tcgtccatgt cattgaccgt gtcctgacac aaattggtac ctccatccaa      720
gacttccttg aagcagaaga cgacctttca tcatttagag cagccgccat cacctctgac      780
ctcttggagt cccttggaag agatggtcac ttcacgctct ttgctcccac caatgaagct      840
ttcgagaaac tgccacgagg tgtcctagaa aggatcatgg gagacaaagt ggcttctgaa      900
gctctcatga agtaccacat cctaaatacc ctccagtgct ctgaggccat cactggagga      960
gccgtgtttg agaccatgga aggaaacact attgagatag ggtgcgaagg ggacagtatc     1020
tccattaacg gaatcaagat ggtgaacaag aaagacattg tgactaagaa tggtgtcatc     1080
cacctgattg atgaagtcct cattcctgat tctgccaaac aagttattga gctggctgga     1140
aaacagcaaa ccactttcac cgacctggta gcccaattag gcttggcatc ctctctgaag     1200
ccagatggag agtacacctt attagcacct gtgaacaatg cgttctctga tgacactctg     1260
agcatggacc aacgccttct taagctaatt ctgcaaaatc acatattgaa agtaaaagtt     1320
ggccttagcg acctctacaa tggacagata ctggaaacca ttggaggcaa acaactccga     1380
gtctttgtgt atcggacggc tatctgcata gaaaactcat gcatggtgag aggaagcaag     1440
cagggaagga atggtgccat tcacatattc cgagaaatca tccaaccagc agagaaatcc     1500
ctgcacgaca agctgcggca agacaagcgc tttagcatct tcctcagcct ccttgaagct     1560
gcagatttga aagatctcct gacacagccc ggagattgga ccttgtttgc accaaccaat     1620
gatgccttca agggaatgac tagcgaagaa agggagcttc tgattgggga taaaaatgct     1680
ctccaaaaca tcattctttta tcacctgacc ccaggggttt atattggaaa gggattcgaa     1740
cccggagtca ctaatatcct gaagaccaca cagggaagca aaatctatct gaaaggagta     1800
aacgaaacgc ttctagtgaa tgagttgaag tccaaagaat ctgacatcat gacgacaaat     1860
ggtgtcatcc acgtcgtgga caaactcctc tatccagcag atattccagt tggaaatgat     1920
cagctcttgg aattactgaa caaactgata aaatacatcc aaatcaagtt tgttcgtggc     1980
agcaccttca aagaaatccc catgactgtc tatagacctg caatgacgaa gatccaaatt     2040
gaaggtgatc ccgacttcag gctgattaaa gaaggcgaaa cggtgacaga agtgatccac     2100
ggagagccag tcattaaaaa gtacaccaaa atcatagatg gagttcctgt tgaaataact     2160
gaaaaacaga ctcgggaaga acgaatcatt acaggtcctg agataaaata taccaggatt     2220
tccacaggag gtggagaaac aggagagacc ttgcagaaat tcttgcaaaa agaggtctcc     2280
aaggtcacaa agttcattga aggtggcgat ggtcacttat ttgaagatga ggagattaaa     2340
agactgcttc agggagacac acctgcaaag aagataccag ccaacaaaag ggttcaaggg     2400
cctagaagac gatcaagaga aggccgttct cagtga                              2436
```

```
<210> SEQ ID NO 12
<211> LENGTH: 2511
<212> TYPE: DNA
<213> ORGANISM: Homo sapiens

<400> SEQUENCE: 12
```

```
atgattccct ttttacccat gttttctcta ctattgctgc ttattgttaa ccctataaac       60
gccaacaatc attatgacaa gatcttggct catagtcgta tcagggggtcg ggaccaaggc      120 ccaaatgtct gtgcccttca acagattttg ggcaccaaaa agaaatactt cagcacttgt      180
```

```
aagaactggt ataaaaagtc catctgtgga cagaaaacga ctgttttata tgaatgttgc    240
cctggttata tgagaatgga aggaatgaaa ggctgcccag cagttttgcc cattgaccat    300
gtttatggca ctctgggcat cgtgggagcc accacaacgc agcgctattc tgacgcctca    360
aaactgaggg aggagatcga gggaaaggga tccttcactt actttgcacc gagtaatgag    420
gcttgggaca acttggattc tgatatccgt agaggtttgg agagcaacgt gaatgttgaa    480
ttactgaatg ctttacatag tcacatgatt aataagagaa tgttgaccaa ggacttaaaa    540
aatggcatga ttattccttc aatgtataac aatttggggc ttttcattaa ccattatcct    600
aatggggttg tcactgttaa ttgtgctcga atcatccatg gaaccagat tgcaacaaat    660 ggtgttgtcc atgtcattga ccgtgtgctt acacaaattg gtacctcaat tcaagacttc    720
attgaagcag aagatgacct ttcatctttt agagcagctg ccatcacatc ggacatattg    780
gaggcccttg aagagacgg tcacttcaca ctctttgctc ccaccaatga ggcttttgag    840
aaacttccac gaggtgtcct agaaaggttc atgggagaca agtggcttc cgaagctctt    900 atgaagtacc acatcttaaa tactctccag tgttctgagt ctattatggg aggagcagtc    960
tttgagacgc tggaaggaaa tacaattgag ataggatgtg acggtgacag tataacagta   1020
aatggaatca aatggtgaa caaaaaggat attgtgacaa ataatggtgt gatccatttg   1080
attgatcagg tcctaattcc tgattctgcc aaacaagtta ttgagctggc tggaaaacag   1140
caaaccacct tcacggatct tgtggcccaa ttaggcttgg catctgctct gaggccagat   1200
ggagaataca ctttgctggc acctgtgaat aatgcatttt ctgatgatac tctcagcatg   1260
gttcagcgcc tccttaaatt aattctgcag aatcacatat tgaaagtaaa agttggcctt   1320
aatgagcttt acaacgggca atactggaaa accatcggag gcaaacagct cagagtcttc   1380
gtatatcgta cagctgtctg cattgaaaat tcatgcatgg agaaagggag taagcaaggg   1440
agaaacggtg cgattcacat attccgcgag atcatcaagc cagcagagaa atccctccat   1500
gaaaagttaa acaagataa gcgctttagc accttcctca gcctacttga agctgcagac   1560
ttgaaagagc tcctgacaca acctggagac tggacattat ttgtgccaac caatgatgct   1620
tttaagggaa tgactagtga agaaaaagaa attctgatac gggacaaaaa tgctcttcaa   1680
aacatcattc tttatcacct gacaccagga gttttcattg aaaaggatt tgaacctggt   1740 gttactaaca tttaaagac cacacaagga agcaaaatct ttctgaaaga agtaaatgat   1800
acacttctgg tgaatgaatt gaaatcaaaa gaatctgaca tcatgacaac aaatggtgta   1860
attcatgttg tagataaact cctctatcca gcagacacac ctgttggaaa tgatcaactg   1920
ctggaaatac ttaataaatt aatcaaatac atccaaatta gtttgttcg tggtagcacc   1980 ttcaaagaaa tccccgtgac tgtctataca actaaaatta taaccaaagt tgtggaacca   2040
aaaattaaag tgattgaagg cagtcttcag cctattatca aaactgaagg acccacacta   2100
acaaaagtca aaattgaagg tgaacctgaa ttcagactga ttaaagaagg tgaaacaata   2160
actgaagtga tccatggaga gccaattatt aaaaaatata ccaaaatcat tgatggagtg   2220
cctgtggaaa taactgaaaa agagacacga gaagaacgaa tcattacagg tcctgaaata   2280
aaatacacta ggatttctac tggaggtgga gaaacagaag aaactctgaa gaaattgtta   2340
caagaagagg tcaccaaggt caccaaattc attgaaggtg gtgatggtca tttatttgaa   2400
gatgaagaaa ttaaaagact gcttcaggga gacacacccg tgaggaagtt gcaagccaac   2460
aaaaaagttc aaggttctag aagacgatta agggaaggtc gttctcagtg a            2511
```

```
<210> SEQ ID NO 13
<211> LENGTH: 809
<212> TYPE: PRT
<213> ORGANISM: Homo sapiens

<400> SEQUENCE: 13

Met Ile Pro Phe Leu Pro Met Phe Ser Leu Leu Leu Leu Ile Val
 1               5                  10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Phe Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
    370                 375                 380

Thr Asp Leu Val Ala Gln Leu Gly Leu Ala Ser Ala Leu Arg Pro Asp
```

-continued

```
            385                 390                 395                 400
Gly Glu Tyr Thr Leu Leu Ala Pro Val Asn Asn Ala Phe Ser Asp Asp
                405                 410                 415

Thr Leu Ser Met Val Gln Arg Leu Leu Lys Leu Ile Leu Gln Asn His
            420                 425                 430

Ile Leu Lys Val Lys Val Gly Leu Asn Glu Leu Tyr Asn Gly Gln Ile
            435                 440                 445

Leu Glu Thr Ile Gly Gly Lys Gln Leu Arg Val Phe Val Tyr Arg Thr
    450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
            515                 520                 525

Gly Asp Trp Thr Leu Phe Val Pro Thr Asn Asp Ala Phe Lys Gly Met
    530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
            595                 600                 605

Ser Lys Glu Ser Asp Ile Met Thr Thr Asn Gly Val Ile His Val Val
    610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Arg Pro Thr
            660                 665                 670

Leu Thr Lys Val Lys Ile Glu Gly Glu Pro Glu Phe Arg Leu Ile Lys
            675                 680                 685

Glu Gly Glu Thr Ile Thr Glu Val Ile His Gly Glu Pro Ile Ile Lys
    690                 695                 700

Lys Tyr Thr Lys Ile Ile Asp Gly Val Pro Val Glu Ile Thr Glu Lys
705                 710                 715                 720

Glu Thr Arg Glu Glu Arg Ile Ile Thr Gly Pro Glu Ile Lys Tyr Thr
                725                 730                 735

Arg Ile Ser Thr Gly Gly Gly Thr Glu Glu Thr Leu Lys Lys Leu
            740                 745                 750

Leu Gln Glu Glu Val Thr Lys Val Thr Lys Phe Ile Glu Gly Gly Asp
            755                 760                 765

Gly His Leu Phe Glu Asp Glu Ile Lys Arg Leu Leu Gln Gly Asp
    770                 775                 780

Thr Pro Val Arg Lys Leu Gln Ala Asn Lys Lys Val Gln Gly Ser Arg
785                 790                 795                 800

Arg Arg Leu Arg Glu Gly Arg Ser Gln
                805
```

<210> SEQ ID NO 14
<211> LENGTH: 2430
<212> TYPE: DNA
<213> ORGANISM: Homo sapiens

<400> SEQUENCE: 14

```
atgattccct ttttacccat gttttctcta ctattgctgc ttattgttaa ccctataaac      60
gccaacaatc attatgacaa gatcttggct catagtcgta tcaggggtcg ggaccaaggc     120
ccaaatgtct gtgccttca acagattttg gcaccaaaa agaaatactt cagcacttgt      180
aagaactggt ataaaagtc catctgtgga cagaaaacga ctgttttata tgaatgttgc     240
cctggttata tgagaatgga aggaatgaaa ggctgcccag cagttttgcc cattgaccat     300
gtttatggca ctctgggcat cgtgggagcc accacaacgc agcgctattc tgacgcctca     360
aaactgaggg aggagatcga gggaaaggga tccttcactt actttgcacc gagtaatgag     420
gcttgggaca acttggattc tgatatccgt agaggtttgg agagcaacgt gaatgttgaa     480
ttactgaatg ctttacatag tcacatgatt aataagagaa tgttgaccaa ggacttaaaa     540
aatggcatga ttattccttc aatgtataac aatttggggc ttttcattaa ccattatcct     600
aatggggttg tcactgttaa ttgtgctcga atcatccatg gaaccagat tgcaacaaat     660
ggtgttgtcc atgtcattga ccgtgtgctt acacaaattg gtacctcaat tcaagacttc     720
attgaagcag aagatgacct ttcatctttt agagcagctg ccatcacatc ggacatattg     780
gaggcccttg aagagacgg tcacttcaca ctctttgctc ccaccaatga ggcttttgag     840
aaacttccac gaggtgtcct agaaaggttc atgggagaca agtggcttc cgaagctctt     900
atgaagtacc acatcttaaa tactctccag tgttctgagt ctattatggg aggagcagtc     960
tttgagacgc tggaaggaaa tacaattgag ataggatgtg acggtgacag tataacagta    1020
aatgaaatca aaatggtgaa caaaaggat attgtgacaa ataatggtgt gatccatttg    1080
attgatcagg tcctaattcc tgattctgcc aaacaagtta ttgagctggc tggaaaacag    1140
caaaccacct tcacggatct gtggcccaa ttaggcttgg catctgctct gaggccagat    1200
ggagaataca ctttgctggc acctgtgaat aatgcatttt ctgatgatac tctcagcatg    1260
gttcagcgcc tccttaaatt aattctgcag aatcacatat tgaaagtaaa agttggcctt    1320
aatgagcttt acaacgggca aatactggaa accatcggag gcaaacagct cagagtcttc    1380
gtatatcgta cagctgtctg cattgaaaat tcatgcatgg agaaagggag taagcaaggg    1440
agaaacggtg cgattcacat attccgcgag atcatcaagc cagcagagaa atccctccat    1500
gaaaagttaa acaagataa gcgctttagc accttcctca gcctacttga agctgcagac    1560
ttgaaagagc tcctgacaca acctggagac tggactattat ttgtgccaac caatgatgct    1620
tttaagggaa tgactagtga agaaaaagaa attctgatac gggacaaaaa tgctcttcaa    1680
aacatcattc tttatcacct gacaccagga gttttcattg aaaaggatt tgaacctggt    1740
gttactaaca ttttaaagac cacacaagga agcaaaatct ttctgaaaga agtaaatgat    1800
acacttctgg tgaatgaatt gaaatcaaaa gaatctgaca tcatgacaac aaatggtgta    1860
attcatgttg tagataaact cctctatcca gcagacacac tgttggaaa tgatcaactg    1920
ctggaaatac ttaataaatt aatcaaatac atccaaatta gtttgttcg tggtagcacc    1980
ttcaaagaaa tccccgtgac tgtctataga cccacactaa caaagtcaa aattgaaggt    2040
gaacctgaat tcagactgat taagaaggt gaaacaataa ctgaagtgat ccatggagag    2100
ccaattatta aaaatacac caaatcatt gatggagtgc ctgtggaaat aactgaaaaa    2160
```

```
gagacacgag aagaacgaat cattacaggt cctgaaataa aatacactag gatttctact    2220
ggaggtggag aaacagaaga aactctgaag aaattgttac aagaagaggt caccaaggtc    2280
accaaattca ttgaaggtgg tgatggtcat ttatttgaag atgaagaaat taaaagactg    2340
cttcagggag acacccgt gaggaagttg caagccaaca aaaagttca aggttctaga      2400 agacgattaa gggaaggtcg ttctcagtga                                    2430
```

<210> SEQ ID NO 15
<211> LENGTH: 23
<212> TYPE: DNA
<213> ORGANISM: Artificial Sequence
<220> FEATURE:
<223> OTHER INFORMATION: Primer No.1

<400> SEQUENCE: 15

```
gttcattgaa ggtggcgatg gtc                                             23
```

<210> SEQ ID NO 16
<211> LENGTH: 24
<212> TYPE: DNA
<213> ORGANISM: Artificial Sequence
<220> FEATURE:
<223> OTHER INFORMATION: Primer No.2

<400> SEQUENCE: 16

```
gagataaaat ccctgcatgg tcct                                            24
```

<210> SEQ ID NO 17
<211> LENGTH: 25
<212> TYPE: DNA
<213> ORGANISM: Artificial Sequence
<220> FEATURE:
<223> OTHER INFORMATION: Primer No. 3

<400> SEQUENCE: 17

```
cacggtcgat gacatggaca acacc                                           25
```

<210> SEQ ID NO 18
<211> LENGTH: 22
<212> TYPE: DNA
<213> ORGANISM: Artificial Sequence
<220> FEATURE:
<223> OTHER INFORMATION: Primer No. 4

<400> SEQUENCE: 18

```
acggagctca gggctgaaga tg                                              22
```

<210> SEQ ID NO 19
<211> LENGTH: 22
<212> TYPE: DNA
<213> ORGANISM: Artificial Sequence
<220> FEATURE:
<223> OTHER INFORMATION: Primer No. 5

<400> SEQUENCE: 19

```
gacccgggaa gaacgcatca tc                                              22
```

<210> SEQ ID NO 20
<211> LENGTH: 32
<212> TYPE: DNA
<213> ORGANISM: Artificial Sequence
<220> FEATURE:
<223> OTHER INFORMATION: Primer No. 6

<400> SEQUENCE: 20
tgggtgaccc tgagaacggc cttctcttga tc								32

<210> SEQ ID NO 21
<211> LENGTH: 27
<212> TYPE: PRT
<213> ORGANISM: Mus musculus

<400> SEQUENCE: 21

Thr Thr Lys Ile Ile Thr Lys Val Val Glu Pro Lys Ile Lys Val Ile
1               5                   10                  15

Glu Gly Ser Leu Gln Pro Ile Ile Lys Thr Glu
            20                  25

<210> SEQ ID NO 22
<211> LENGTH: 9
<212> TYPE: PRT
<213> ORGANISM: Homo sapiens

<400> SEQUENCE: 22

Thr Thr Lys Ile Ile Thr Lys Val Val
1               5

<210> SEQ ID NO 23
<211> LENGTH: 9
<212> TYPE: PRT
<213> ORGANISM: Rattus sp.

<400> SEQUENCE: 23

Thr Thr Lys Ile Ile Thr Lys Leu Val
1               5

<210> SEQ ID NO 24
<211> LENGTH: 9
<212> TYPE: PRT
<213> ORGANISM: Mus musculus

<400> SEQUENCE: 24

Thr Thr Lys Ile Ile Thr Lys Val Val
1               5

<210> SEQ ID NO 25
<211> LENGTH: 28
<212> TYPE: PRT
<213> ORGANISM: Homo sapiens

<400> SEQUENCE: 25

Cys Thr Thr Lys Ile Ile Thr Lys Val Val Glu Pro Lys Ile Lys Val Ile
1               5                   10                  15

Glu Gly Ser Leu Gln Pro Ile Ile Lys Thr Glu
            20                  25

<210> SEQ ID NO 26
<211> LENGTH: 10
<212> TYPE: PRT
<213> ORGANISM: Homo sapiens

<400> SEQUENCE: 26

Tyr Thr Thr Lys Ile Ile Thr Lys Val Val
1               5                   10

<210> SEQ ID NO 27
<211> LENGTH: 32
<212> TYPE: DNA
<213> ORGANISM: Artificial Sequence
<220> FEATURE:

<223> OTHER INFORMATION: Primer No.7

<400> SEQUENCE: 27
aagctagcca ccatgattcc cttttttaccc at                            32

<210> SEQ ID NO 28
<211> LENGTH: 20
<212> TYPE: DNA
<213> ORGANISM: Artificial Sequence
<220> FEATURE:
<223> OTHER INFORMATION: Primer No.8

<400> SEQUENCE: 28
aactccacaa tttccctcat                                          20

<210> SEQ ID NO 29
<211> LENGTH: 21
<212> TYPE: DNA
<213> ORGANISM: Artificial Sequence
<220> FEATURE:
<223> OTHER INFORMATION: Primer No. 9

<400> SEQUENCE: 29
taaccaaagt tgtggaacca a                                        21

<210> SEQ ID NO 30
<211> LENGTH: 20
<212> TYPE: DNA
<213> ORGANISM: Artificial Sequence
<220> FEATURE:
<223> OTHER INFORMATION: Primer No. 10

<400> SEQUENCE: 30
tgtgtctccc tgaagcagtc                                          20

<210> SEQ ID NO 31
<211> LENGTH: 21
<212> TYPE: DNA
<213> ORGANISM: Artificial Sequence
<220> FEATURE:
<223> OTHER INFORMATION: Primer No. 11

<400> SEQUENCE: 31
catcaccatc accatcacta a                                        21

<210> SEQ ID NO 32
<211> LENGTH: 56
<212> TYPE: DNA
<213> ORGANISM: Artificial Sequence
<220> FEATURE:
<223> OTHER INFORMATION: Primer No. 12

<400> SEQUENCE: 32
ctagaagacg attaagggaa ggtcgttctc agctggaagt tctgttccag gggccc   56

<210> SEQ ID NO 33
<211> LENGTH: 52
<212> TYPE: DNA
<213> ORGANISM: Artificial Sequence
<220> FEATURE:
<223> OTHER INFORMATION: Primer No. 13

<400> SEQUENCE: 33
gggcccctgg aacagaactt ccagctgaga acgaccttcc cttaatcgtc tt       52

<210> SEQ ID NO 34

```
<211> LENGTH: 6
<212> TYPE: PRT
<213> ORGANISM: Homo sapiens

<400> SEQUENCE: 34

Thr Thr Lys Ile Ile Thr
1               5

<210> SEQ ID NO 35
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 35

Phe Lys Glu Ile Pro Val Thr Val Tyr Thr
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 36

Lys Glu Ile Pro Val Thr Val Tyr Thr Thr
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 37

Glu Ile Pro Val Thr Val Tyr Thr Thr Lys
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 38

Ile Pro Val Thr Val Tyr Thr Thr Lys Ile
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 39

Pro Val Thr Val Tyr Thr Thr Lys Ile Ile
1               5                   10

<210> SEQ ID NO 40
<211> LENGTH: 10
<212> TYPE: PRT
<213> ORGANISM: Artificial Sequence
<220> FEATURE:
```

<223> OTHER INFORMATION: Chemically Synthesized

<400> SEQUENCE: 40

Val Thr Val Tyr Thr Thr Lys Ile Ile Thr
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 41

Thr Val Tyr Thr Thr Lys Ile Ile Thr Lys
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 42

Val Tyr Thr Thr Lys Ile Ile Thr Lys Val
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 43

Tyr Thr Thr Lys Ile Ile Thr Lys Val Val
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 44

Thr Thr Lys Ile Ile Thr Lys Val Val Glu
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 45

Thr Lys Ile Ile Thr Lys Val Val Glu Pro
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Chemically Synthesized -continued

```
<400> SEQUENCE: 46

Lys Ile Ile Thr Lys Val Val Glu Pro Lys
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 47

Ile Ile Thr Lys Val Val Glu Pro Lys Ile
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Chemicallly Synthesized

<400> SEQUENCE: 48

Ile Thr Lys Val Val Glu Pro Lys Ile Lys
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 49

Thr Lys Val Val Glu Pro Lys Ile Lys Val
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 50

Lys Val Val Glu Pro Lys Ile Lys Val Ile
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 51

Val Val Glu Pro Lys Ile Lys Val Ile Glu
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 52
```

```
Val Glu Pro Lys Ile Lys Val Ile Glu Gly
1               5                   10
```

<210> SEQ ID NO 53
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 53

```
Glu Pro Lys Ile Lys Val Ile Glu Gly Ser
1               5                   10
```

<210> SEQ ID NO 54
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 54

```
Pro Lys Ile Lys Val Ile Glu Gly Ser Leu
1               5                   10
```

<210> SEQ ID NO 55
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 55

```
Lys Ile Lys Val Ile Glu Gly Ser Leu Gln
1               5                   10
```

<210> SEQ ID NO 56
<211> LENGTH: 10
<212> TYPE: PRT
<213> ORGANISM: Artificial Sequence
<220> FEATURE:
<223> OTHER INFORMATION: ChemicalySynthesized

<400> SEQUENCE: 56

```
Ile Lys Val Ile Glu Gly Ser Leu Gln Pro
1               5                   10
```

<210> SEQ ID NO 57
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 57

```
Lys Val Ile Glu Gly Ser Leu Gln Pro Ile
1               5                   10
```

<210> SEQ ID NO 58
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 58

```
Val Ile Glu Gly Ser Leu Gln Pro Ile Ile
1               5                   10
```

```
<210> SEQ ID NO 59
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 59

Ile Glu Gly Ser Leu Gln Pro Ile Ile Lys
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 60

Glu Gly Ser Leu Gln Pro Ile Ile Lys Thr
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 61

Gly Ser Leu Gln Pro Ile Ile Lys Thr Glu
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 62

Ser Leu Gln Pro Ile Ile Lys Thr Glu Gly
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 63

Leu Gln Pro Ile Ile Lys Thr Glu Gly Pro
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 64

Gln Pro Ile Ile Lys Thr Glu Gly Pro Thr
1               5                   10
```

```
<210> SEQ ID NO 65
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 65

Pro Ile Ile Lys Thr Glu Gly Pro Thr Leu
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 66

Ile Ile Lys Thr Glu Gly Pro Thr Leu Thr
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 67

Ile Lys Thr Glu Gly Pro Thr Leu Thr Lys
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 68

Lys Thr Glu Gly Pro Thr Leu Thr Lys Val
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 69

Thr Glu Gly Pro Thr Leu Thr Lys Val Lys
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 70

Glu Gly Pro Thr Leu Thr Lys Val Lys Ile
1               5                   10

<210> SEQ ID NO 71
<211> LENGTH: 10
```

```
<212> TYPE: PRT
<213> ORGANISM: Artificial Sequence
<220> FEATURE:
<223> OTHER INFORMATION: Chemically Synthesized

<400> SEQUENCE: 71

Tyr Thr Thr Lys Ile Ile Thr Lys Val Val
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 72

Ala Thr Thr Lys Ile Ile Thr Lys Ala Ala
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 73

Ala Ala Thr Lys Ile Ile Thr Lys Ala Ala
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 74

Ala Ala Ala Lys Ile Ile Thr Lys Ala Ala
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 75

Ala Ala Ala Ala Ile Ile Thr Lys Ala Ala
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 76

Ala Ala Ala Ala Ala Ile Thr Lys Ala Ala
1               5                   10

<210> SEQ ID NO 77
<211> LENGTH: 10
<212> TYPE: PRT
<213> ORGANISM: Artificial Sequence
```

```
<220> FEATURE:
<223> OTHER INFORMATION: Chemically Synthesized

<400> SEQUENCE: 77

Ala Thr Thr Lys Ile Ile Thr Ala Ala Ala
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 78

Ala Thr Thr Lys Ile Ile Ala Ala Ala Ala
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 79

Ala Thr Thr Lys Ile Ala Ala Ala Ala Ala
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 80

Ala Thr Thr Lys Ala Ala Ala Ala Ala Ala
1               5                   10
```